United States Patent
Skripps et al.

(10) Patent No.: US 9,937,006 B2
(45) Date of Patent: Apr. 10, 2018

(54) MULTI-SITE SURGICAL DRAPE AND METHOD

(71) Applicant: Allen Medical Systems, Inc., Batesville, IN (US)

(72) Inventors: Thomas K. Skripps, Acton, MA (US); Joshua C. Hight, Acton, MA (US); David P. Scott, Sterling, MA (US)

(73) Assignee: Allen Medical Systems, Inc., Batesville, IN (US)

( * ) Notice: Subject to any disclaimer, the term of this patent is extended or adjusted under 35 U.S.C. 154(b) by 366 days.

(21) Appl. No.: 14/735,746

(22) Filed: Jun. 10, 2015

(65) Prior Publication Data

US 2015/0272681 A1    Oct. 1, 2015

Related U.S. Application Data

(63) Continuation of application No. 13/326,159, filed on Dec. 14, 2011, now Pat. No. 9,072,646.

(Continued)

(51) Int. Cl.
*A61B 19/08* (2006.01)
*A61G 13/08* (2006.01)
(Continued)

(52) U.S. Cl.
CPC .............. *A61B 19/08* (2013.01); *A61B 46/00* (2016.02); *A61G 13/0054* (2016.11);
(Continued)

(58) Field of Classification Search
CPC ......... A61B 46/00; A61B 46/10; A61B 46/13; A61B 46/17; A61B 46/20; A61B 46/23; A61B 46/27; A61B 46/30; A61B 46/40; A61B 2046/201; A61B 2046/205; A61B 2046/234; A61B 2046/236; A61B 19/08; A61B 19/087; A61B 19/10; A61B 19/12; A61B 2019/084; A61G 13/0054; A61G 13/04; A61G 13/08; A61G 13/122; A61G 13/1245; A61G 13/1275; A61G 7/0504; A61G 7/0526; A61F 2013/15008; A61F 2013/15073; A61F 5/3769; A61F 5/3776; A61F 5/3784; A61F 5/3792
(Continued)

(56) References Cited

U.S. PATENT DOCUMENTS 3,835,851 A  *  9/1974  Villari .................... A61B 46/00
                                                         128/853
3,926,185 A  *  12/1975  Krzewinski ............ A61B 46/00
                                                         128/854

(Continued)

*Primary Examiner* — Ophelia A Hawthorne
(74) *Attorney, Agent, or Firm* — Barnes & Thornburg LLP

(57) ABSTRACT

A patient support for use with a foundation frame is disclosed. The foundation frame includes a first column and a second column. The patient support includes a base beam, a leg support, and a guide. The base beam is coupleable to the foundation frame to be supported by the first column and the second column. The leg support has a first end pivotably coupled to the base beam and a second end spaced apart from the first end. The, guide is coupled to the base beam and to the second end of the leg support. The guide is configured to guide the second end of the leg support along an arcuate path when the leg support pivots relative to the base beam.

14 Claims, 58 Drawing Sheets

Related U.S. Application Data

(60) Provisional application No. 61/422,874, filed on Dec. 14, 2010.

(51) Int. Cl.
| | | |
|---|---|---|
| *A61G 13/04* | (2006.01) | |
| *A61B 46/00* | (2016.01) | |
| *A61G 13/00* | (2006.01) | |
| *A61G 13/12* | (2006.01) | |
| *A61B 46/20* | (2016.01) | |

(52) U.S. Cl.
CPC ............. *A61G 13/04* (2013.01); *A61G 13/08* (2013.01); *A61G 13/122* (2013.01); *A61G 13/1245* (2013.01); *A61B 2046/205* (2016.02); *A61G 13/1275* (2013.01)

(58) Field of Classification Search
USPC .......................................... 128/849–856, 898
See application file for complete search history.

(56) References Cited

U.S. PATENT DOCUMENTS

| | | | |
|---|---|---|---|
| 3,930,497 A | 1/1976 | Krebs et al. | |
| 4,033,341 A | 7/1977 | Scrivens | |
| 4,040,418 A | 8/1977 | Collins | |
| 4,119,093 A | 10/1978 | Goodman | |
| 4,134,398 A | 1/1979 | Scrivens | |
| 4,166,461 A | 9/1979 | Oliver et al. | |
| 4,196,723 A | 4/1980 | Moose, Jr. | |
| 4,266,663 A | 5/1981 | Geraci | |
| 4,275,720 A | 6/1981 | Wichman | |
| 4,321,917 A | 3/1982 | Campbell | |
| 4,334,529 A | 6/1982 | Wirth | |
| 4,336,797 A | 6/1982 | Latucca et al. | |
| 4,414,968 A | 11/1983 | Amin | |
| 4,471,769 A | 9/1984 | Lockhart | |
| 4,569,341 A | 2/1986 | Morris | |
| 4,586,498 A | 5/1986 | Morris | |
| 4,627,427 A * | 12/1986 | Arco ...................... | A61B 46/00 128/853 |
| 4,730,609 A | 3/1988 | McConnell | |
| 4,890,628 A | 1/1990 | Jackson | |
| 4,957,120 A | 9/1990 | Grier-Idris | |
| 5,042,507 A | 8/1991 | Dowdy | |
| 5,074,316 A | 12/1991 | Dowdy | |
| 5,178,162 A | 1/1993 | Bose | |
| 5,394,891 A | 3/1995 | Mills et al. | |
| 5,396,905 A | 3/1995 | Newman et al. | |
| 5,398,700 A | 3/1995 | Mills et al. | |
| 5,464,024 A | 11/1995 | Mills et al. | |
| 5,615,423 A | 4/1997 | Faries, Jr. et al. | |
| 5,778,891 A | 7/1998 | McMahan | |
| 5,816,252 A | 10/1998 | Faries, Jr. et al. | |
| 5,832,925 A | 11/1998 | Rothrum | |
| 5,875,780 A | 3/1999 | Rodriguez | |
| 5,901,706 A | 5/1999 | Griesbach et al. | |
| 5,941,907 A | 8/1999 | Augustine | |
| 5,975,082 A | 11/1999 | Dowdy | |
| 6,032,670 A | 3/2000 | Miller | |
| 6,055,987 A | 5/2000 | Griesbach et al. | |
| 6,213,124 B1 | 4/2001 | Butterworth | |
| 6,216,700 B1 | 4/2001 | Griesbach et al. | |
| 6,298,855 B1 | 10/2001 | Baird | |
| 6,314,959 B1 | 11/2001 | Griesbach et al. | |
| 6,615,836 B1 | 9/2003 | Griesbach et al. | |
| 6,615,837 B1 | 9/2003 | Griesbach, III | |
| 6,694,981 B2 | 2/2004 | Gingles et al. | |
| 6,810,881 B2 | 11/2004 | Faries, Jr. et al. | |
| 6,843,252 B2 | 1/2005 | Harrison et al. | |
| 6,910,485 B2 | 6/2005 | Faries, Jr. et al. | |
| 6,994,091 B2 | 2/2006 | Griesbach, III | |
| 7,044,132 B2 | 5/2006 | Masini | |
| 7,086,404 B2 | 8/2006 | Dusenbery et al. | |
| 7,108,713 B1 | 9/2006 | Augustine | |
| 7,305,991 B2 | 12/2007 | Santilli et al. | |
| 7,347,210 B2 | 3/2008 | Faries, Jr. et al. | |
| 7,409,953 B2 | 8/2008 | Griesbach, III | |
| 7,458,376 B2 | 12/2008 | Aboul-Hosn et al. | |
| 7,533,673 B2 | 5/2009 | Lewis et al. | |
| 7,594,512 B2 | 9/2009 | Reyes et al. | |
| 7,610,918 B2 | 11/2009 | Bowen et al. | |
| 7,727,244 B2 | 6/2010 | Orban, III et al. | |
| 7,770,583 B2 | 8/2010 | Harris et al. | |
| 7,891,359 B2 | 2/2011 | Corbitt, Jr. et al. | |
| 7,997,277 B2 | 8/2011 | Reyes et al. | |
| 8,074,657 B2 | 12/2011 | Scott et al. | |
| 8,079,365 B2 | 12/2011 | Block et al. | |
| 8,202,278 B2 | 6/2012 | Orban, III et al. | |
| 8,371,306 B2 | 2/2013 | Haines et al. | |
| 8,424,532 B2 | 4/2013 | Esquivel et al. | |
| 8,726,907 B2 | 5/2014 | Strauch et al. | |
| 8,807,138 B2 | 8/2014 | Byers et al. | |
| 8,826,912 B2 | 9/2014 | Bream, Jr. | |
| 8,844,538 B2 | 9/2014 | Stang | |
| 8,893,721 B2 | 11/2014 | Futrell, Jr. | |
| 9,072,646 B2 | 7/2015 | Skripps et al. | |
| 2002/0000232 A1 * | 1/2002 | Levitt .................... | A61B 46/00 128/853 |
| 2006/0185091 A1 * | 8/2006 | Jackson ................. | A61G 7/001 5/621 |
| 2006/0248650 A1 * | 11/2006 | Skripps .............. | A61G 13/0054 5/621 |
| 2010/0192300 A1 * | 8/2010 | Tannoury ............ | A61G 13/0036 5/607 |
| 2011/0214679 A1 * | 9/2011 | Chua ..................... | A61B 46/00 128/855 |
| 2013/0269710 A1 * | 10/2013 | Hight .................... | A61G 13/04 128/845 |

\* cited by examiner

US 9,937,006 B2

MULTI-SITE SURGICAL DRAPE AND METHOD

CROSS REFERENCE TO RELATED APPLICATIONS

The present application is a continuation of Ser. No. 13/326,159, filed Dec. 14, 2011, which claims priority under 35 U.S.C. § 119(e) to U.S. Provisional Application Ser. No. 61/422,874 which was filed Dec. 14, 2010, which is expressly incorporated by reference herein

BACKGROUND

The present disclosure relates to patient support apparatuses for use during surgery. More particularly, the present disclosure relates to patient support apparatuses operable to reposition a patient during surgery.

In some surgeries, it may be advantageous for the patient to be positioned in a lateral position so that a surgeon can access a first surgical sight and then repositioned so that a surgeon can access other necessary surgical sights. This dual approach surgery can require the patient to first be positioned in a lateral position, lying on his side, on a first patient support. The patient may then be transferred to a stretcher while the first patient support is replaced with a second patient support configured to support the patient in a different position. Next, the patient is transferred onto the second patient support so that the next surgical approach can be performed. Other patient supports allow the patient to be supported in a lateral position and then repositioned relative to the same patient support so that the patient is positioned in another position. Repositioning a patient during surgery on different patient supports or even on the same patient support can be dangerous for the patient and/or difficult for care givers.

SUMMARY

The present invention comprises one or more of the features recited in the appended claims and/or the following features which, alone or in any combination, may comprise patentable subject matter.

According to one aspect of the present disclosure, a patient support apparatus may be used with a foundation frame including a first column and a second column. The patient support may include a base beam, a leg support, and a guide. The base beam may be adapted to mount to the foundation frame. The leg support may have a first end pivotably coupled to the base beam and a second end spaced apart from the first end. The guide may be coupled to the base beam and to the second end of the leg support. The guide may be configured to guide the second end of the leg support along an arcuate path when the leg support pivots relative to the base beam.

In some embodiments, the guide may include an arcuate track engaging the leg support. The arcuate track may define the arcuate path of the second end of the leg support.

In some embodiments, the leg support may include a leg support beam and a platform. The leg support beam may be received in the arcuate track of the guide. The platform may be coupled to and extending out from the leg support beam.

In some embodiments, the guide may include a drive coupled to the leg support beam. The drive may be configured to move the second end of the leg support along the arcuate track of the guide.

In some embodiments, the drive may include a hand crank. It is contemplated that the drive may include a motor.

In some embodiments, the base beam may include a first section and a second section. The first section may form a first end of the base beam. The second section may form a second end of the base beam. The second section may extend at an angle relative to the first section.

In some embodiments, the leg support may pivot between a first position and a second position. The leg support when in the first position may be substantially parallel to the first section of the base beam. The leg support when in the second position may form an angle with the first section of the base beam.

In some embodiments, the second end of the leg support may move toward the second section of the base beam when the leg support moves from the first position to the second position.

In some embodiments, the patient support may further include a first adapter and a second adapter. The first adapter may be coupled to the first end of the base beam. The second adapter may be coupled to the second end of the base beam. The first adapter may be configured to couple to the first column of the foundation frame. The second adapter may be configured to couple to the second column of the foundation frame. It is contemplated that the first adapter and the second adapter may be quick disconnect adapters.

In some embodiments, the patient support may further include a first torso support and a second torso support. At least one of the first torso support and the second torso support may be slidably coupled to the first section of the base beam.

In some embodiments, the first torso support and the second torso support may each include a first member and a second member. The first member may be coupled to the first section of the base beam. The second member may be spaced apart from the base beam and may extend substantially perpendicular to the first member.

In some embodiments, the patient support may further include a leg wrap support coupled to the leg support. The leg wrap support may be configured to wrap around a patient's legs to secure the patient's legs to the leg support.

In some embodiments, the leg wrap support may be sized to extend over most of the length of the patient's legs.

In some embodiments, the leg wrap support may include a vacuum bag and a number of beads situated inside the vacuum bag.

According to another aspect of the present disclosure, a patient support apparatus may be used with a foundation frame including a first column and a second column. The patient support may include a base beam, a leg support, and a torso support. The base beam may be coupleable to the foundation frame to be supported by the first column and the second column. The leg support may have a first end pivotably coupled to the base at a second end of the base beam. The torso support may have a first end pivotably coupled to the base beam at a first end of the base beam.

In some embodiments, the leg support may include a leg support beam and a platform. The leg support beam may be coupled to the base beam. The platform may extend out from the leg support beam.

In some embodiments, the torso support may include a torso support beam, a first contoured support, and a second contoured support. The first contoured support may be coupled to the torso support beam. The second contoured support may be coupled to the torso support beam.

In some embodiments, the first contoured support and the second contoured support may be slidable along the torso support beam.

In some embodiments, the base beam may include a first section and a second section. The second section may be offset from the first section and substantially parallel to the first section.

According to another aspect of the present disclosure, a method of positioning a patient during surgery may include rolling the patient from a supine position on a preoperative table to a lateral position on a patient support coupled to a foundation frame, securing the patient to the patient support, and lowering a leg support of the patient support causing lateral flexion of the patient's torso relative to the patient's legs so that the top of the patient's pelvis is moved away from the patient's rib cage.

In some embodiments, the method of positioning the patient may further include rotating the patient support relative to the foundation frame so that the patient is supported in a substantially prone position. The patient support may include a base beam and a torso support coupled to the base beam. The base beam may underlie and directly support the patient when the patient is in the lateral position. The base beam may be moved out from under the patient and indirectly support the patient via the torso support cantilevered out from the base beam when the patient is in the prone position.

In some embodiments, the patient support may include a base beam and a guide. The leg support may have a first end pivotably coupled to the base beam and a second end coupled to the guide.

In some embodiments, the guide may include an arcuate track slidably receiving the second end of the leg support. The guide may be configured to guide the second end of the leg support along an arcuate path when the leg support is lowered.

In some embodiments, the method of positioning the patient may further comprise sliding a first torso support along the base beam into position to engage the patient's chest when the patient is secured to the patient support and sliding a second torso support along the base beam into a position to engage the patient's hips when the patient is secured to the patient support.

In some embodiments, the method of positioning the patient may further include wrapping a surgical drape around the patient. The surgical drape may include a main sheet section, a first pull-away section coupled to the main sheet section, and a second pull-away section coupled to the main sheet section.

In some embodiments, the method of positioning the patient may further include pulling the first pull-away section to expose at least part of an opening in the main sheet section while the first pull-away section remains coupled to the main sheet section and pulling away the second pull-away cover sheet to expose at least part of an opening in the main sheet while the second pull-away section remains coupled to the main sheet section.

In some embodiments, securing the patient to the patient support may include wrapping a vacuum bag containing a number of beads around the patient's legs and applying vacuum to the vacuum bag.

According to another aspect of the present disclosure, a method of positioning a patient during surgery may include rolling the patient from a prone position on a preoperative table to a lateral position on a patient support coupled to a foundation frame, securing the patient to the patient support, and rotating the patient support relative to the foundation frame so that the patient is supported in a substantially supine position.

In some embodiments, securing the patient to the patient support includes wrapping a vacuum bag containing a number of beads around the patient's legs and applying vacuum to the vacuum bag.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which:

FIG. 17A is a perspective view of the surgical support of FIG. 12 during an initial operation of the drape process in which a patient is supported by the surgical support in the lateral position and a drape is wrapped around the patient;

FIG. 17B is a view similar to FIG. 17A showing an intermediate operation of the drape process in which a first portion of the drape is unwrapped from the patient to expose a first surgical area;

FIG. 17C is a view similar to FIGS. 17A and 17B showing another operation of the drape process in which a second portion of the drape is unwrapped from the patient to expose a second surgical area;

FIG. 25 is a perspective view of the surgical support of FIG. 23a;

FIG. 28 is a perspective view of the surgical support of FIG. 26a;

FIG. 29 is a perspective view of a surgical support arranged in a lateral position prior to transferring the patient who is lying in a supine position on a stretcher adjacent the surgical support to the patient support so that the patient is arranged to face toward the torso supports as suggested in FIG. 30;

FIG. 30 is a view similar to FIG. 29 showing the patient transferred to the surgical support being supported by the surgical support in a lateral-horizontal position and showing the caregiver holding the patient in the lateral-horizontal position until a first torso-support wrap can be coupled around the patient as suggested in FIG. 31;

FIG. 31 is a view similar to FIG. 30 showing the caregiver coupling the first torso wrap to the patient;

FIG. 32 is a view similar to FIG. 31 showing the first torso wrap coupling the patient to the first torso support and showing the caregiver coupling a second torso wrap to the patient;

FIG. 33 is a view similar to FIG. 32 showing the first and second torso wraps coupling the patient to the torso supports and showing the caregiver wrapping a vacuum bag around the legs of the patient;

FIG. 34 is a view similar to FIG. 33 showing the vacuum bag wrapped around the patient's legs and showing the caregiver wrapping a first leg-wrap strap around the vacuum bag;

FIG. 35 is a view similar to FIG. 34 showing the vacuum bag after the leg-vacuum has been secured to the leg support by the leg-wrap straps and showing the caregiver preparing to remove air from the vacuum bag so that the vacuum bag stiffens and becomes rigid as suggested in FIG. 36;

FIG. 36 is a view similar to FIG. 35 showing the vacuum bag wrapped around the legs of the patient and secured to the leg support with air removed from the vacuum bag so that the vacuum bag is rigid;

FIG. 37 is a view similar to FIG. 36 showing rearrangement of the patient support to cause the patient to be supported by the patient support in a lateral-flexion position in which the patient's legs have been lowered relative to the patient's torso;

FIG. 38 is a view similar to FIG. 36 showing both rotation of the patient support and the patient relative to the foundation frame without repositioning the patient relative to the patient support;

FIG. 39 is a view similar to FIG. 38 showing the patient support rotated relative to the foundation frame to cause the patient resting on the patient support to be in a prone position (face down) without repositioning the patient relative to the patient support;

FIG. 40 is a view similar to FIG. 29 showing the surgical support arranged in a lateral position prior to transferring the patient from a stretcher adjacent the surgical support to the patient support;

FIG. 41 is a view similar to FIG. 40 showing the patient lying on the stretcher in a prone position (face down) prior to rotating the patient off the stretcher and onto the surgical support so that the patient is arranged to face away from the torso supports as suggested in FIG. 42;

FIG. 42 is a view similar to FIG. 41 showing the patient resting on the surgical support in a lateral-horizontal position and showing the caregiver holding the patient in the lateral-horizontal position until the first torso-support wrap can be coupled around the patient as suggested in FIG. 43;

FIG. 43 is a view similar to FIG. 42 showing the first torso-support wrap coupled around the patient and showing the caregiver placing the patient's arms in an arm support coupled to a second adapter included in the patient support;

FIG. 44 is a view similar to FIG. 43 showing that the caregiver has placed the patient's arms in the arm support and that the caregiver is coupling the second torso-wrap around the patient;

FIG. 45 is a view similar to FIG. 44 showing the caregiver inserting a cushion between the patients legs prior to wrapping a vacuum bag around the patient's legs as suggested in FIG. 46;

FIG. 46 is a view similar to FIG. 45 showing the caregiver wrapping the vacuum bag around the patient's legs;

FIG. 47 is a view similar to FIG. 46 showing the caregiver wrapping the pair of leg-wrap straps around the vacuum bag to couple the vacuum bag and patient's legs to the leg support;

FIGS. 48-50 are a series of views showing movement of the leg support to cause the patient's legs to move therewith from the lateral-horizontal position of FIG. 48 to the lateral-flexion position of FIG. 50;

FIG. 48 is a view similar to FIG. 47 showing the caregiver using a handle included in the guide to move the leg support downwardly relative to the base beam so that the leg support lies at the angle α suggested in FIG. 50;

FIG. 49 is a view similar to FIG. 48 showing the caregiver continuing to rotate the handle causing the leg support to move to a lateral-intermediate position between the lateral-horizontal position and the lateral-flexion position;

FIG. 50 is a view similar to FIG. 49 showing the leg support moved downwardly so that the angle α is established and the patient is supported in the lateral-flexion position;

FIG. 51 is a view similar to FIG. 50 showing initial rotation of both the patient support and the patient relative to the foundation frame without repositioning the patient relative to the patient support;

FIG. 52 is a view similar to FIG. 51 showing continued rotation of the patient support and the patient toward a supine position (face up); and FIG. 53 is a view similar to FIG. 52 showing the patient in the supine position after the patient support has rotated 90 degrees relative to the foundation frame.

DETAILED DESCRIPTION

Figure 1:
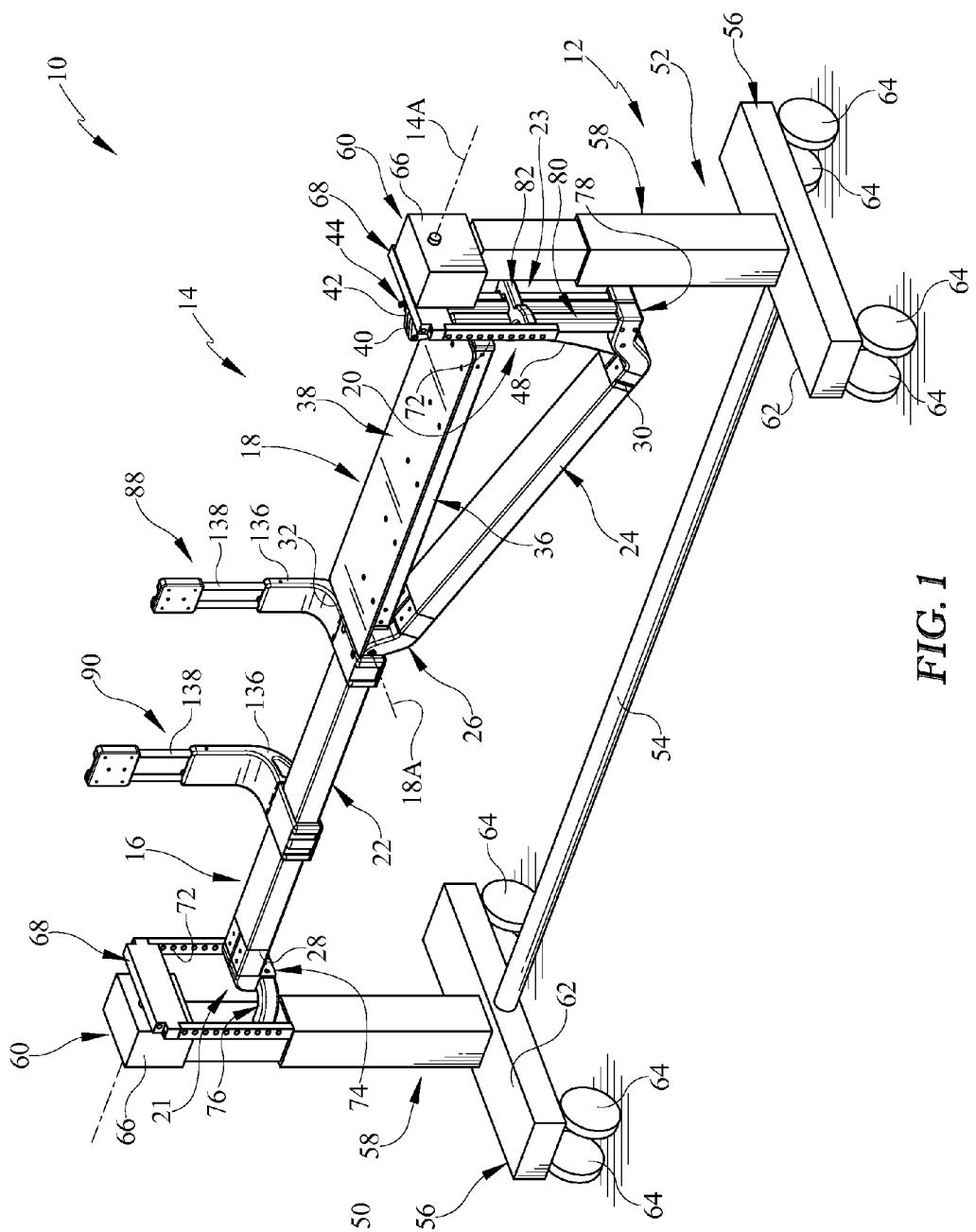
FIG. 1 is a perspective view of a first embodiment of a surgical support in accordance with the present disclosure showing that the surgical support includes a foundation frame and a patient support coupled to the foundation frame and that the patient support is arranged to support a patient in a lateral position (side lying)

Referring to FIGS. 1-20, an illustrative surgical support 10 for supporting a patient in a number of position during surgery is shown. As shown in FIG. 1, the surgical support 10 includes a foundation frame 12 and a patient support 14 mounted on the foundation frame 12. The foundation frame 12 is illustratively a "Jackson Table" as is known in the art but in other embodiments may be another suitable frame for supporting the patient support 14. The patient support 14 is coupled to the foundation frame 12 for pivotable movement about a patient support axis 14A parallel to the length of the patient support 14 so that a patient resting on the surgical support 10 can be repositioned during a surgical procedure.

Figure 36:
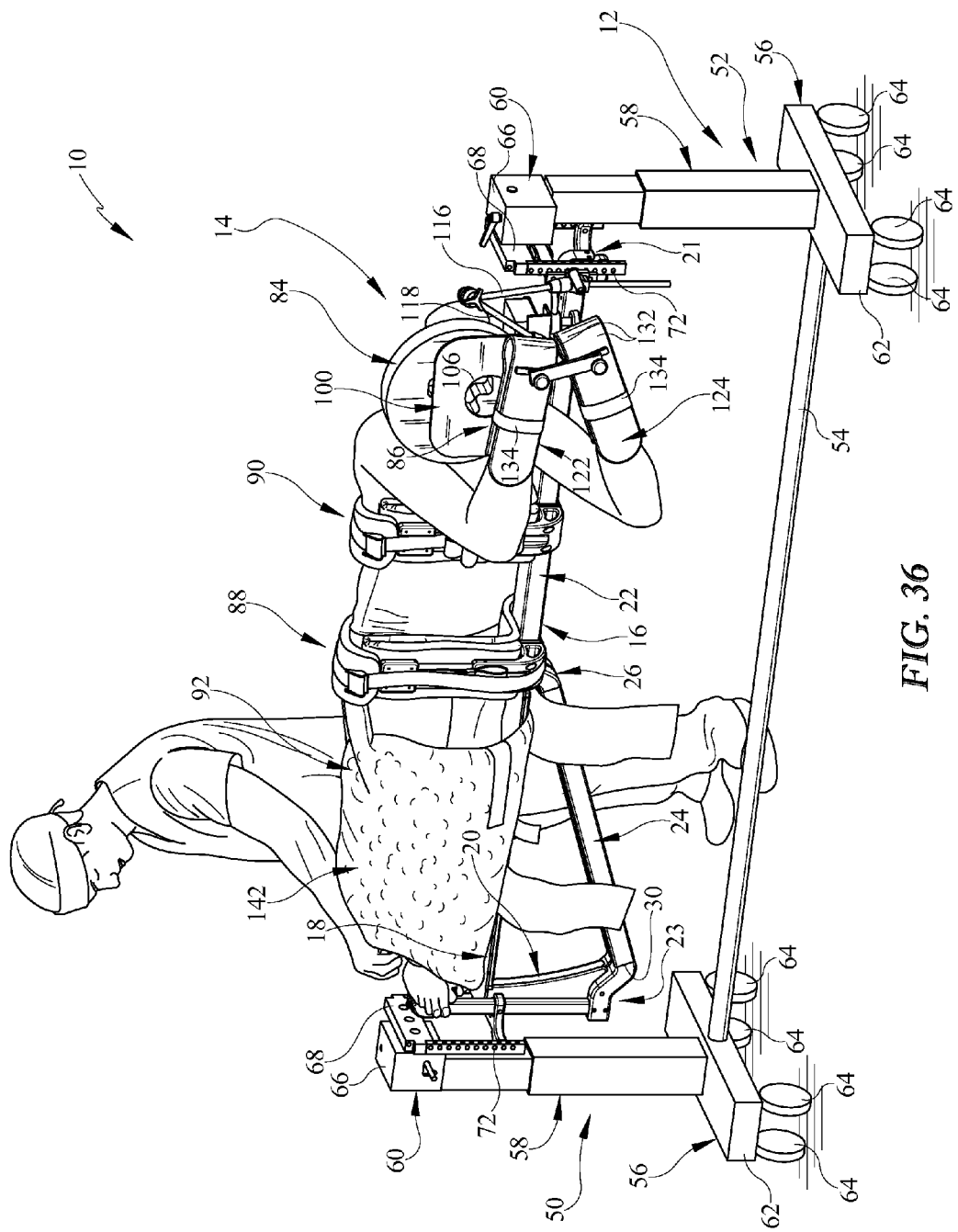
Figure 39:
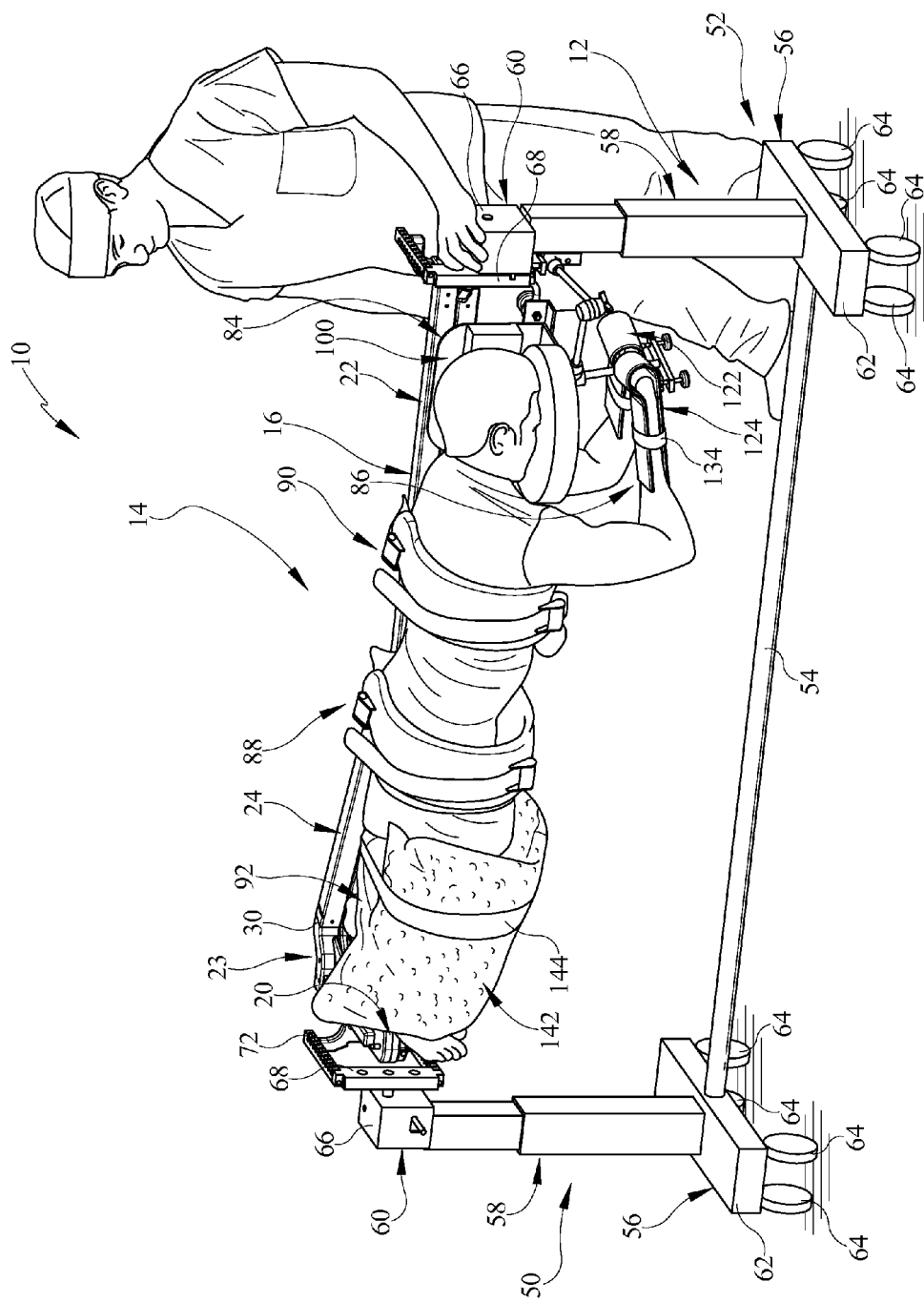
Figure 40:
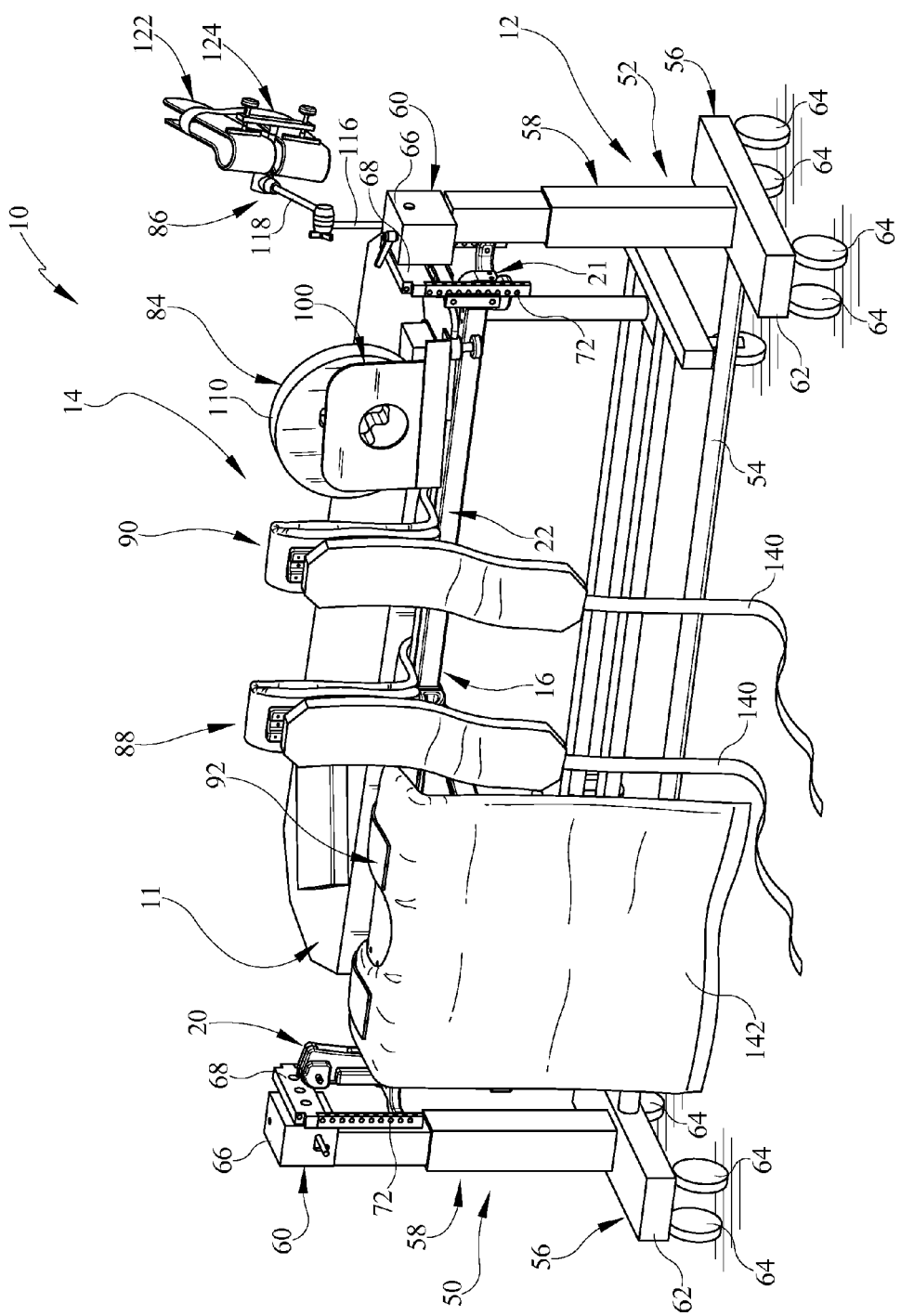
FIGS. 40-53 are a series of view showing an illustrative process for moving a patient onto the surgical support and then adjusting the position of the patient using the patient support.
Figure 48:
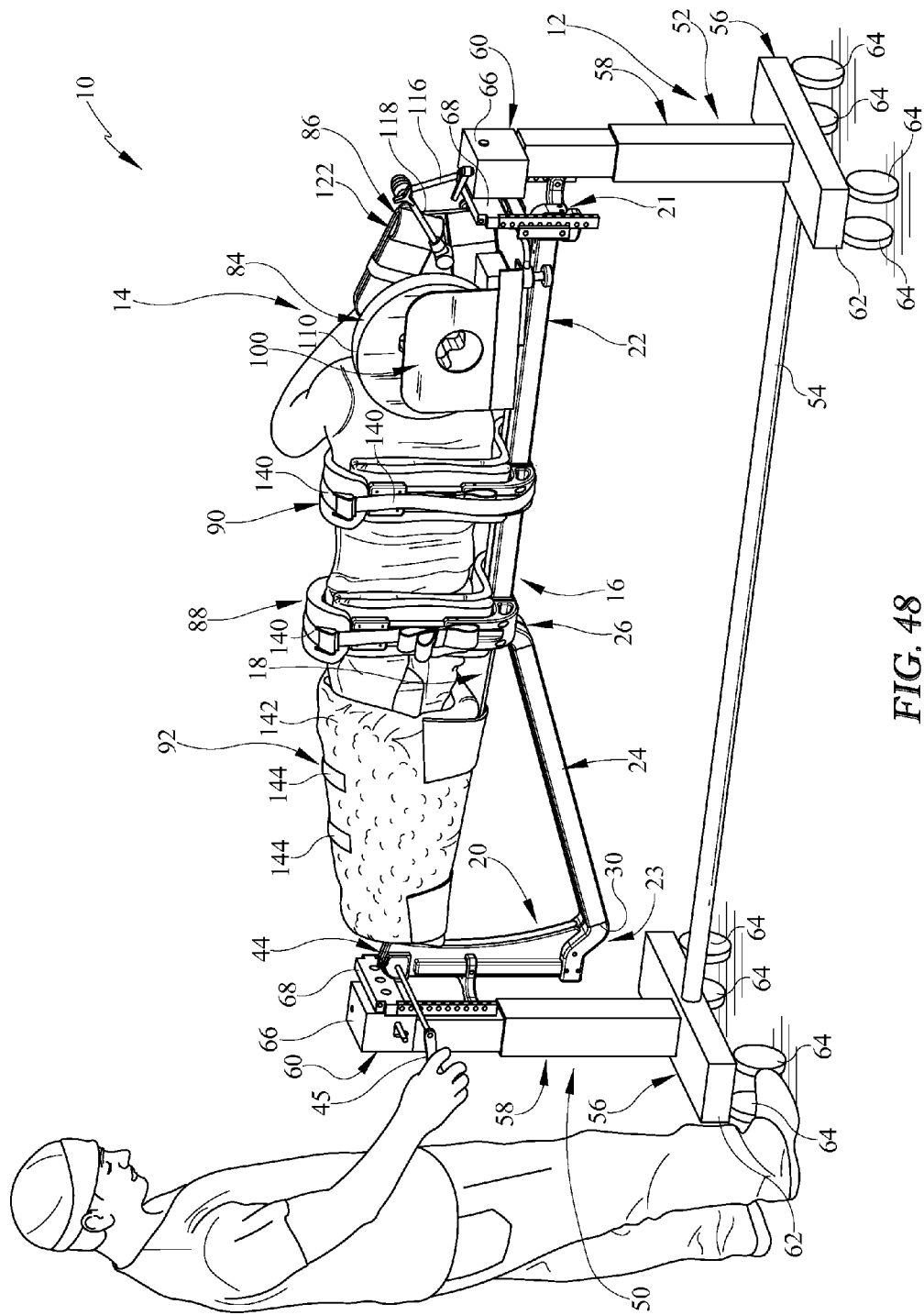
Figure 53:
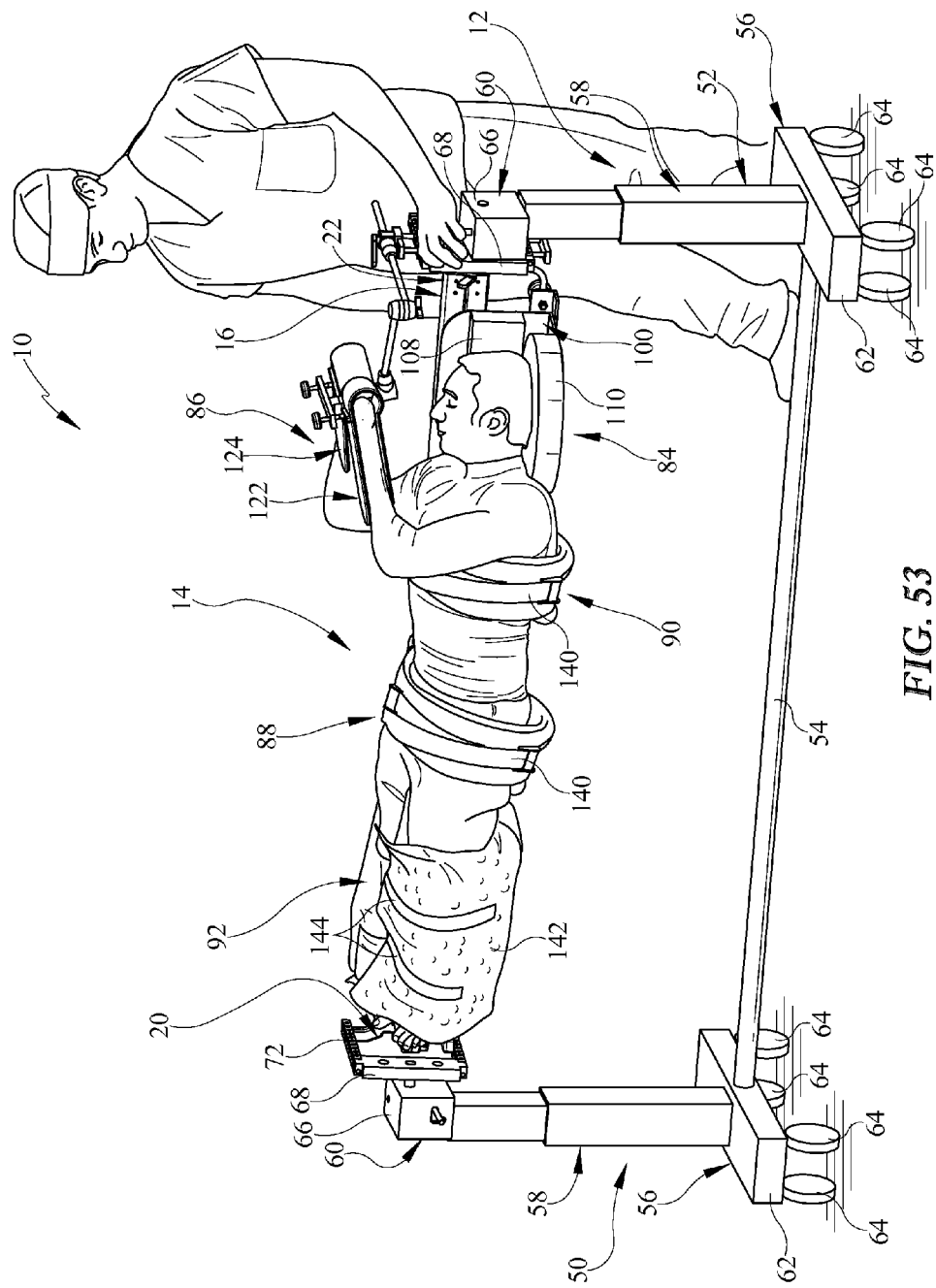

By pivoting the patient support 14 about the axis 14A, the patient resting on the patient support 14 can be moved between a lateral (or side-lying) position, as shown for example in FIG. 36, and a prone (or face-down) position, as shown for example in FIG. 39. Alternatively, the patient supported on the patient support 14 can be moved between a lateral position, as shown in FIG. 48, and a supine (or face-up) position, as shown in FIG. 53. Moving a patient between the lateral position and the prone/supine position during a surgical procedure may be undertaken in a number of medical procedures to increase accessibility of different parts of the patient's anatomy during different parts of a procedure. For example, during an extreme (or direct) lateral interbody fusion (XLIF/DLIF), a surgeon may access the patient's spine while the patient is in the lateral position to place a spinal implant and then move the patient to the prone position to place screws, plates, rods, and the like to secure the implant.

Figure 6:
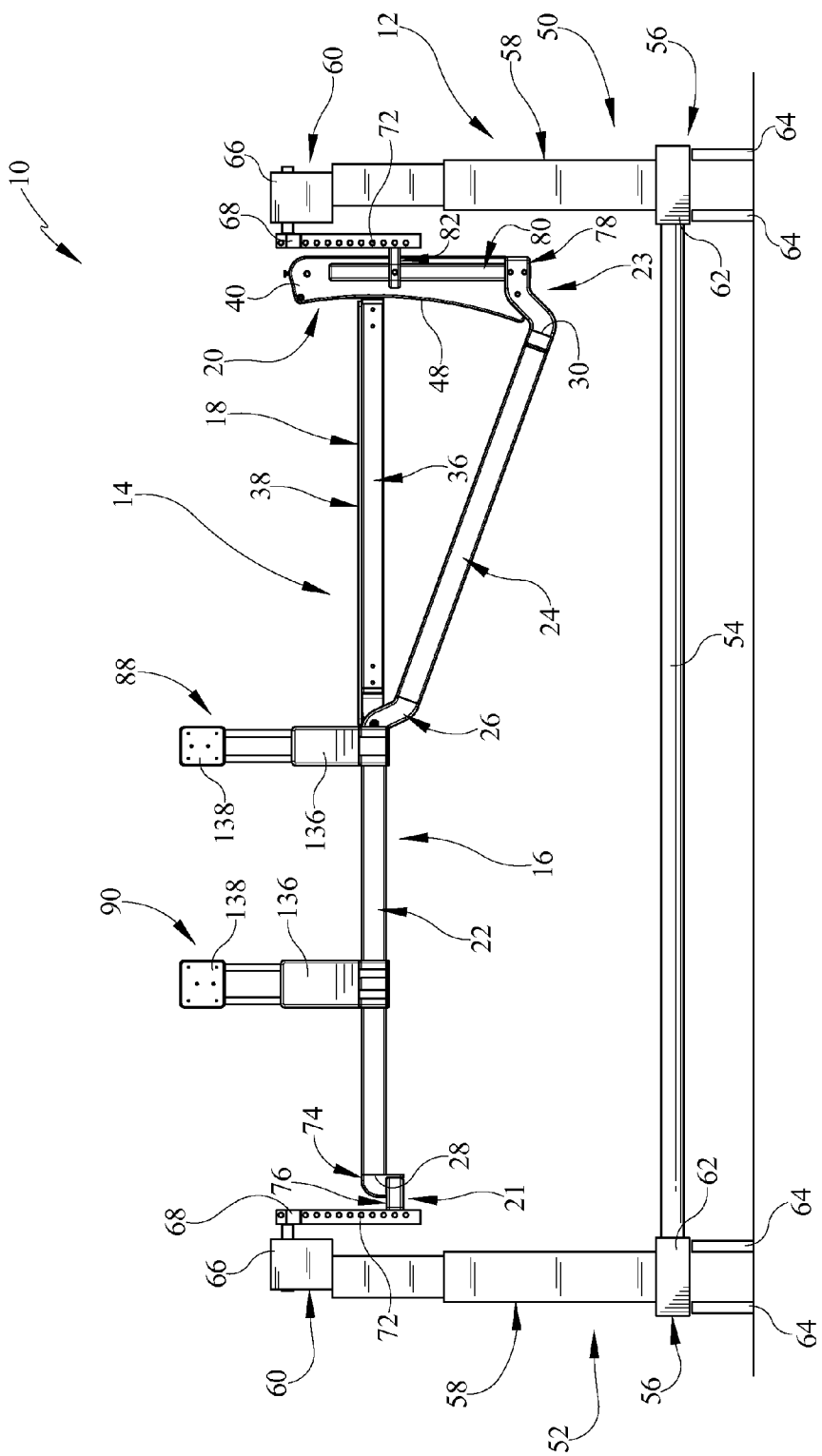
FIG. 6 is a left-side elevation view of the surgical support of FIG. 1 showing a pair of torso supports coupled a base beam included in the patient support.
Figure 7:
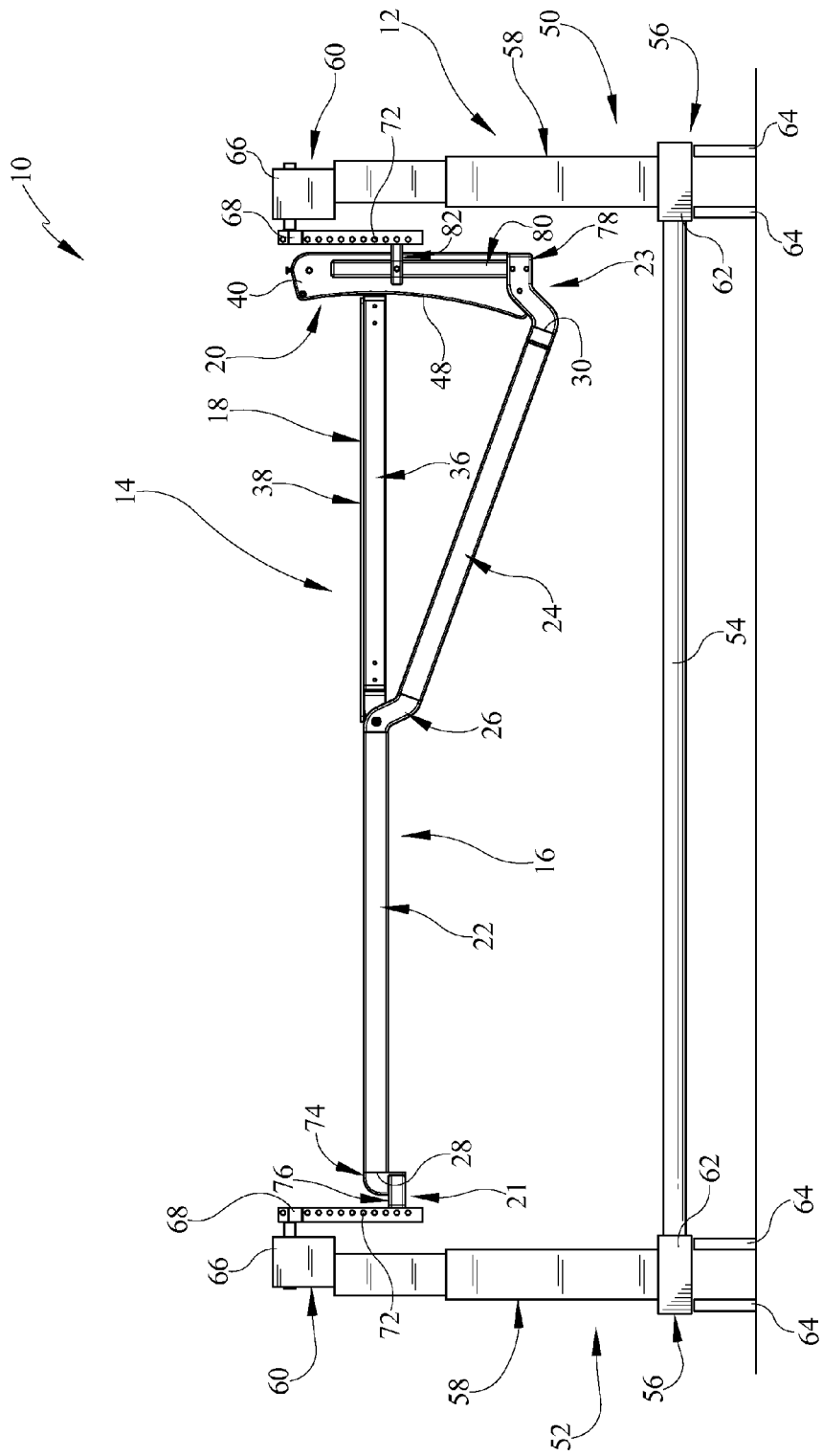
FIG. 7 is a view similar to FIG. 6 with the pair of torso supports removed.
Figure 8:
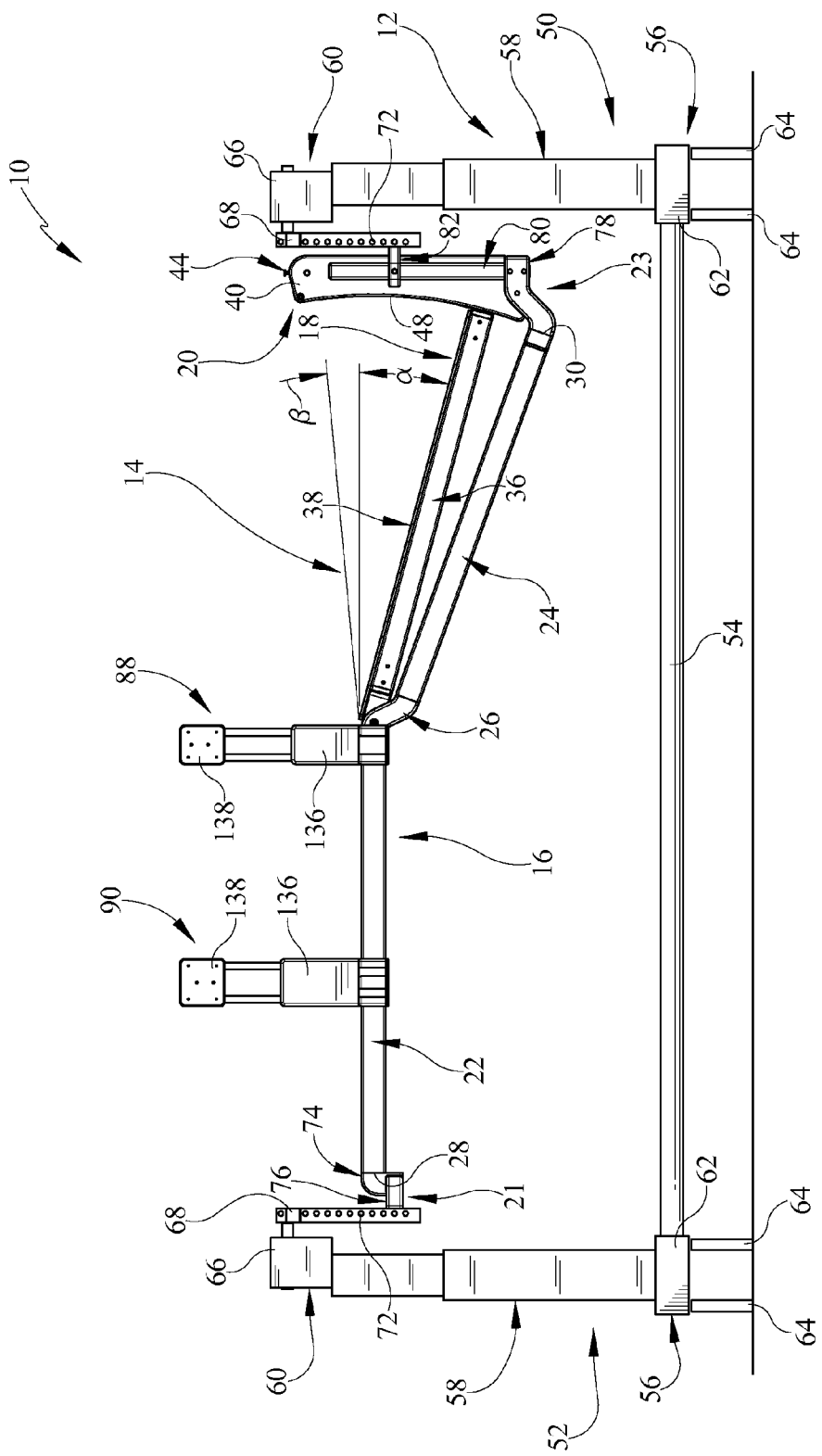
FIG. 8 is a view similar to FIG. 6 showing that the patient support includes a guide that interconnects a leg support to the foundation frame to cause the leg support to extend downwardly from the horizontal so that an angle of α degrees is established between the leg support and the base beam of the patient support.
Figure 9:
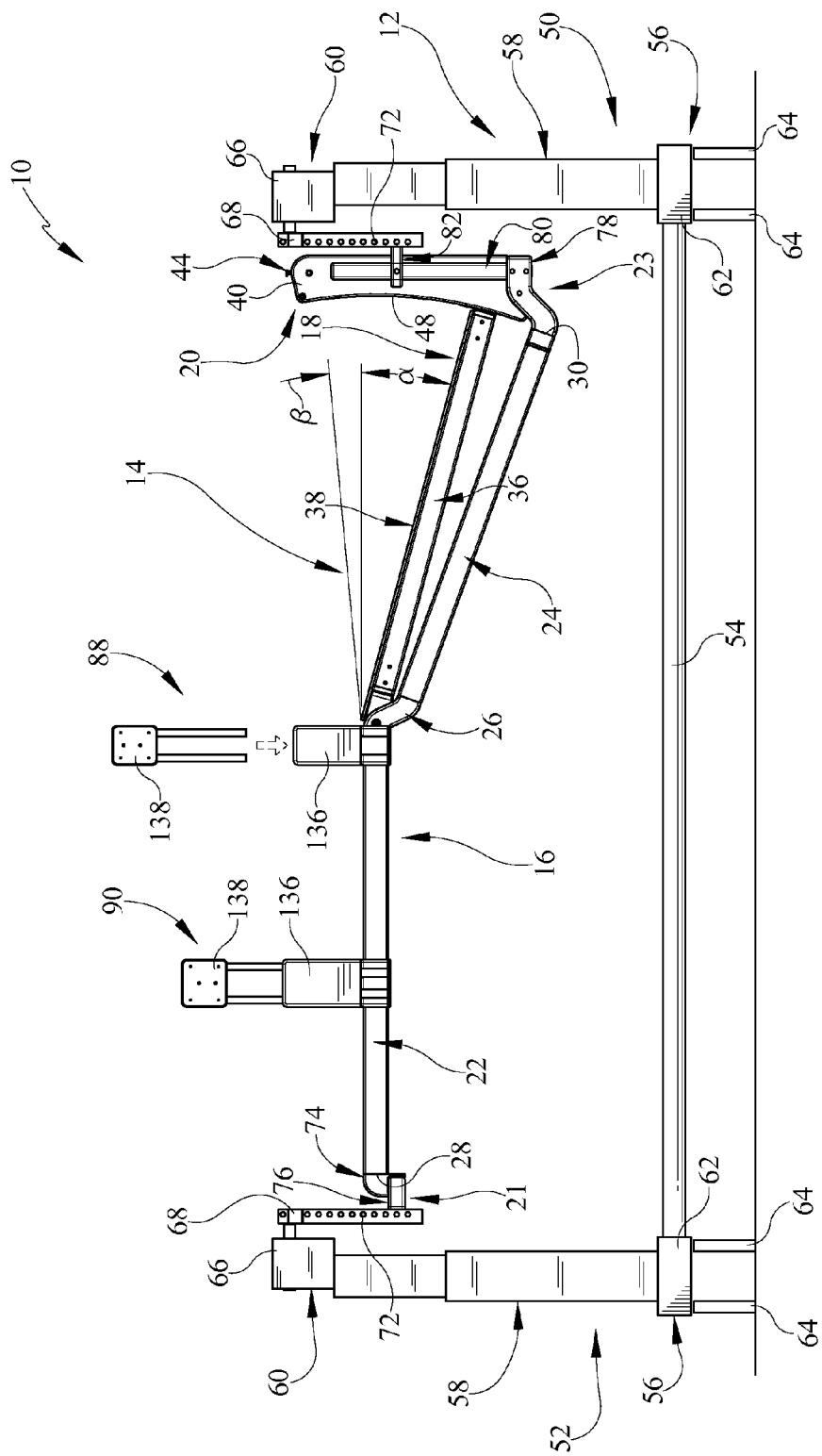
FIG. 9 is a view similar to FIG. 8 with an extension included in the first torso support being removed from an L-shaped bracket included in the first torso support for better access to the patient by a caregiver.
Figure 10:
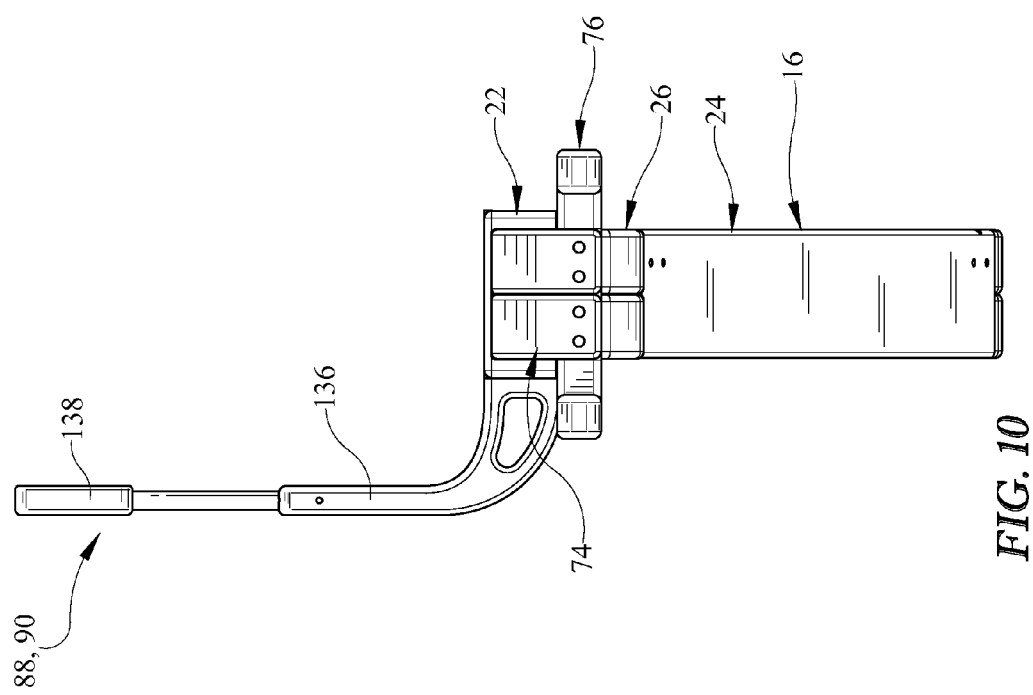
FIG. 10 is a partial foot-end elevation view of the surgical support of FIG. 1.
Figure 11:
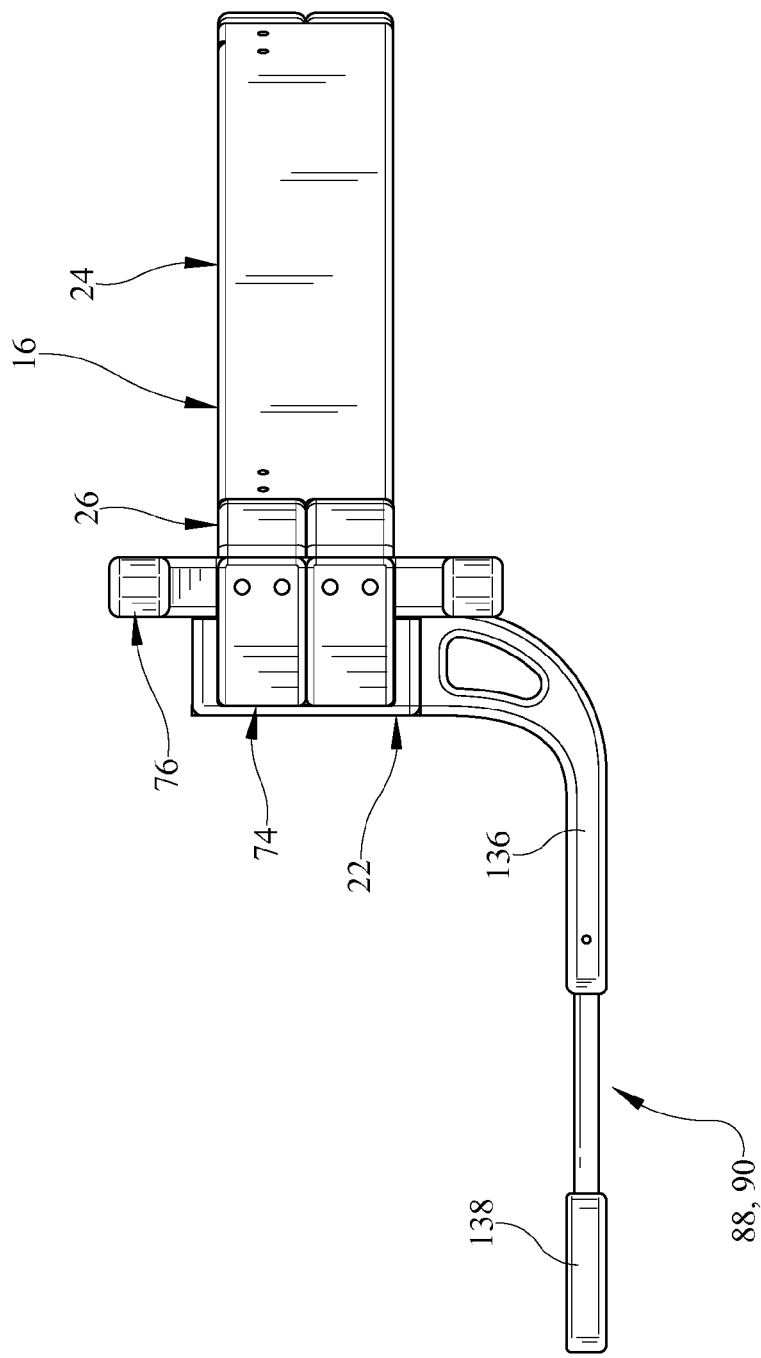
FIG. 11 is a partial foot-end elevation view of the surgical support of FIG. 4.

The patient support 14 illustratively includes a base beam 16, a leg support 18 that is pivotably coupled to the base beam 16, and a guide 20 for guiding the leg support 18 when the leg support pivots relative to the base beam 16. The base beam 16 includes a first section 22 configured to support the torso of the patient supported on the patient support 14. The leg support 18 is configured to support the legs of the patient supported on the patient support 14. The leg support 18 pivots about an axis 18A between a horizontal position parallel to the first section 22 of the base beam 16, as shown in FIG. 6, and a number of declined positions forming an angle α with the first section 22 of the base beam 16, as shown in FIG. 8. The leg support 18 may also be pivoted up from the horizontal position to a number of inclined positions forming an angle β with the first section 22 of the base beam 16, as shown in FIG. 8. In the illustrative embodiment, α is about 25 degrees and β is about 5 degrees.

Figure 37:
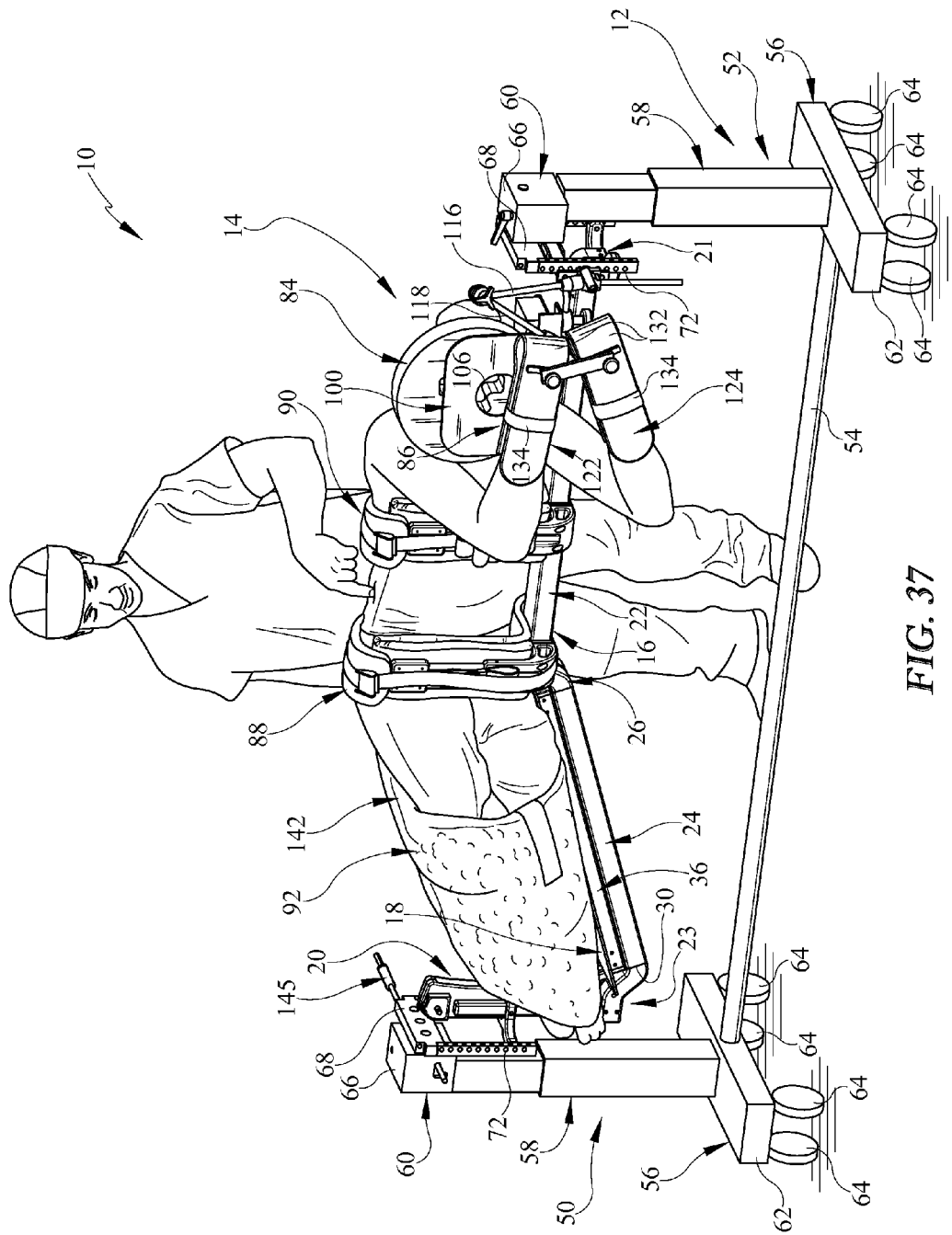

The leg support 18 may be moved to an inclined position to compensate for the width of the patients hips and to straighten a patient's spine. As shown in FIG. 37, moving the leg support 18 from the inclined position or the horizontal position to one of the declined positions while a patient is supported on the patient support 14 causes lateral flexion of the patient's torso relative to the patient's legs. When the patient is subjected to lateral flexion, the patient's pelvis is moved away from the patient's rib cage along the side of the patient spaced apart from the base beam 16 and the leg support 18. Space between the patient's pelvis and rib cage may allow a surgeon to access portions of the patient's anatomy such as the spine (especially the lower vertebrae) and kidneys, through the patient's side. In one example, a surgeon may access the patient's spine from the side during an XLIF/DLIF procedure when the surgeon is placing a spinal implant.

In the illustrative embodiment, as shown in FIG. 1, the base beam 16 of the patient support 14 has a rectangular cross-section and includes the first section 22, a second section 24, and a jog 26 extending from the first section 22 to the second section 24. The first section 22 forms a first end 28 of the base beam 16. The second section 24 extends at an angle from the first section 22. Also, the second section 24 forms the second end 30 of the base beam 16. The jog 26 is illustratively a loose Z-shaped segment extending between the first section 22 to the second section 24 between the first end 28 and the second end 30 of the base beam 16. In other embodiments, the base beam 16 may have a different shape cross-section and may be constructed from more than a single beam. The illustrative base beam 16 is formed from radiolucent materials but in other embodiments may be non-radiolucent.

The patient support 14 also includes a first adapter 21 and a second adapter 23 for mounting the patient support 14 to the foundation frame 12 as shown, for example, in FIG. 1. The first adapter 21 is coupled to the first end 28 of the base beam 16 and to the foundation frame 12. The second adapter 23 is coupled to the second end 30 of the base beam 16 and to the foundation frame 12. In the illustrative embodiment, the adapters 21, 23 are formed from non-radiolucent materials but in other embodiments may be radiolucent.

The leg support 18 of the illustrative embodiment has a first end 32 pivotably coupled to the base beam 16 and a second end 34 coupled to the guide 20 as shown in FIG. 1. The leg support 18 includes a leg support beam 36 and a platform 38. The leg support beam 36 is pivotably coupled to the jog 26 of the base beam 16 between the first section 22 and the second section 24 of the base beam 16. The leg support beam 36 is also received by the guide 20 at the second end 34 of the leg support 18. The platform 38 of the leg support 18 is coupled to the leg support beam 36 and extends out from the leg support beam 36. In the illustrative embodiment, the leg support 18 made from radiolucent materials but in other embodiments may be made from non-radiolucent materials.

Figure 2:
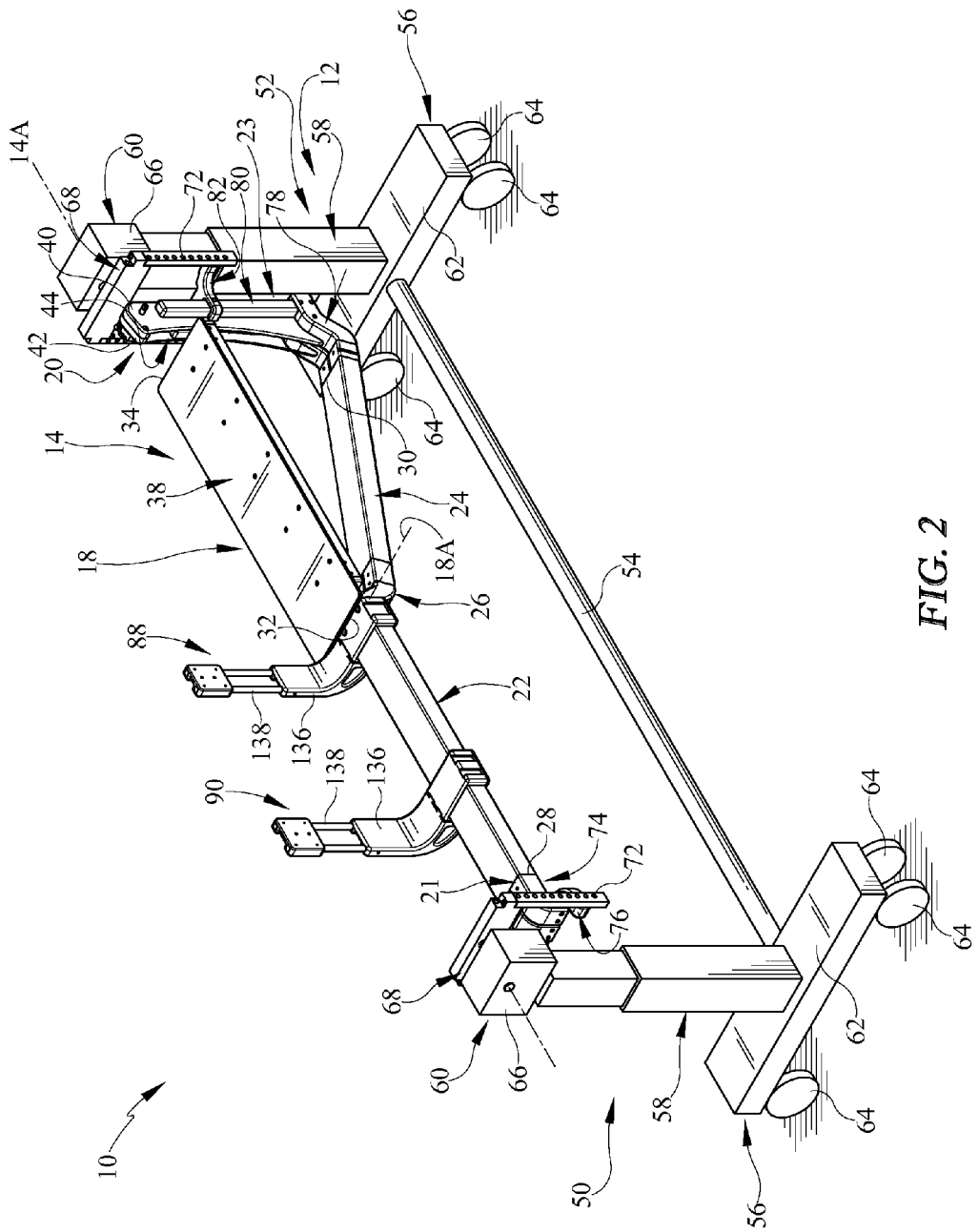
FIG. 2 is another perspective view of the surgical support of FIG. 1.
Figure 3:
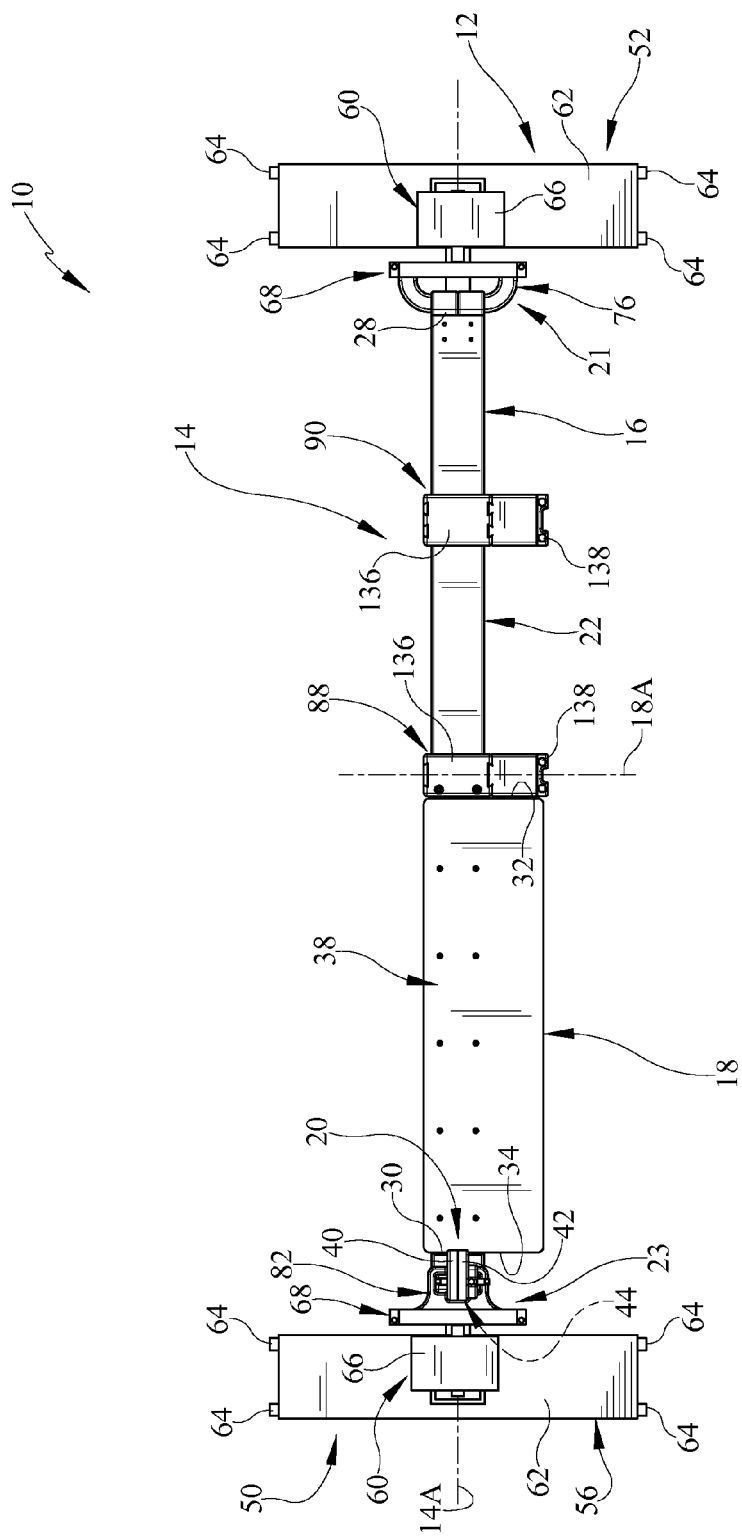
FIG. 3 is a top plan view of the surgical support of FIGS. 1 and 2.
Figure 4:
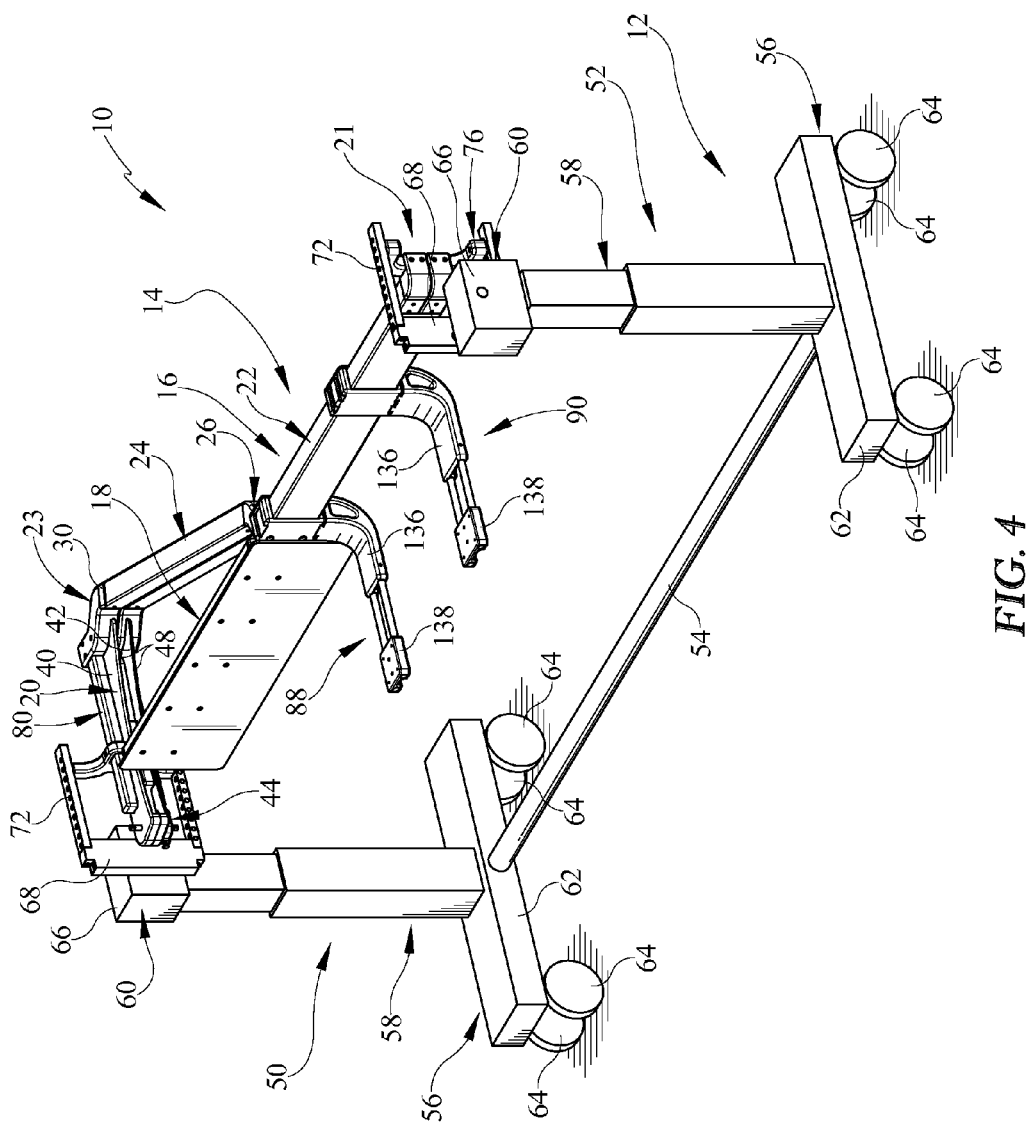
FIG. 4 is a view similar to FIG. 1 showing the patient support rearranged to support a patient in a prone (face down) or supine position (face up)
Figure 5:
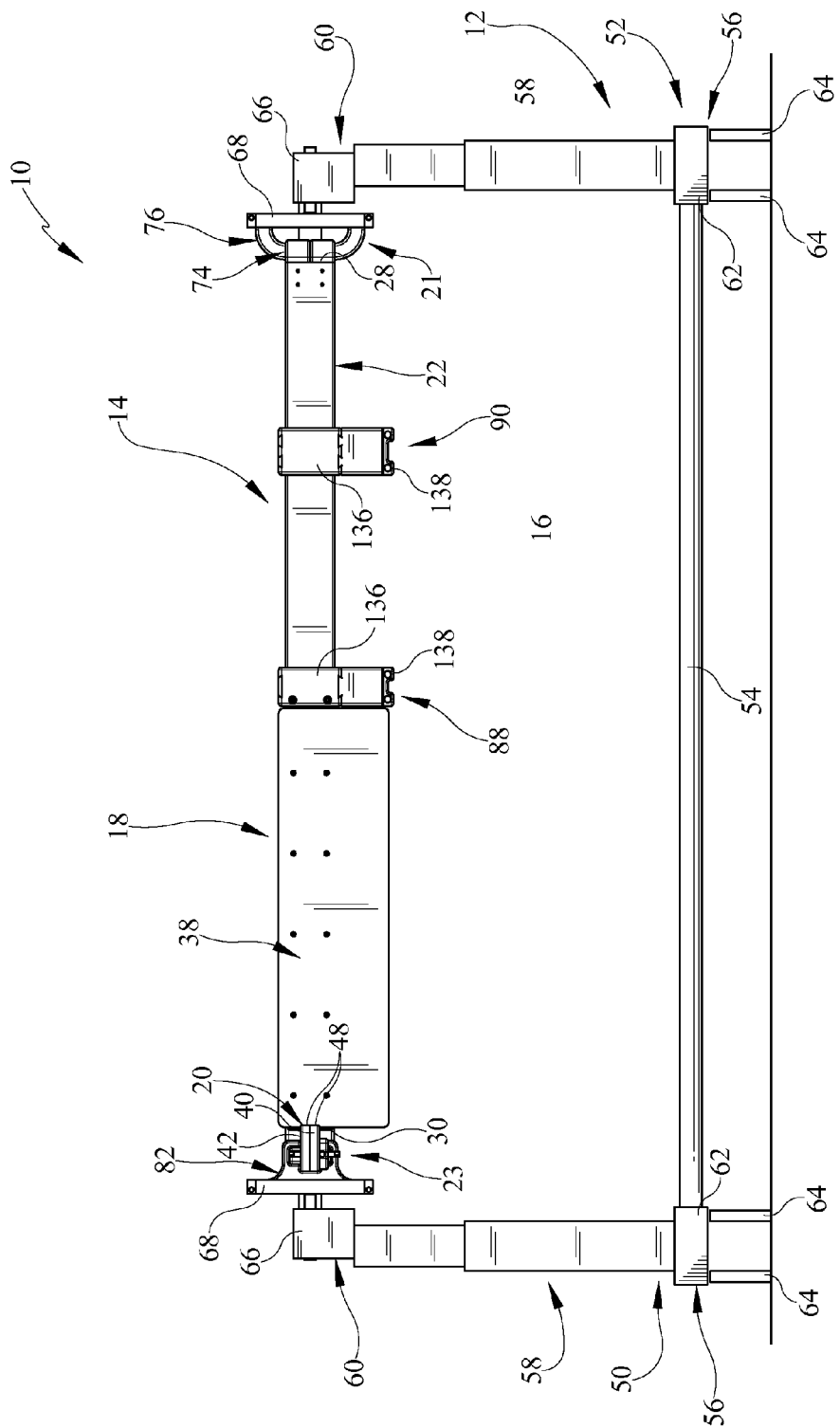
FIG. 5 is a left-side elevation view of the surgical support of FIG. 4.

The guide 20 or arch-like structure of the patient support 14 illustratively includes pair of plates 40, 42 and a drive 44 as shown in FIG. 2. The pair of plates 40, 42 form a track 46 that receives the leg support beam 36. Each plate 40, 42 extends up from the second adapter 23 and includes an arcuate edge 48 facing the leg support 18 and shaped to correspond to the path traveled by the second end 34 of the leg support 18 when the leg support is pivoted away from the horizontal position as shown, for example, in FIG. 8. The plates 40, 42 may be formed from radiolucent materials or, in other embodiments, may be non-radiolucent. The drive 44 is coupled to the leg support beam 36 inside the track 46 of the guide 20.

Figure 49:
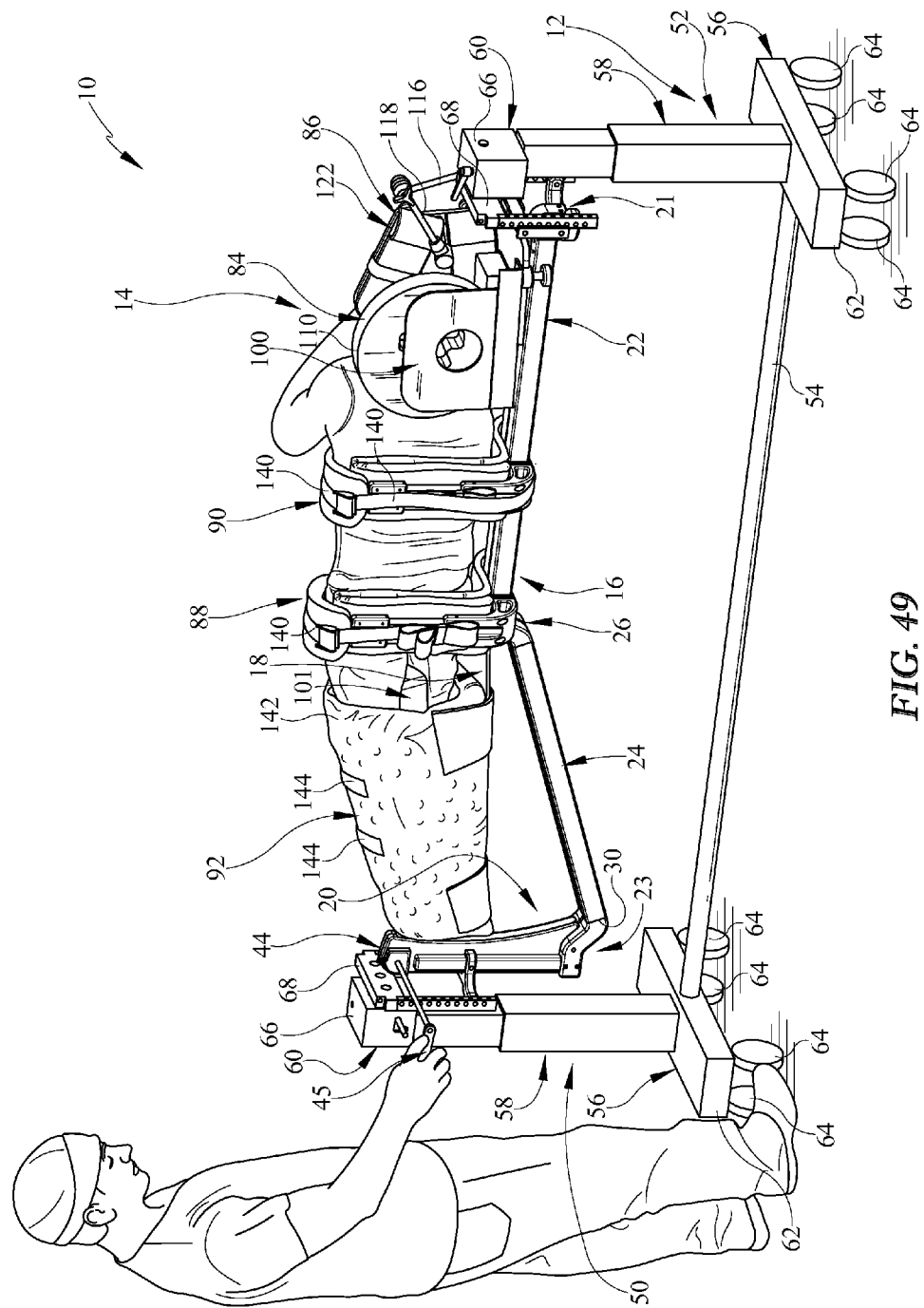
Figure 50:
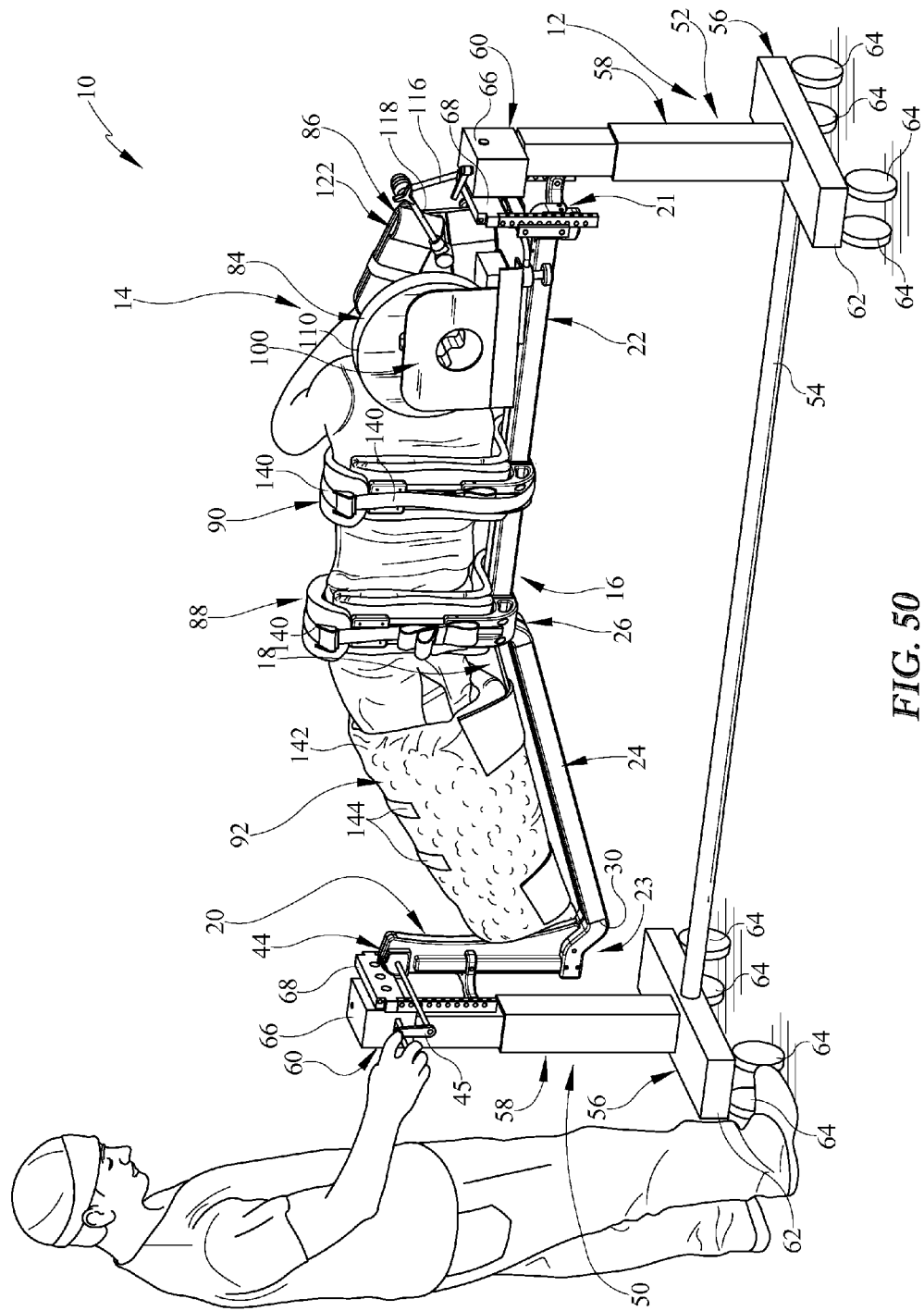

The drive 44 is operable to move the leg support 18 between the inclined, horizontal, and declined positions as shown in FIG. 8. The drive 44 may be a manual mechanical drive mechanism as shown, for example, in FIG. 48-50 or an electric motor. The drive 44 shown in FIGS. 48-50 illustratively includes a removable hand crank 45.

The foundation frame 12 illustratively includes a first mount 50, a second mount 52, and a connector beam 54 extending between the first mount and the second mount 52 as shown in FIG. 1. Each mount includes a carriage 56, a column 58, and a connector 60. Each carriage 56 includes a plate 62 and a number of casters 64. The plates 62 of each carriage 56 are coupled to opposite ends of the connector beam 54. Each column 58 is extendable and is coupled to one of the plates 62. Each connector 60 is configured to be coupled to the adapters 21, 23 of the patient support 14 so that the patient support 14 is mounted on the foundation frame 12.

Each connector 60 illustratively includes a bearing box 66, and a U-shaped connection frame 68 as shown in FIG. 1. The bearing boxes 66 are coupled to the columns 58 and are configured to support the connection frames 68 and the patient support 14 for rotation about the patient support axis 14A. The connection frames 68 are illustratively U-shaped and are formed to include a number of adapter holes 72 extending through the legs of the U-shaped connection frames 68.

The first adapter 21 of the patient support 14 is configured to releasably couple to a connection frame 68 of the foundation frame 12 as shown, for example, in FIG. 1. The first adapter 21 illustratively includes an elbow extension 74 and a yoke 76. The elbow extension 74 is L-shaped and is coupled to the first end 28 of the base beam 16. The yoke 76 is coupled to the elbow extension 74 and is configured to releasably engage the adapter holes 72 of one of the connection frames 68.

The second adapter 23 of the patient support 14 is configured to releasably couple to a connection frame 68 of the foundation frame 12 as shown, for example, in FIG. 1. The second adapter 23 illustratively includes an angled extension 78, a pair of rails 80 extending up from the angled extension 78, and a yoke 82. The angled extension 78 is illustratively S-shaped and is coupled to the second end 30 of the base beam 16. The rails 80 of the second adapter 23 are illustratively situated on opposing sides of the guide 20. The yoke 82 is coupled to the rails 80 and is configured to releasably engage the adapter holes 72 of one of the connection frames 68.

Figure 12:
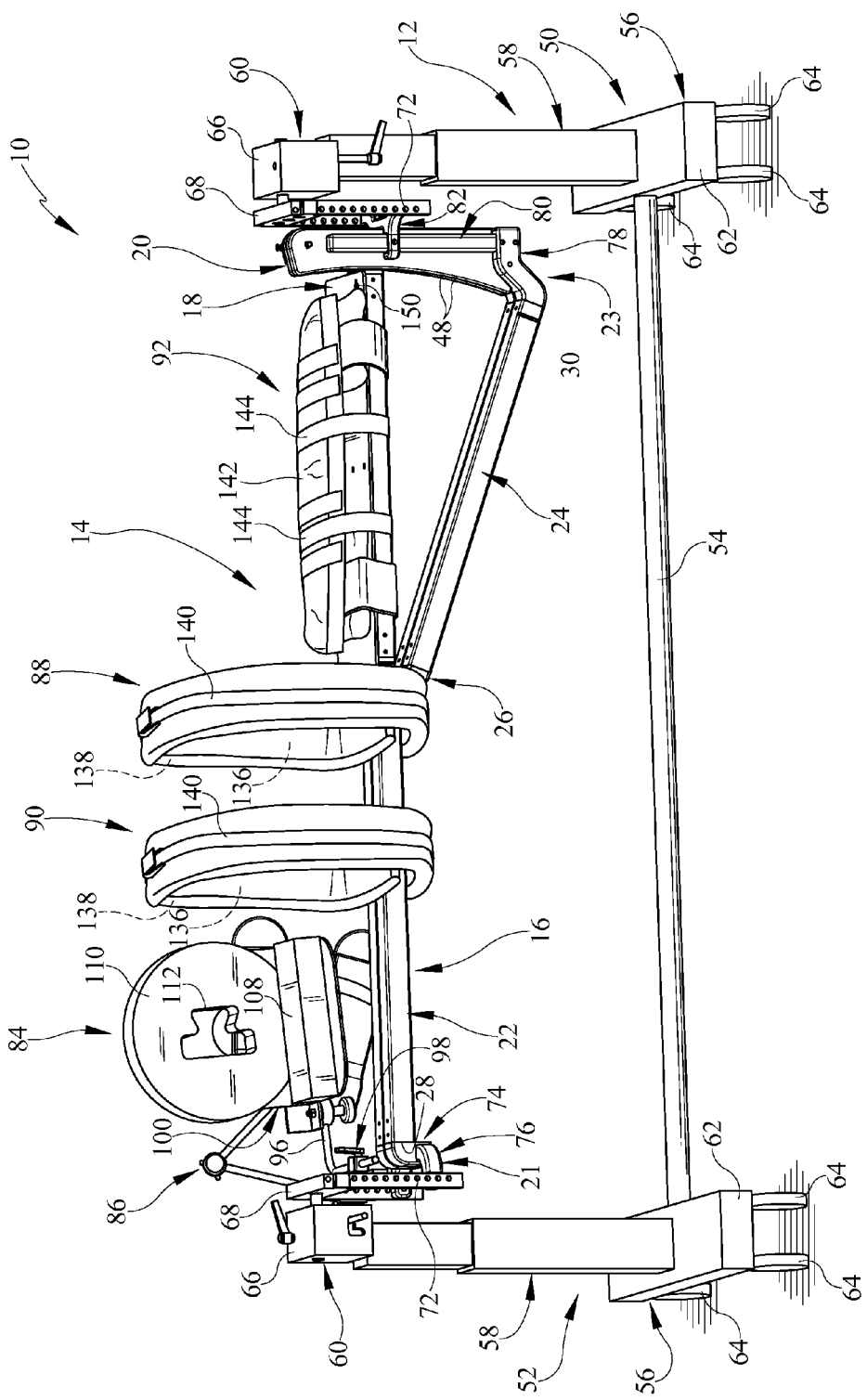
FIG. 12 is a perspective view of the surgical support of FIG. 1 showing that the surgical support may include an A-arm support and a head support, another embodiment of a torso support, and a leg-wrap support.
Figure 13:
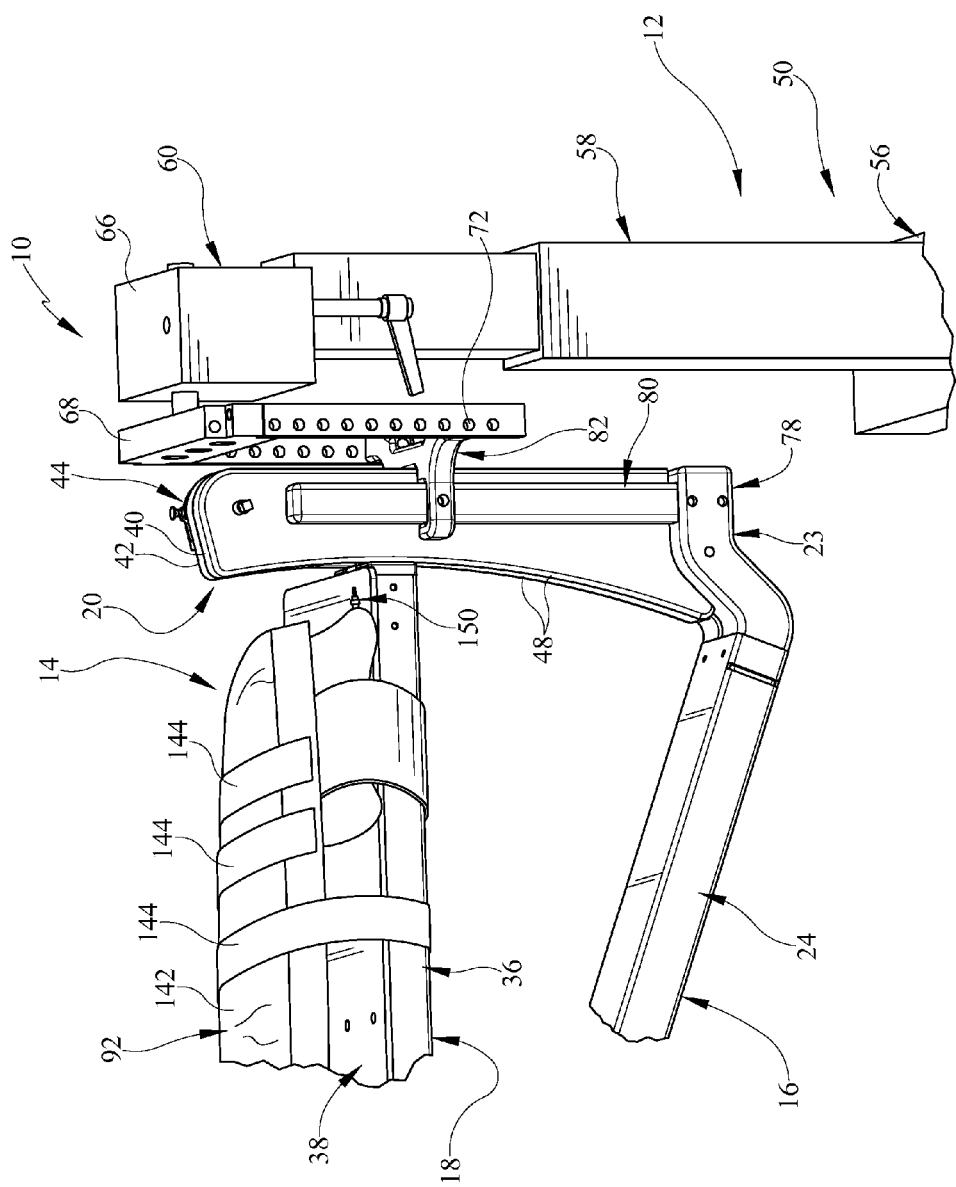
FIG. 13 is an enlarged partial perspective view of the patient support of FIG. 12 showing the guide included in the patient support.

The illustrative patient support 14 also includes a head support 84, an arm support 86, torso supports 88, 90, and a leg wrap support 92 as shown in FIG. 12. Each of the supports 84, 86, 88, 90, and 92 is configured to support the patient's head when the patient is supported in the lateral position and when the patient is rotated to the prone (or supine) position. The head support 84 is coupled to the connection frame 68 of the foundation frame 12 at the first end 28 of the base beam 16 and is configured to support the patient's head. The arm support 86 is coupled to the connection frame 68 of the foundation frame 12 at the first end 28 of the base beam 16 and is configured to support both of the patient's arms. The torso supports 88, 90 are coupled to the first section 22 of the base beam 16 and are configured to support the patient's torso. The leg wrap support 92 is coupled to the leg support 18 and is configured to hold the patient's legs in contact with the platform 38 of the leg support 18.

Figure 15:
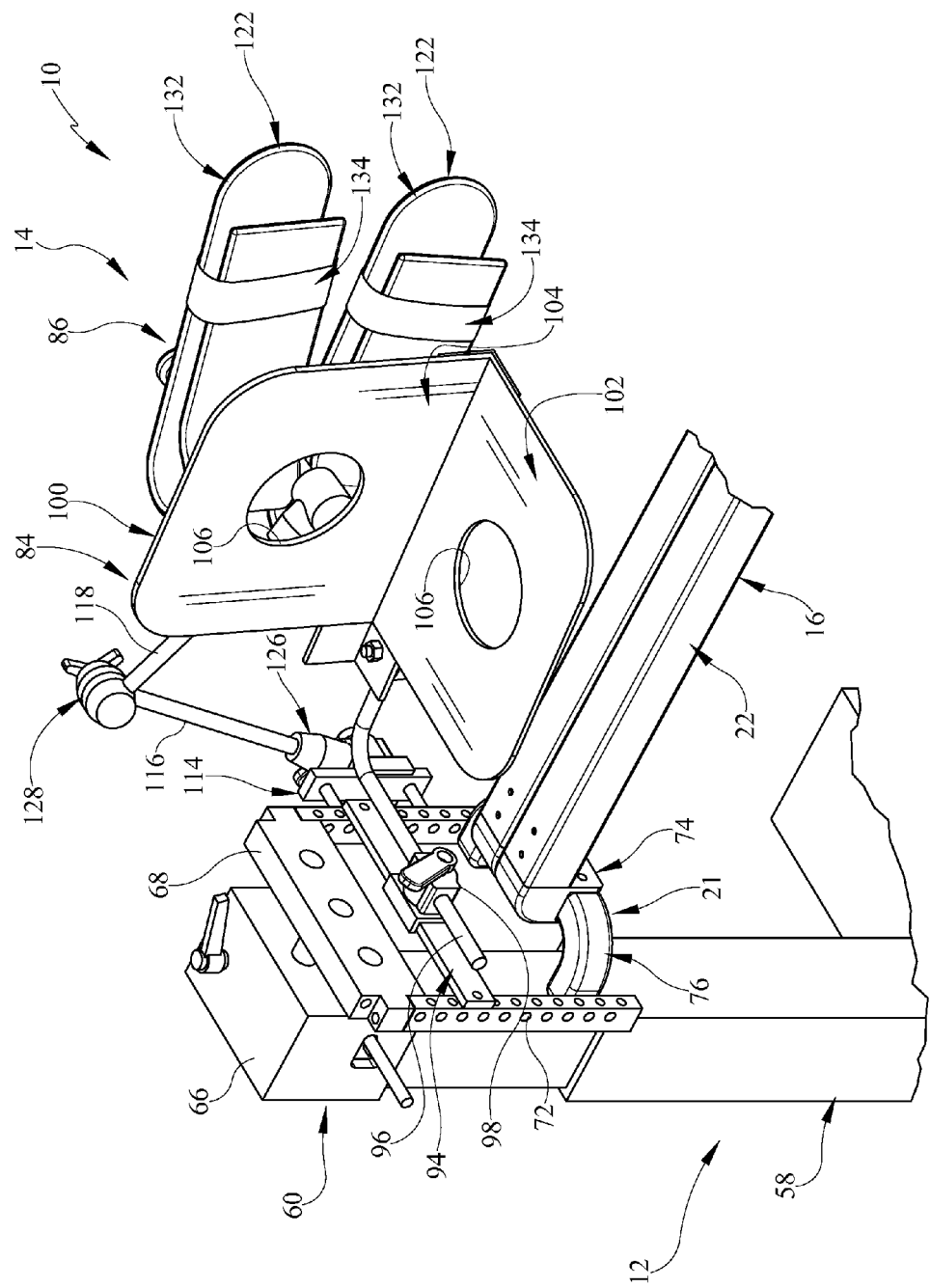
FIG. 15 is a partial perspective view of the surgical support of FIG. 12 showing the head support coupled to the patient support by the A-arm support to cause the head support to move with the base beam.

As shown in FIG. 15, the head support 84 includes a mount rail 94, a rod lock 96, a rod 98, and a head support bracket 100. The mount rail 94 is configured to be coupled to the connection frame 68 of the foundation frame 12. The rod lock 96 is coupled to the mount rail 94 and is configured to selectively allow the rod 98 to slide relative to the mount rail 94. The rod 98 is illustratively L-shaped and has a round cross-section. The head support bracket 100 is illustratively L-shaped and includes a lower plate 102 coupled to the rod 98 and an upper plate 104 extending at about 90 degrees from the lower plate 102. Each of the lower plate 102 and the upper plate 104 of the head support bracket 100 include a round hole 106 sized to provide an opening through which the patient's mouth and nose will be supported so that the patient can breathe when supported on the patient support 14.

Figure 16:
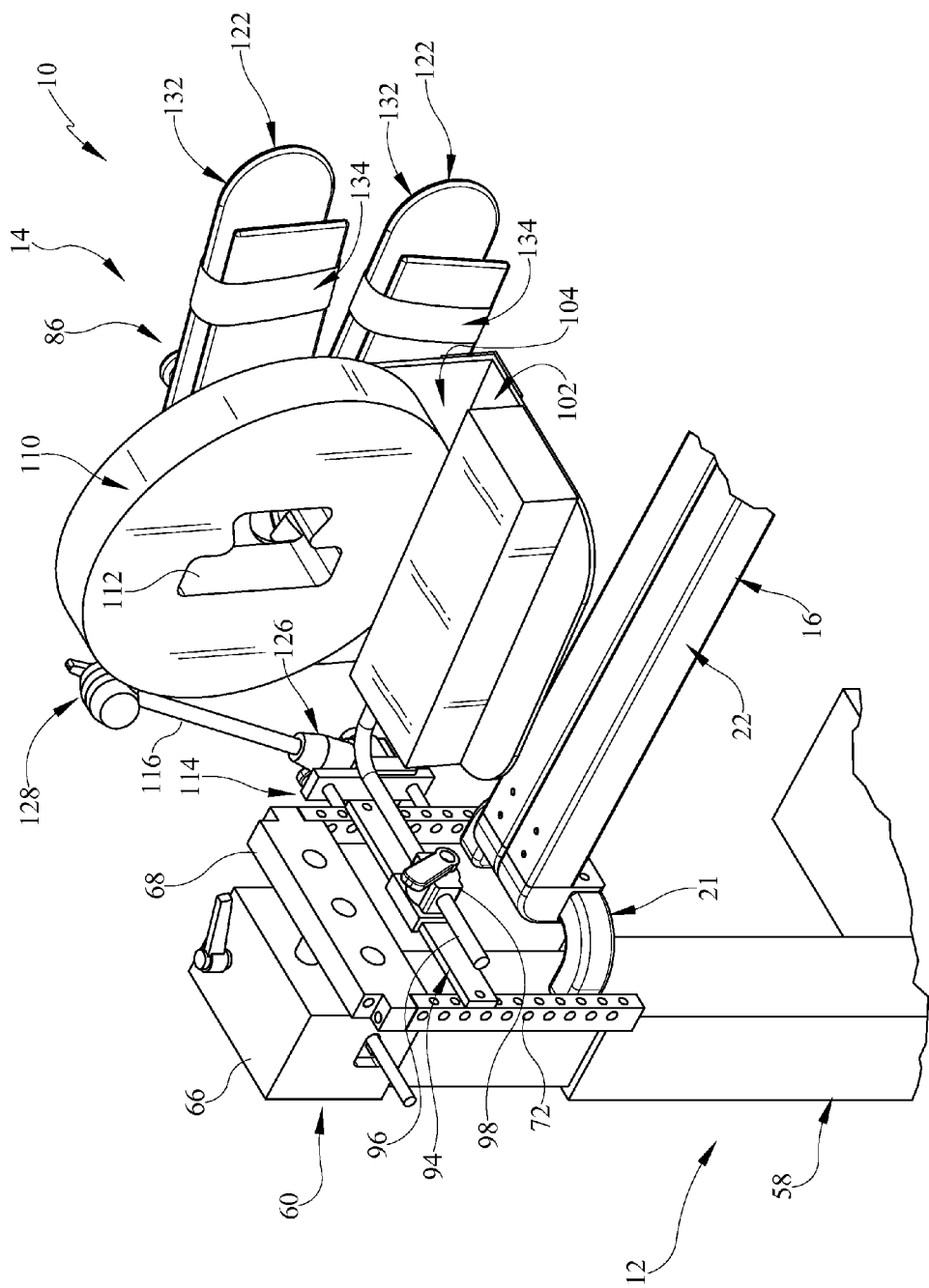
FIG. 16 is a view similar to FIG. 15 showing a support cushion coupled to the head support.

The head support 84 also includes a rectangular foam cushion 108 and a round foam cushion 110 as shown in FIG. 16. The rectangular foam cushion 108 is illustratively coupled to the lower plate 102 of the head support bracket 100. The round foam cushion 110 is illustratively coupled to the upper plate 104 of the head support bracket 100 and is formed to include an opening 112 near the center of the cushion 110 to allow the patient to breathe when supported face down on the round foam cushion. In other embodiments, the cushions 108, 110 may be other shapes. The foam cushions 108, 110 of the illustrative embodiment are disposable but in other embodiments may be reusable. In some embodiments, the head support 84 may also include a strap (not shown) configured to wrap around the patient's head to secure the patient's head to the head support bracket 100.

The arm support 86 illustratively includes a mount rail 114, a first support rod 116, a second support rod 118, an arm support bracket 120, and a pair of mitts 122, 124 as shown in FIG. 53. The mount rail 114 is configured to be coupled to the connection frame 68 of the foundation frame 12. The first support rod 116 is slidably coupled to the mount rail 114 by a first friction joint 126. The second support rod 118 is pivotably coupled to the first support rod 116 by a second friction joint 128. The arm support bracket 120 is pivotably coupled to the second support rod 118 by a third frictional joint 130, illustratively a ball joint. Each of the mitts 122, 124 are pivotably coupled to the arm support bracket 120 and illustratively includes a foam sleeve 132 and a number of straps 134 that wrap around the foam sleeves 132 to secure the patient's arms to the foam sleeves 132. The straps 134 are illustratively secured by hook and loop material attached to the straps. In other embodiments, other fasteners such as claps or hooks may be used to secure the straps 134. The mitts 122, 124 of the illustrative embodiment are disposable but in other embodiments may be reusable.

Figure 14:
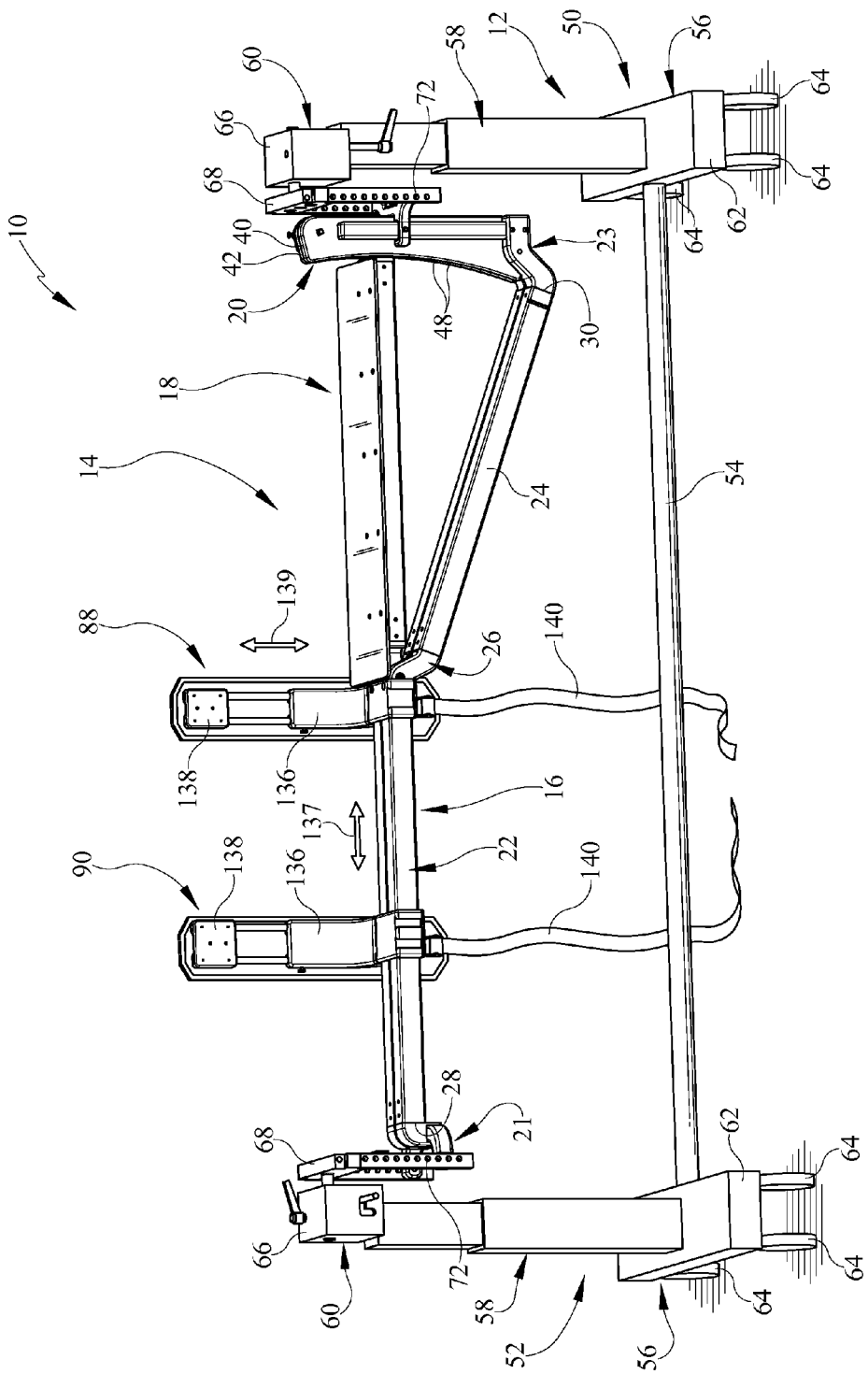
FIG. 14 is another perspective view of the surgical support of FIGS. 1 and 2.

The torso supports 88, 90 are illustratively radiolucent and are slidably coupled to the first section 22 of the base beam 16 and are located to support the patient's torso as shown in FIG. 14. Each torso support 88, 90 includes an L-shaped bracket 136, an extension 138, and a strap 140. The L-shaped bracket 136 is slidably coupled to move along the first section 22 of the base beam 16 as suggested by arrow 137 in FIG. 14. By sliding the L-shaped brackets 136 along the base beam 16, a caregiver can arrange the torso supports 88, 90 so that the patient is supported at the chest and the hips such that the patient's abdomen is free to hang down during a surgery when the patient is supported in the prone position as shown in FIG. 39. The extensions 138 are movable relative to the L-shaped bracket 136 as suggested by arrow 139 in FIG. 14 to extend or retract the torso supports 88, 90 to accommodate different sized patients. The straps 140 are coupled to the L-shaped brackets 136 and are configured to wrap around the patient to secure the patient to the torso supports 88, 90. The straps 140 are illustratively secured by hook and loop material attached to the straps. In other embodiments, other fasteners such as claps or hooks may be used to secure the straps 140. In other embodiments, the torso supports 88, 90 may be non-radiolucent.

The leg wrap support 92 illustratively includes a vacuum bag 142 and a number of straps 144. The vacuum bag 142 is coupled to the leg support 18 by a pair of bands 146 and is illustratively sized to extend over substantially all of the patient's legs. The straps 144 are coupled to the vacuum bag 142 and are configured to be wrapped around the vacuum bag 142 and the patient's legs in order to temporarily secure the vacuum bag 142 around the patient's legs. The vacuum bag 142 is illustratively rectangular but in other embodiments could be another shape.

Figure 19:
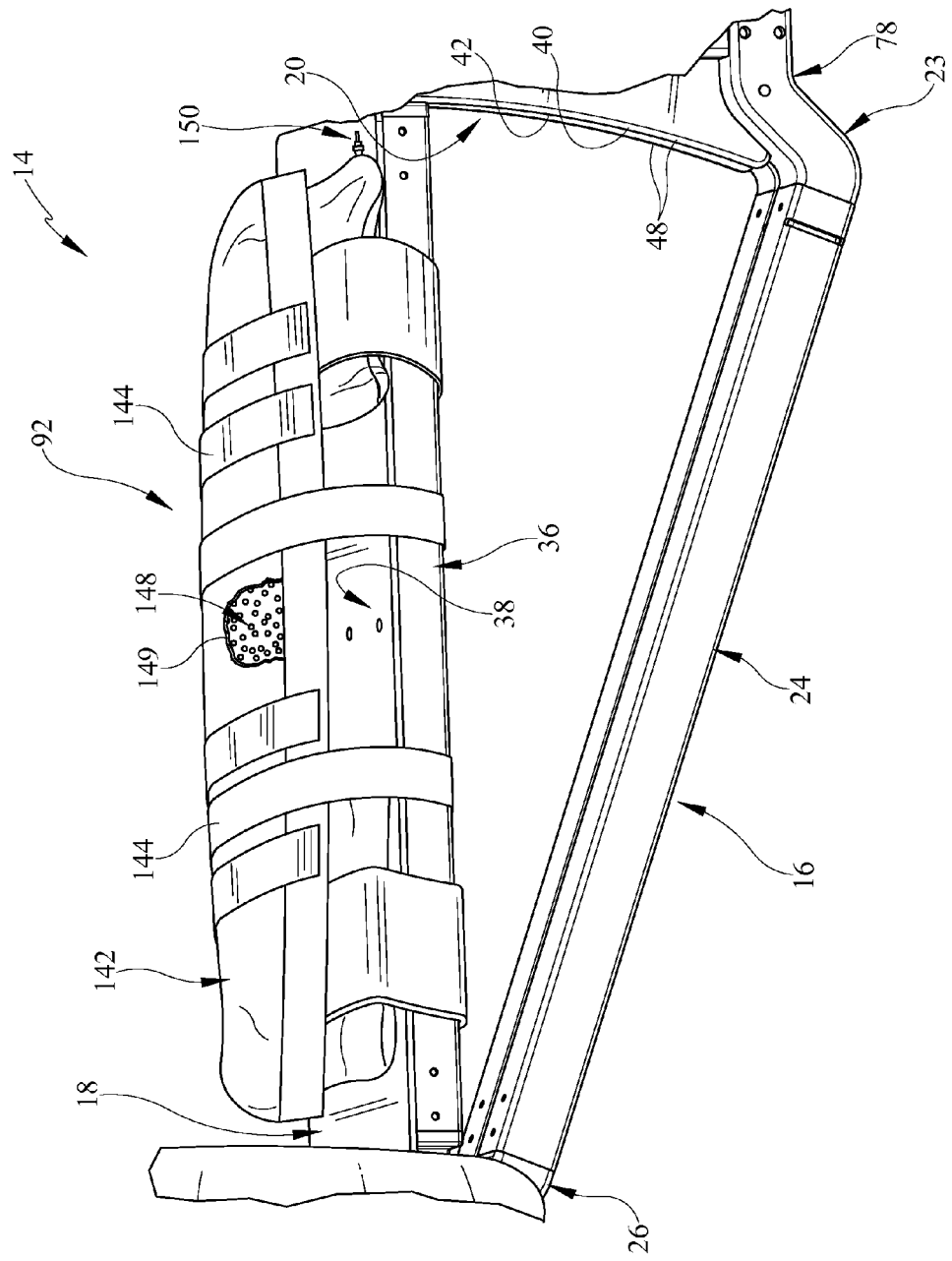
FIG. 19 is an enlarged partial perspective view showing the leg-wrap support coupled to the leg support.
Figure 20:
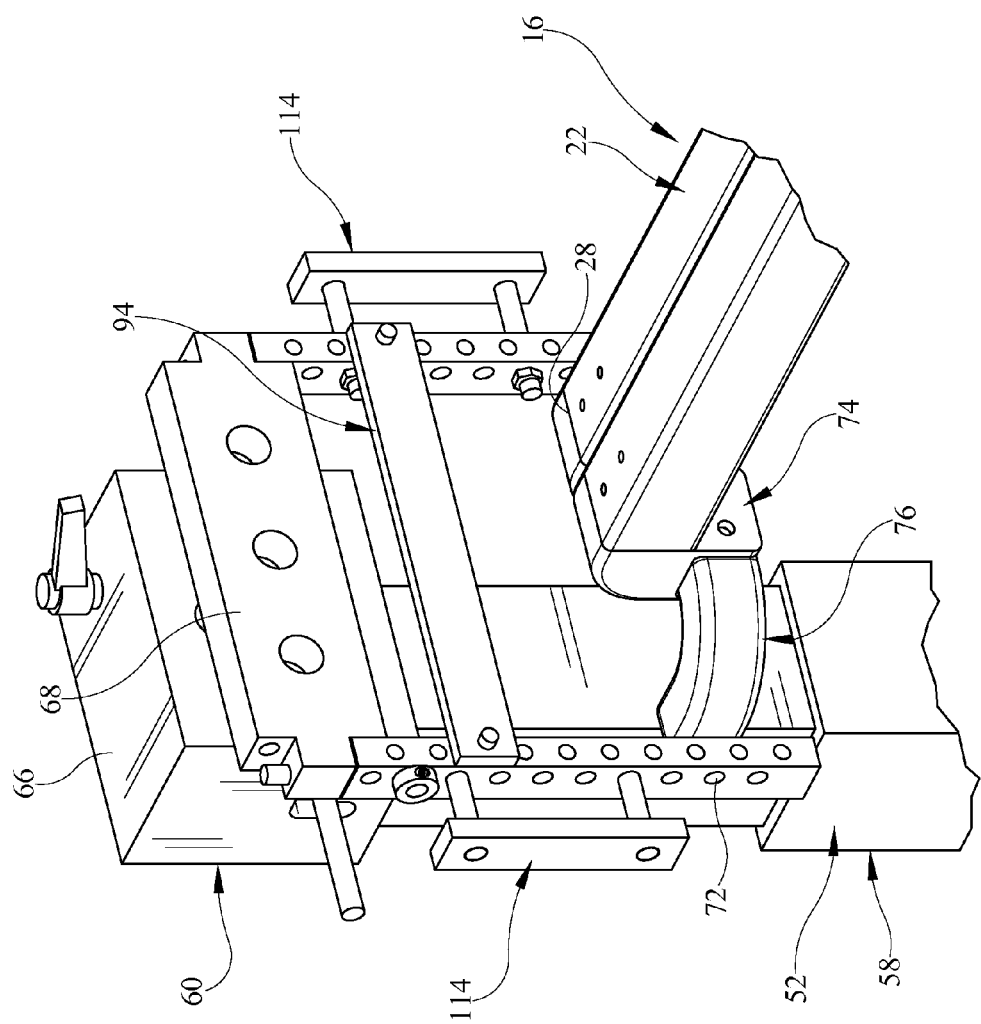
FIG. 20 is an enlarged partial perspective view showing an adapter included in the patient support that interconnects the base beam to the foundation frame.
Figure 21A:
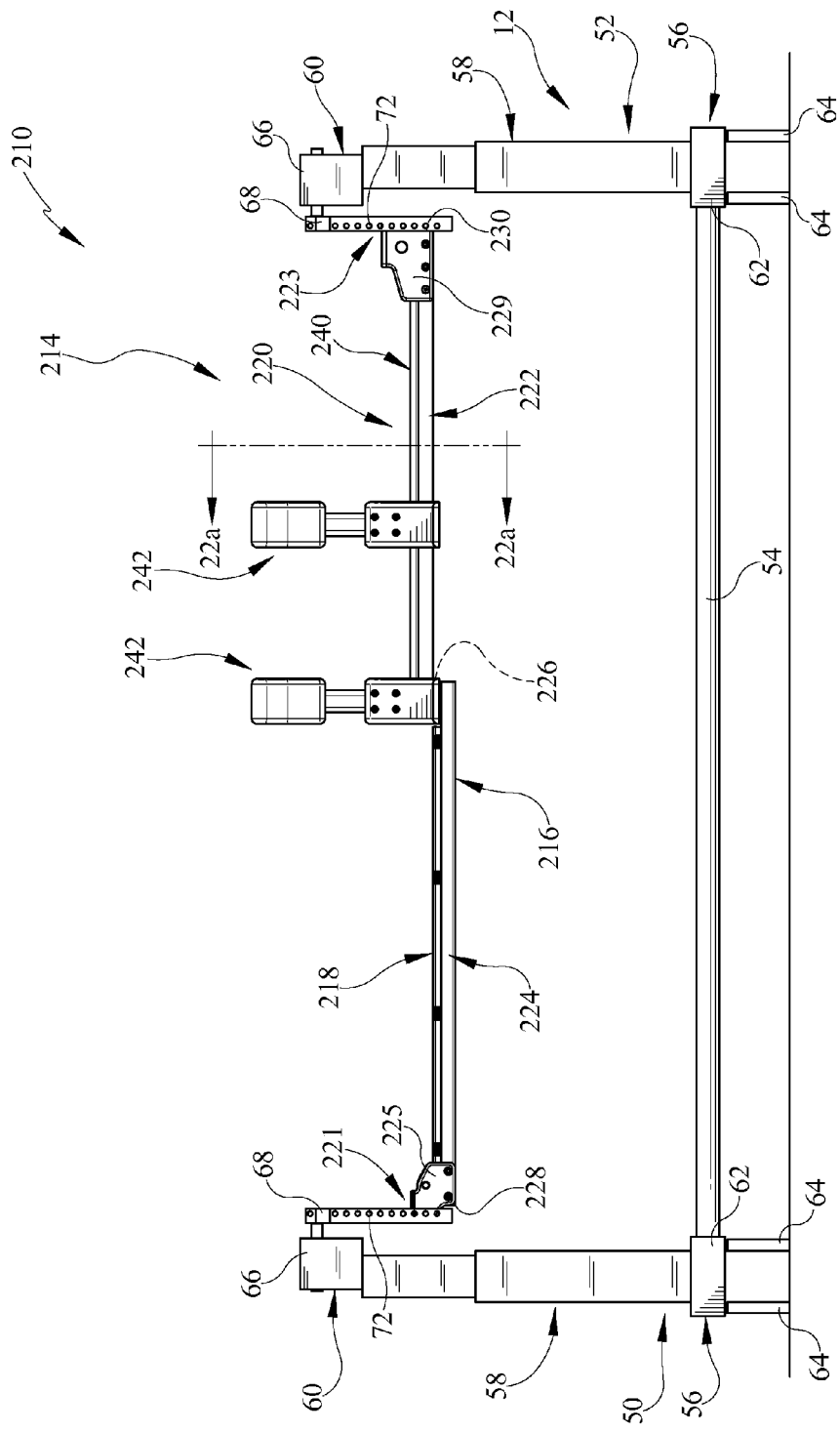
FIG. 21a is a left-side elevation view of another embodiment of a surgical support in accordance with the present disclosure showing the foundation frame and a patient support arranged to support a patient in a lateral position as suggested in FIG. 21b.
Figure 21B:
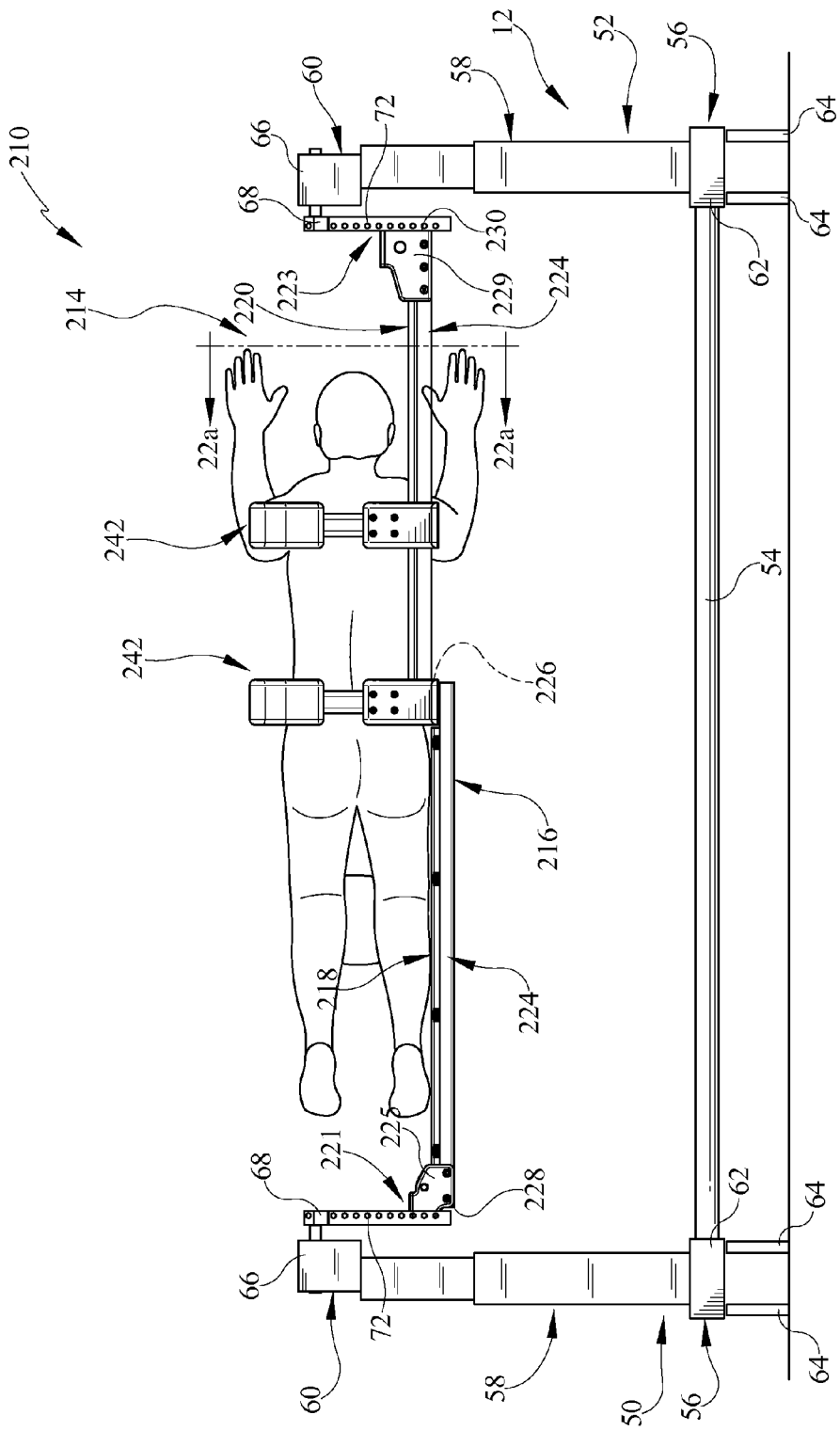
FIG. 21b is a view similar to FIG. 21a showing a patient resting on the patient support in the lateral position.
Figure 22A:
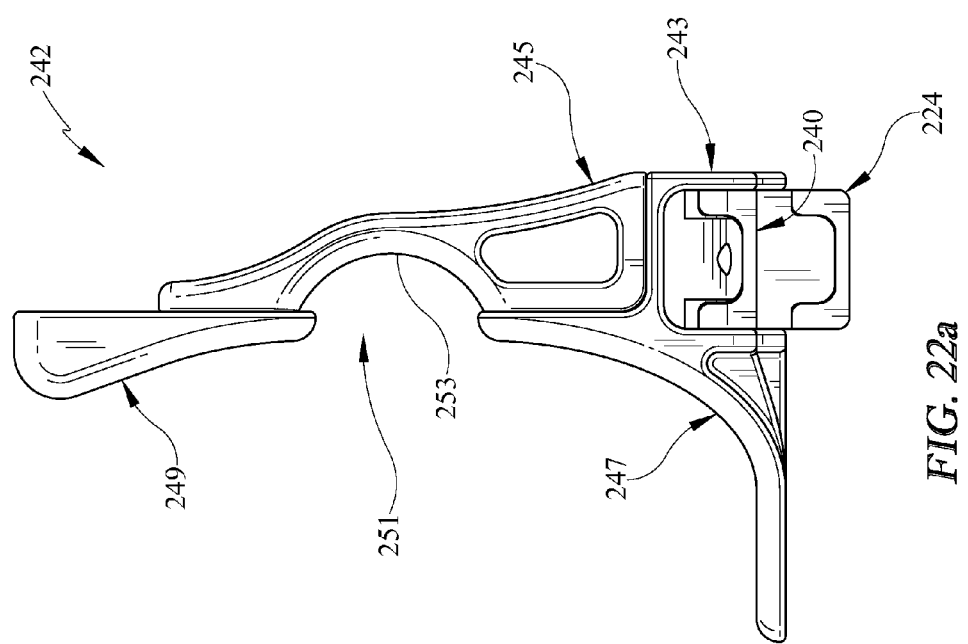
FIG. 22a is a partial head-end elevation view of the patient support of FIG. 21a showing the torso-support member of FIG. 18 coupled to a base beam included in the patient support.
Figure 22B:
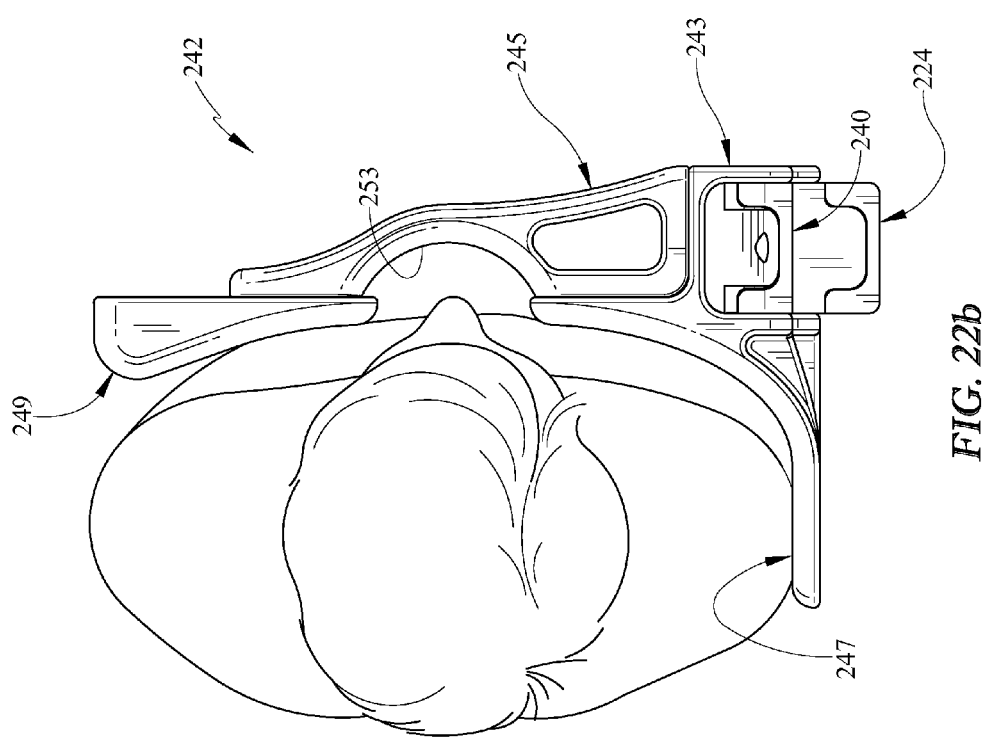
FIG. 22b is a partial head-end elevation view of the patient support of FIG. 21b showing engagement of the patient with the torso-support member.

The vacuum bag 142 illustratively contains a number of beads 148, an overlay layer 149, and a valve 150 as shown in FIG. 19. When the vacuum bag 142 is wrapped around the patient's legs, the air inside the vacuum bag 142 may be evacuated from the vacuum bag 142 by an external vacuum source 111 through the valve 150. When the air is evacuated, the beads 148 inside the vacuum bag 142 are compacted and the leg wrap support 92 becomes inflexible so that the patient's legs are secured to the leg support 18 and are immobilized. The overlay layer 149 extends over the outer surface of the vacuum bag 142 and cushions the patient's legs when the leg wrap support 92 is inflexible. The overlay layer 149 may be gel, foam, or a combination of gel and foam.

Figure 17A:
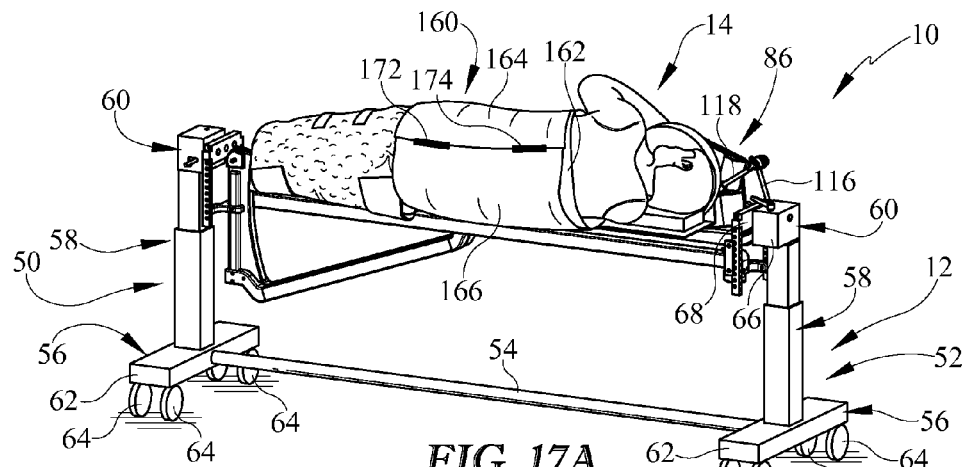
FIGS. 17A-17C show an illustrative drape process used with the surgical support of FIG. 12.
Figure 17B:
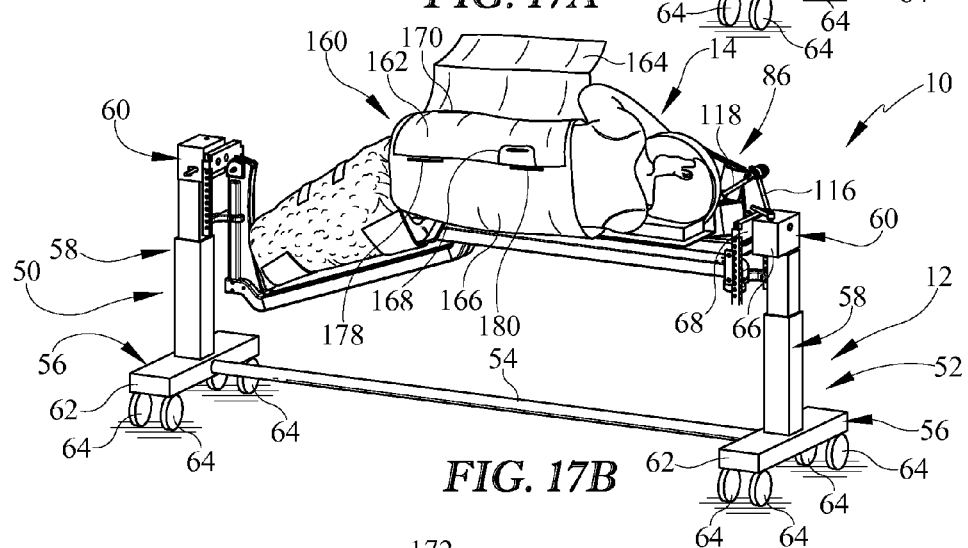
Figure 17C:
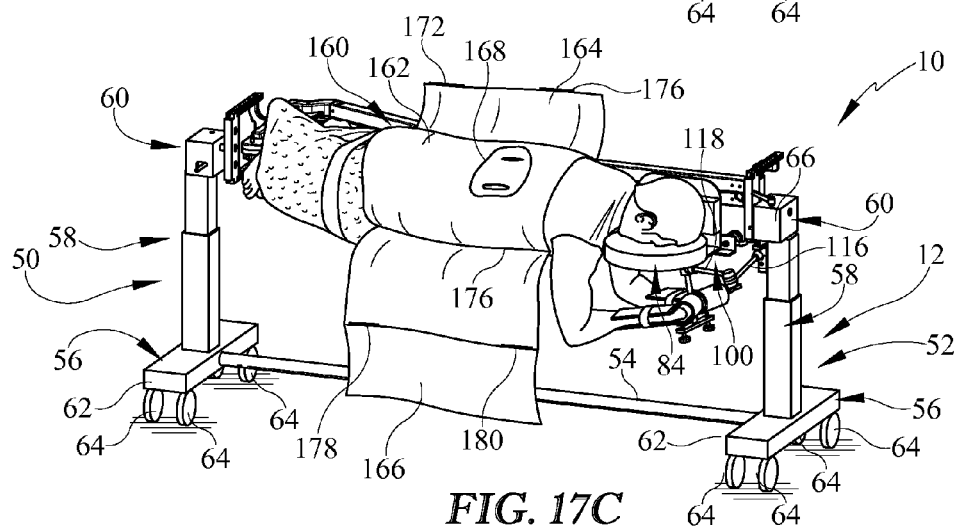
Figure 18:
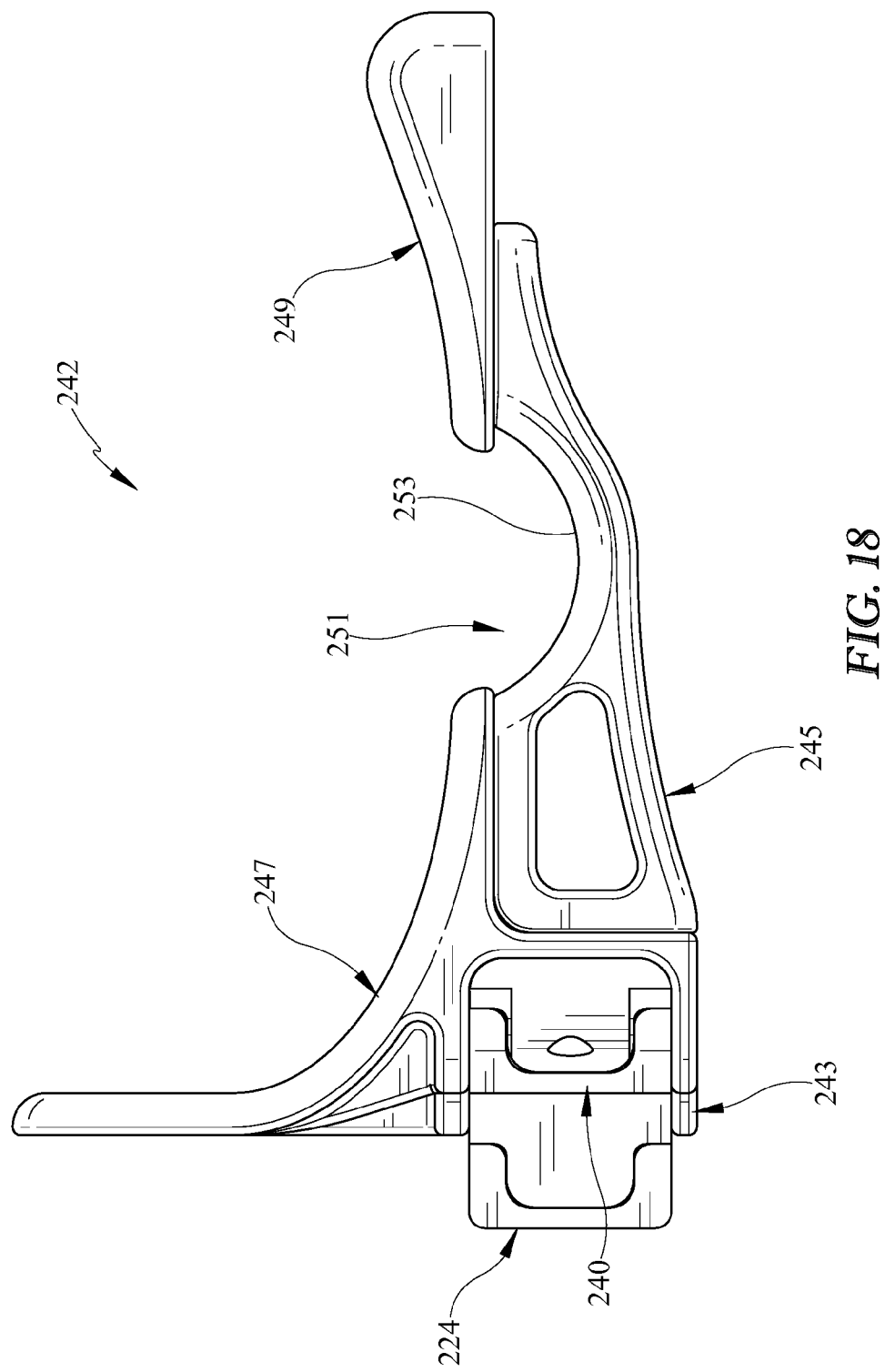
FIG. 18 is partial elevation view of another embodiment of a torso-support member in accordance with the present disclosure that may be used with or in place of the first and second torso supports of FIGS. 1-6, 8-12, and 14 and showing where the patient's center of gravity (double phantom arrow) is located relative to the torso-support member.

In some embodiments, the patient support 214 may be used with a surgical drape 160 shown in FIGS. 17A-17C. The surgical drape 160 includes a base sheet 162, a first tear-away sheet 164, and a second tear-away sheet 166 as shown in FIG. 17C. The base sheet 162 is formed to include an opening 168 as shown, for example, in FIG. 17C. The first tear-away sheet 164 extends from a top edge 170 of the base sheet and is folded over the base sheet 162 to cover the top half of the opening 168. The first tear-away sheet 164 is secured in position over the top half of the opening 168 by strips of adhesive 172, 174 applied on either side of the opening 168. The second tear-away sheet 166 extends from a bottom edge 176 of the base sheet and is folded over the base sheet 162 to cover the bottom half of the opening 168. The second tear-away sheet 166 is secured in position over the bottom half of the opening 168 by strips of adhesive 178, 180 applied on either side of the opening 168. In other embodiments, the opening may be a pair of openings corresponding to the top half and the bottom half of the opening 168 in the base sheet 162. In some embodiments, light stitching or other break-away means may be used instead of adhesive.

A method of use of the surgical drape 160 may include the steps of (i) wrapping the drape around a patient, (ii) breaking the bond of the first tear-away sheet 164, (iii) pulling the first tear-away sheet 164 away from the base sheet 162 to expose the top half of the opening 168 thereby accessing a first surgical site, (iv) breaking the bond of the second tear-away sheet 166, and (v) pulling the second tear-away sheet 166 away from the base sheet 162 to expose the bottom half of the opening 168 thereby accessing a second surgical site. Specifically, in the illustrative embodiment, the surgical drape 160 is wrapped around the patient so that the top half of the opening 168 is positioned over a patient's side abdomen and the bottom half of the opening is positioned over the patient's back. Steps (ii) and (iii) may be performed while the patient is supported in a lateral position on the patient support 14 and subjected to lateral flexion as shown in FIG. 17B. Steps (iv) and (v) may be performed after a caregiver rotates the patient support 14 about the axis 14A relative to the foundation frame 12 so that the patient is supported in the prone position as shown in FIG. 17C. Thus, during a two-site surgery such as an XLIF/DLIF only a single surgical drape may be used. Other methods of using the surgical drape 160 with the surgical support 10 may be used where accessing two different surgical sites while the patient is in two different positions is desirable.

Another illustrative surgical support 210 is shown in FIGS. 21a-27b. The surgical support 210 includes a foundation frame 12 and a patient support 14 mounted on the foundation frame 12. The foundation frame 12 is illustratively a "Jackson Table" as described with regard to the surgical support 10 described above and similar reference numbers indicate similar components. The patient support 214 is coupled to the foundation frame 12 for pivotable movement about an axis 214A parallel to the length of the patient support 214 so that a patient supported on the surgical support 10 can be repositioned during a surgical procedure By pivoting the patient support 214 about the axis 214A, the patient supported on the patient support 214 can be moved between a lateral (or side-lying) position, as shown for example in FIG. 21b, and a prone (or face-down) position, shown in FIG. 26b. Alternatively, the patient supported on the patient support 14 can be moved between a lateral position and a supine (or face-up) position. Moving a patient between the lateral position and the prone/supine position during a surgical procedure may be undertaken in a number of medical procedures to increase accessibility of different parts of the patient's anatomy during different parts of a procedure. For example, during an extreme (or direct) lateral interbody fusion (XLIF/DLIF), a surgeon may access the patient's spine while the patient is in the lateral position to place a spinal implant and then move the patient to the prone position to place screws, plates, rods, and the like to secure the implant.

The patient support 214 illustratively includes a base beam 216, a leg support 218, and a torso support 220 as shown 21a. The base beam 216 includes a first section 222 underlying the torso support 220 and a second section 224 underlying the leg support 218. The leg support 218 is configured to support the patient's legs and is pivotably coupled to an end 228 of the base beam 216. The leg support 218 is movable between a horizontal position that is substantially parallel to the base beam 216 (shown in FIG. 21a) and a number of inclined positions forming an angle α with the base beam 216. The torso support 220 is configured to support the patient's torso and is pivotably coupled to an end 230, opposite the end 228, of the base beam 216 (shown in FIG. 24). The torso support 220 is movable between a horizontal position that is substantially parallel to the base beam 216 (shown in FIG. 21a) and a number of inclined positions forming an angle β with the base beam 216 (shown in FIG. 24). The base beam 216, leg support 218, and torso support 220 are made from radiolucent materials. In other embodiments, the base beam 216, leg support 218, and torso support 220 are non-radiolucent.

Figure 23A:
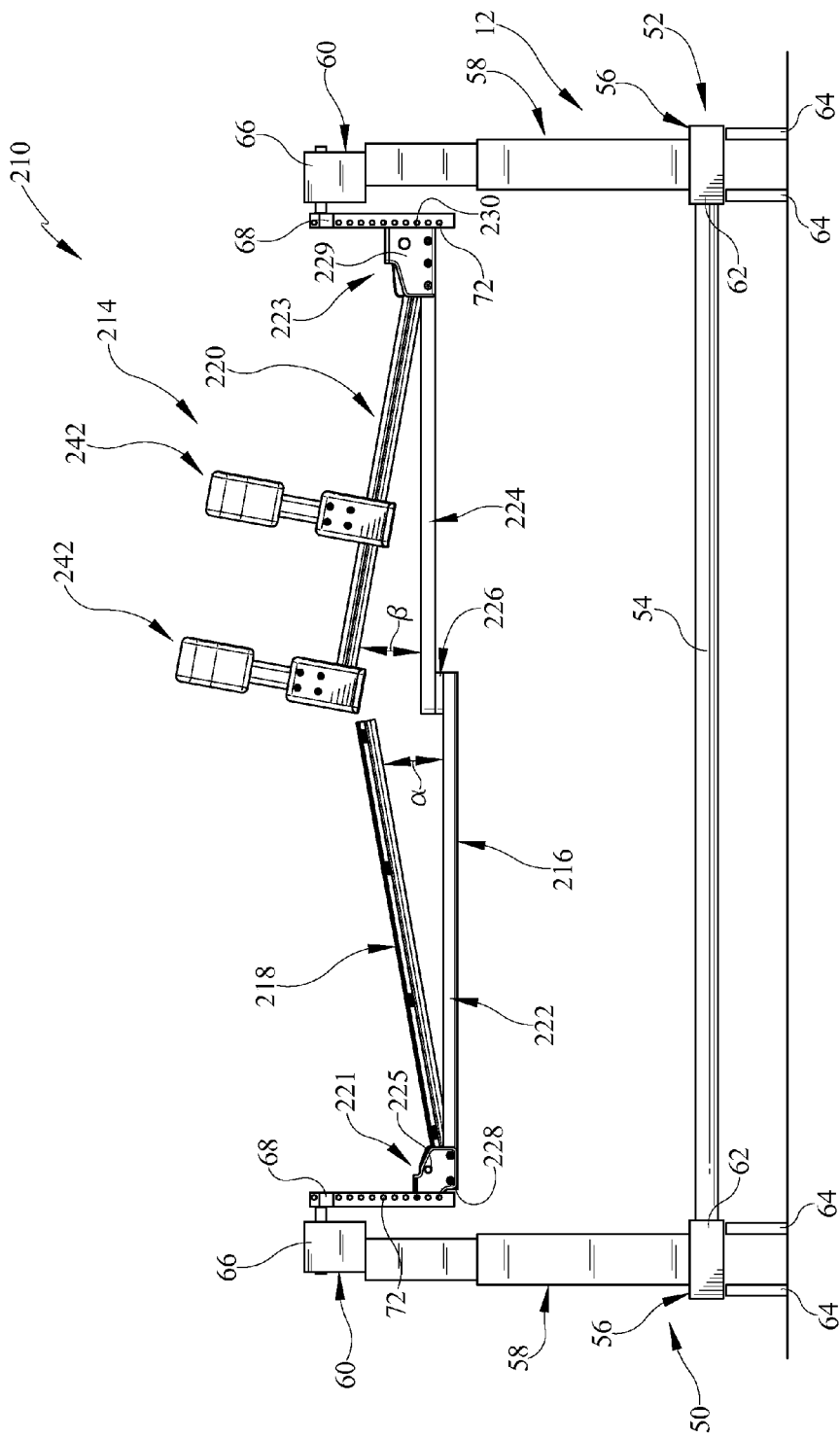
FIG. 23a is a view similar to FIG. 21a showing the patient support arranged in to support a patient in a lateral-flexion position as suggested in FIG. 23b.
Figure 23B:
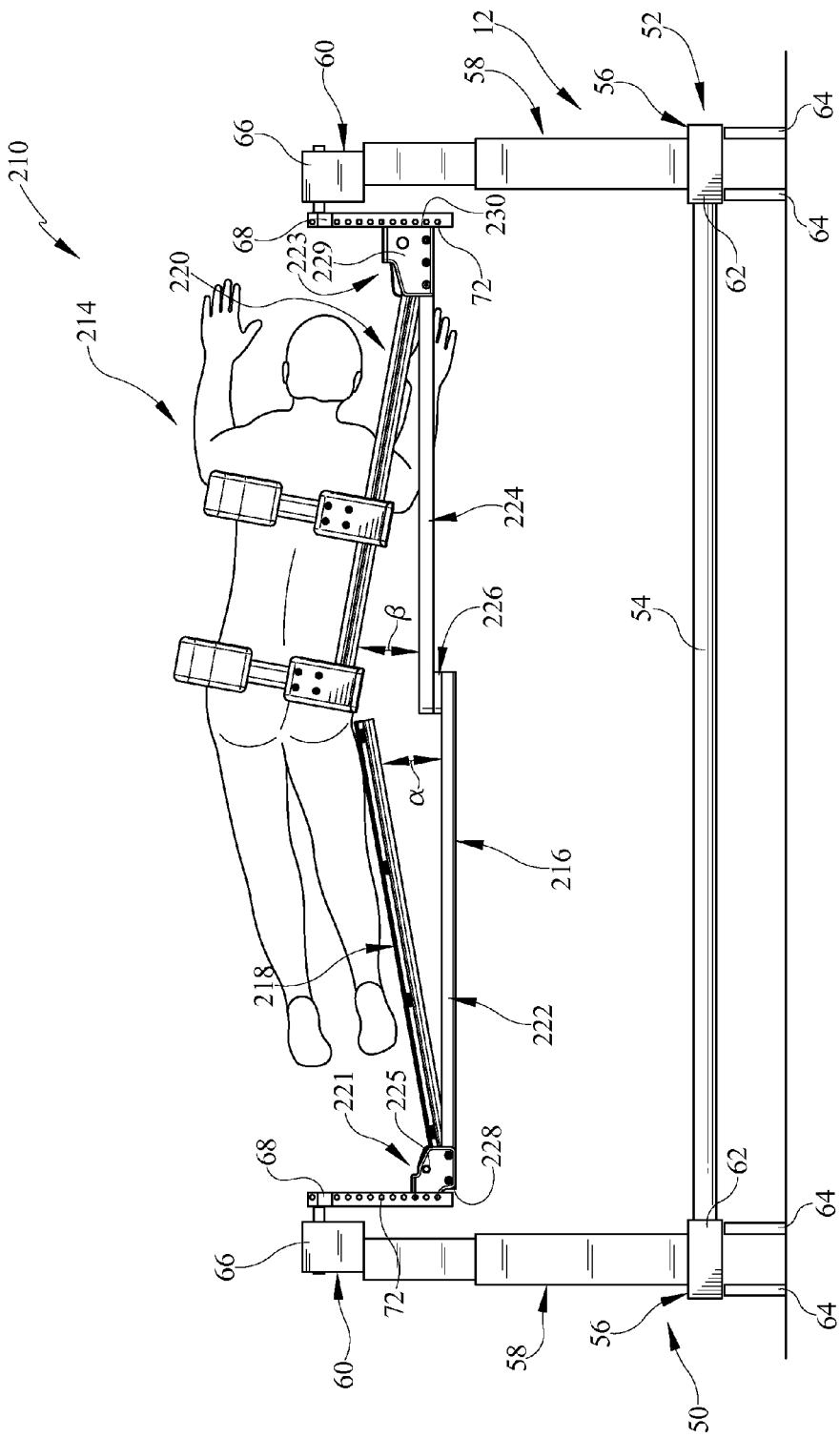
FIG. 23b is a view similar to FIG. 23a showing a patient resting on the patient support in the lateral-flexion position.

As shown in FIG. 23b, inclining the leg support 218 and the torso support 220 relative to the base beam 216 causes the leg support 218 and the torso support 220 to be spaced apart from the base beam near the middle of the patient support 214. Thus, a patient supported on the patient support 214 is moved into lateral flexion wherein the patient's torso is angled relative to the patient's legs. When the patient is subjected to lateral flexion, the patient's pelvis is moved away from the patient's rib cage along the side of the patient spaced apart from the base beam 216 and the leg support 218. Space between the patient's pelvis and rib cage may allow a surgeon to access portions of the patient's anatomy such as the spine (especially the lower vertebrae) and kidneys, through the patient's side. In one example, a surgeon may access the patient's spine from the side during an XLIF/DLIF procedure when the surgeon is placing a spinal implant.

Figure 24:
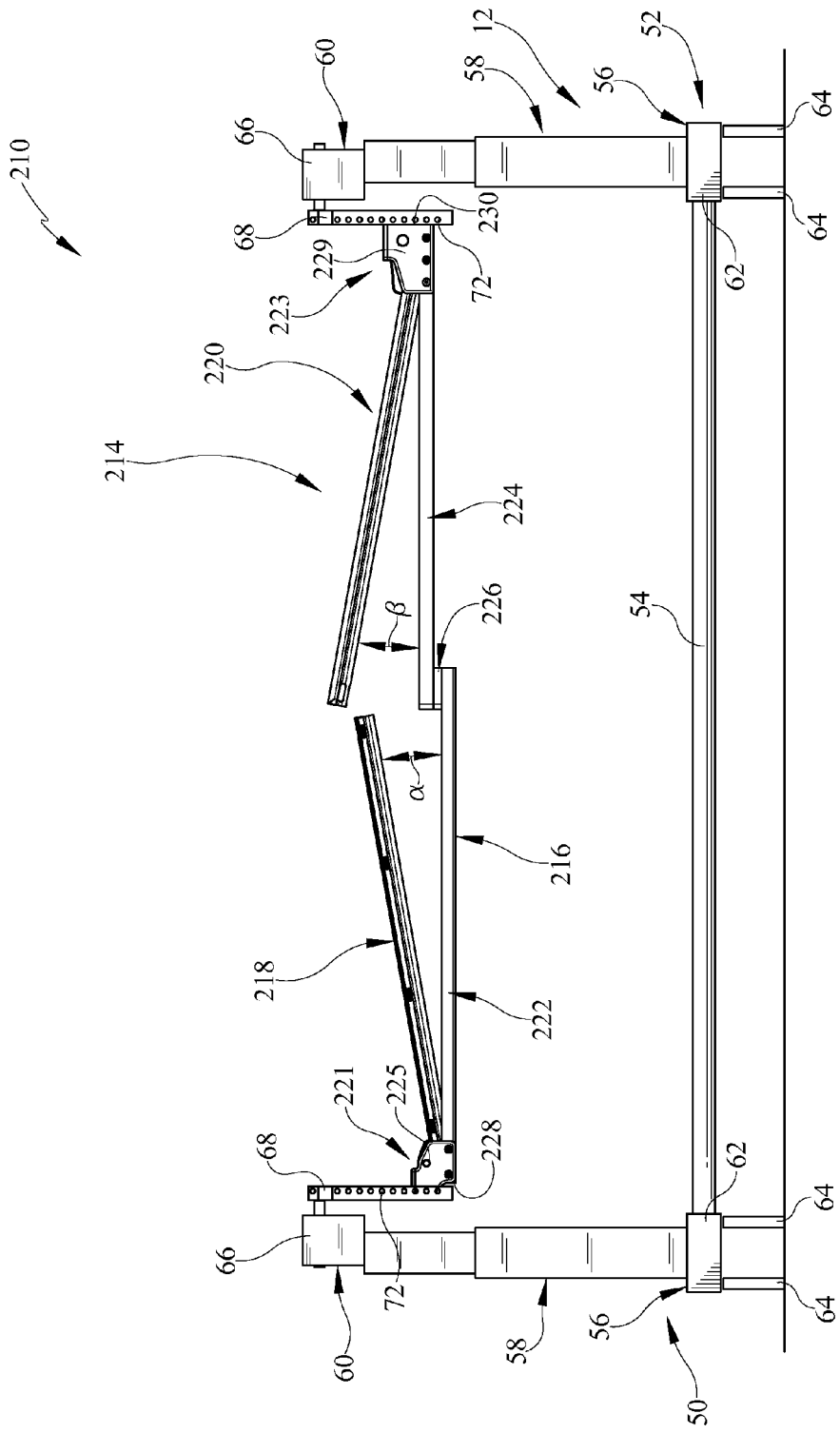
FIG. 24 is a view similar to FIGS. 23a and 23b showing the patient support with the first and second torso-support members removed from the base beam, the leg support moved to an inclined position in which an angle α is established between the base beam and the leg support and the torso support moved to an inclined position in which an angle β is established between the base beam and the torso support.

The base beam 216 illustratively has a C-shaped cross-section and includes the first section 222, the second section 224, and a step block 226 as shown, for example, in FIG. 24. The first section 222 forms the first end 228 of the base beam 216. The second section 224 forms the second end 230 is stepped down from the first section 222 and is substantially parallel to the first section 222. The step block 226 is coupled between the first section 222 and the second section 224 so that the first section 222 is stepped down from the second section 224. In other embodiments, the base beam 216 may have another shape cross-section and may be formed from a single component.

Figure 25:
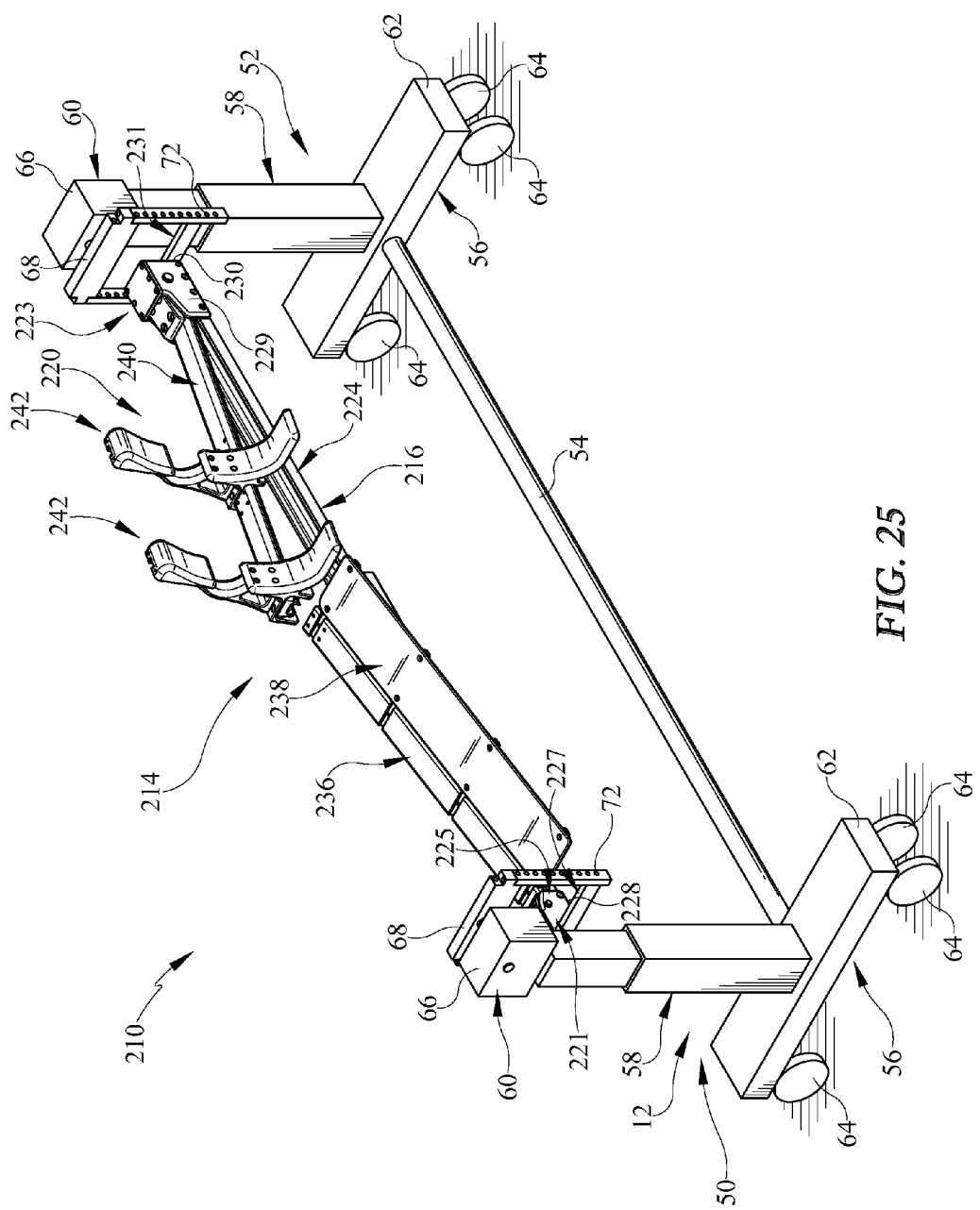
Figure 26A:
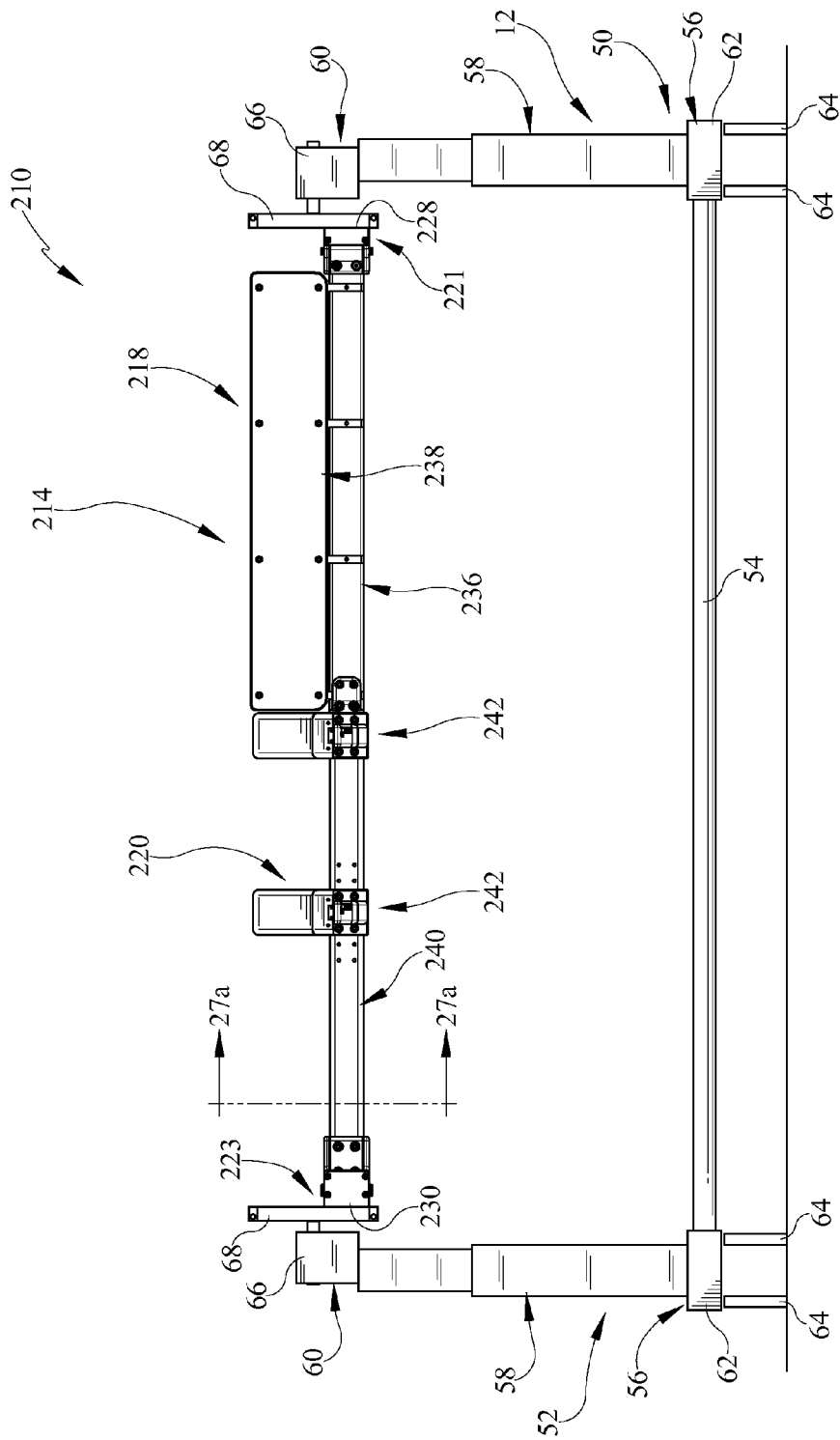
FIG. 26a is a left-side elevation view of the surgical support of FIG. 25 with the patient support arranged to support a patient in the prone or supine position.
Figure 26B:
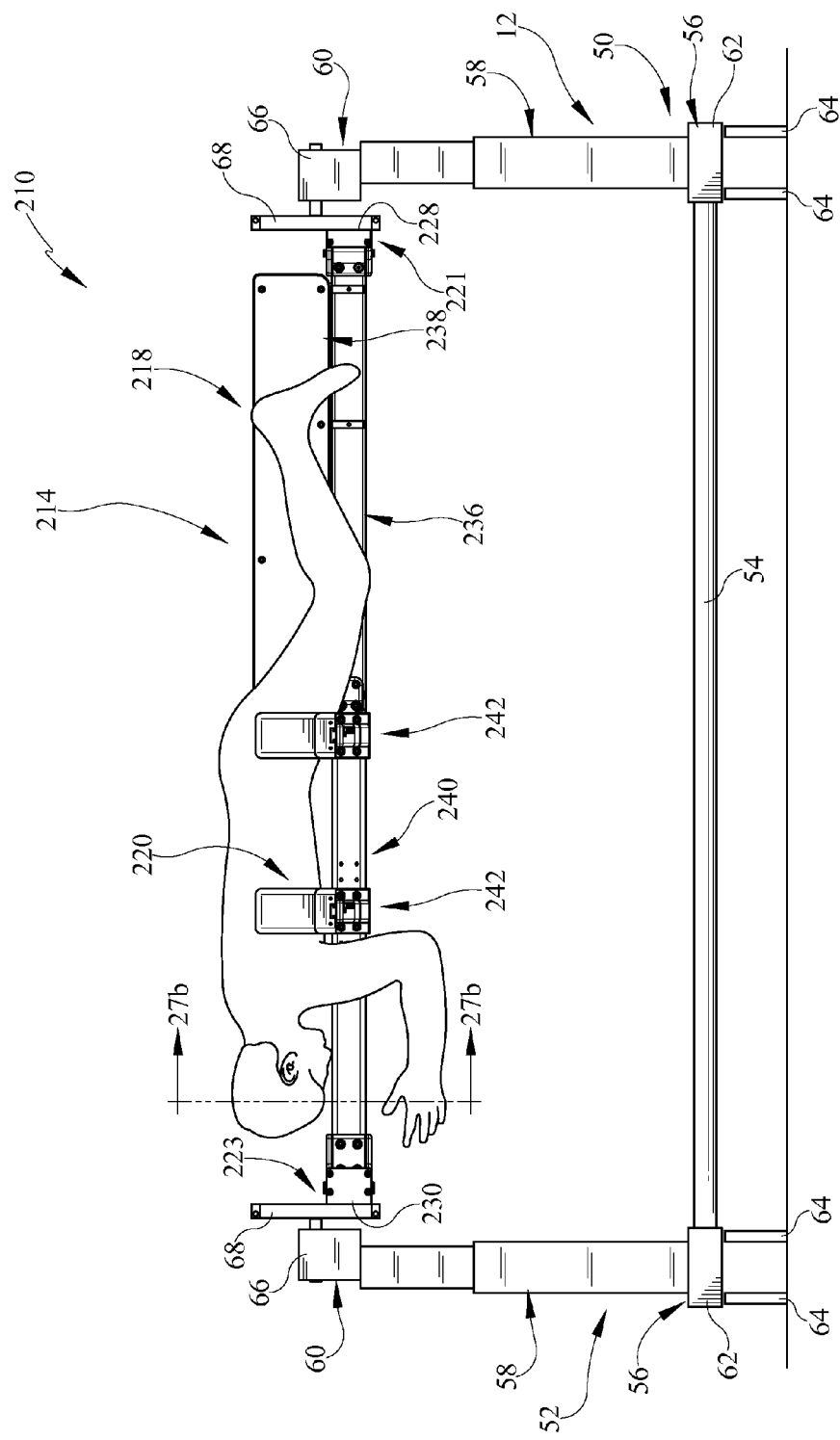
FIG. 26b is a view similar to FIG. 26a showing the patient resting on the patient support in the prone or supine position.
Figure 27A:
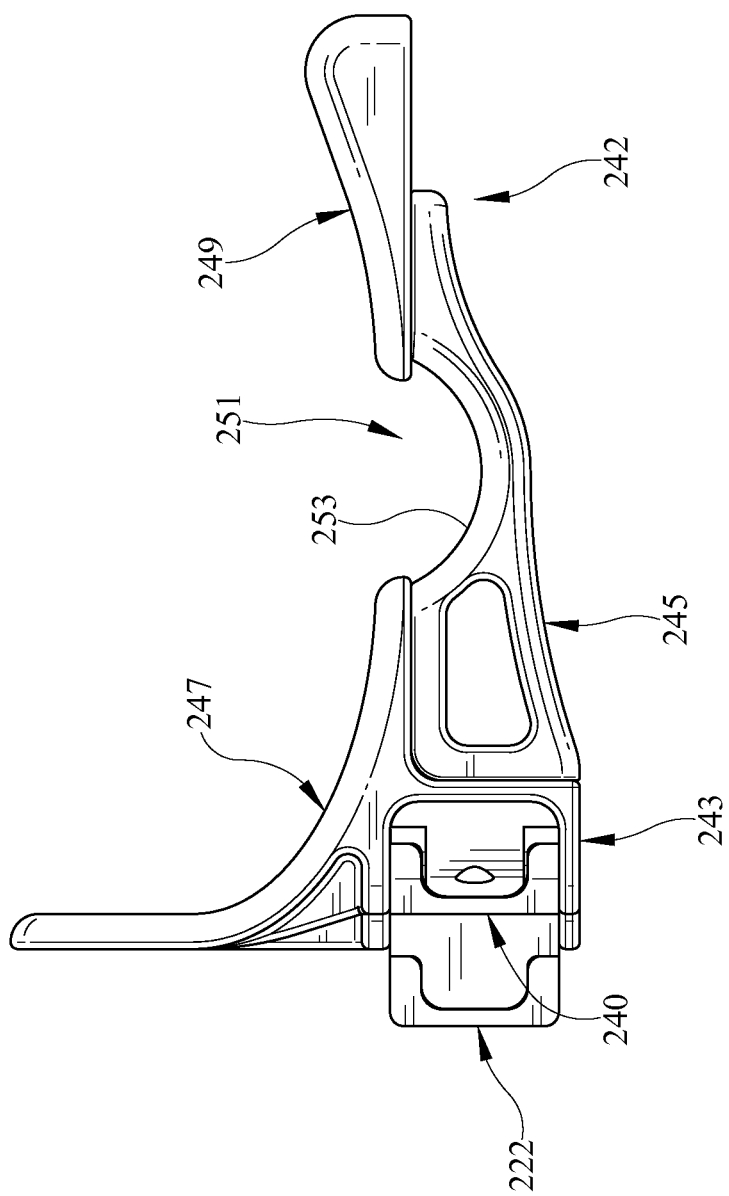
FIG. 27a is a partial head-end elevation view of the patient support of FIG. 26a showing the torso-support member included in the patient support.
Figure 27B:
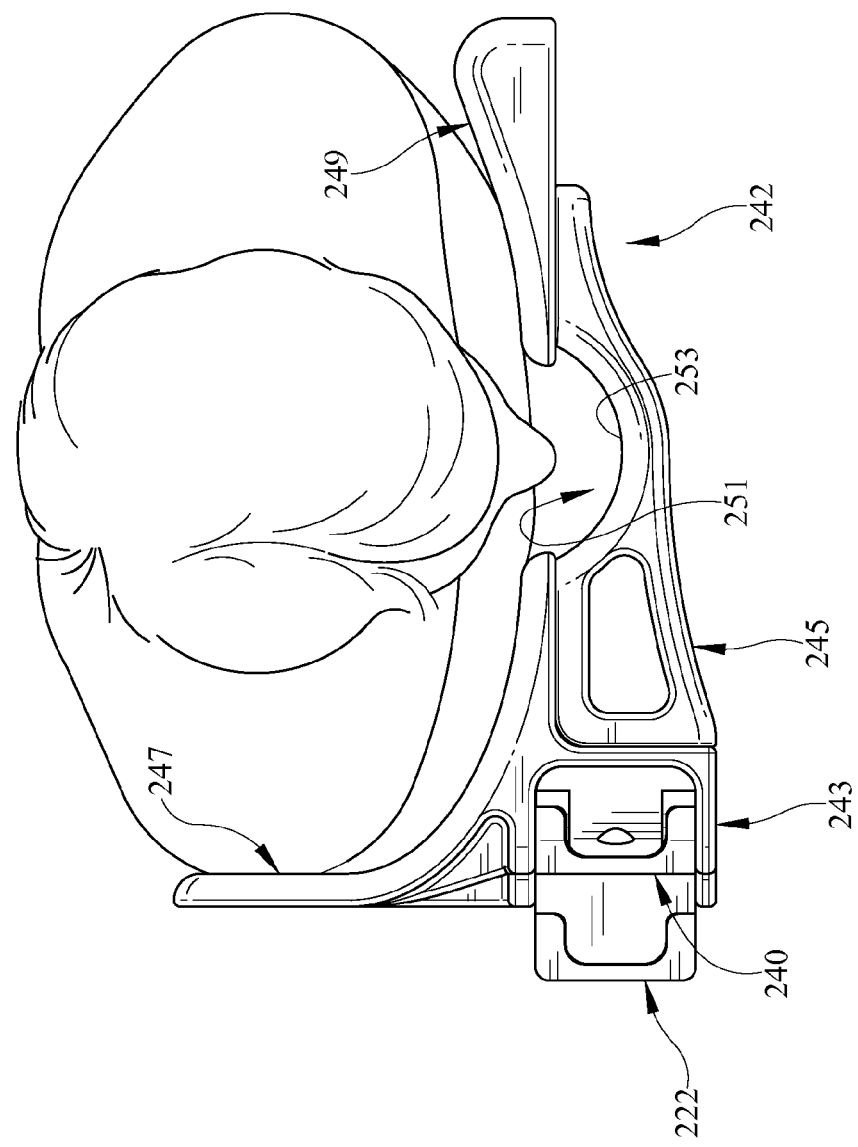
FIG. 27b is a view similar to FIG. 27a showing the patient resting on the patient support and engaging the torso-support member.
Figure 28:
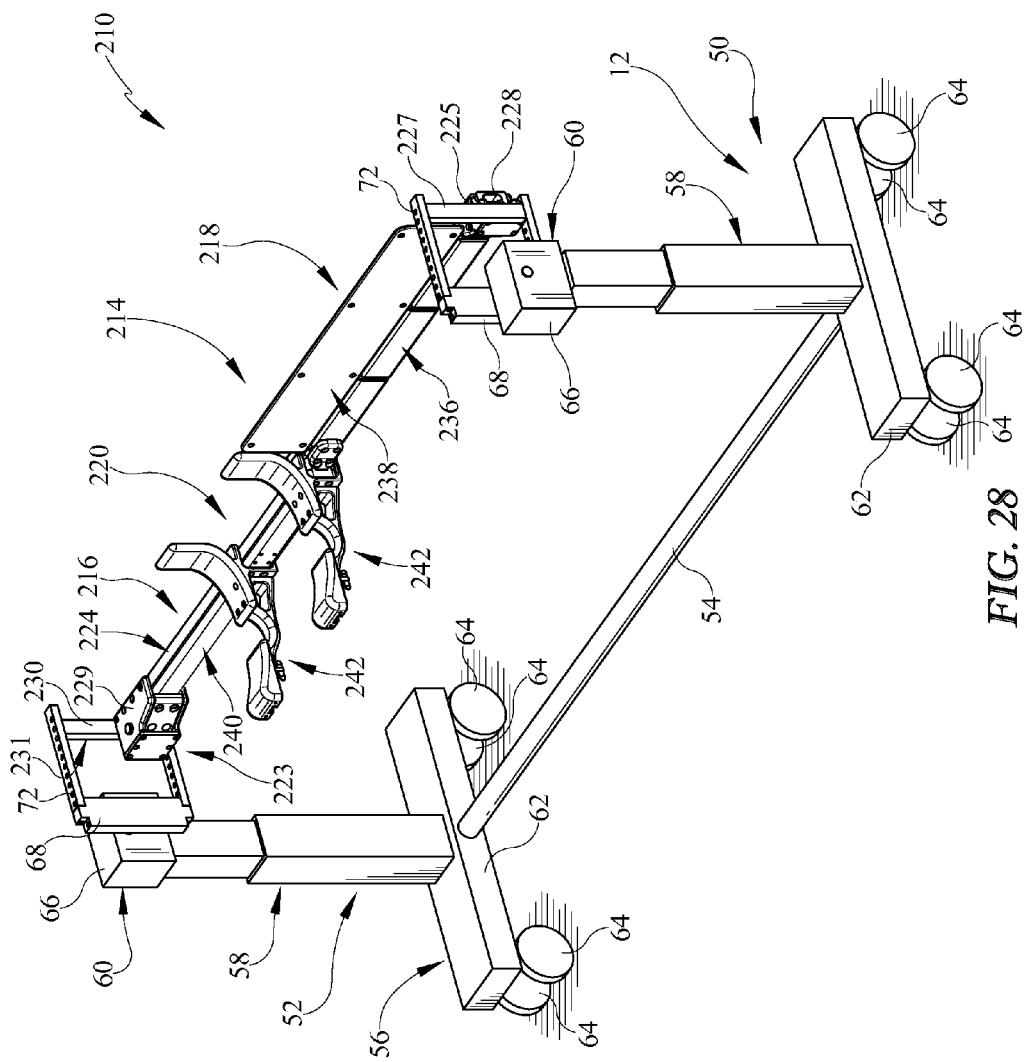

The patient support also includes a first adapter 221 and a second adapter 223 for mounting the patient support 214 to the foundation frame 12 as shown in FIG. 25. The first adapter 221 is coupled to the first end 228 of the base beam 216 and includes a pair of side panels 225 and a yoke 227.

The second adapter 223 is coupled to the second end 230 of the base beam 216 and includes a pair of side panels 229 and a yoke 231. The yokes 227, 231 are configured to releasably engage the adapter holes 72 of the foundation frame 12.

The leg support 218 of the illustrative embodiment includes a leg support beam 236 and a platform 238. The leg support beam 236 is pivotably coupled to the base beam 16. The platform 238 of the leg support 218 is coupled to the leg support beam 236 and extends out from the leg support beam 236.

The torso support 220 of the illustrative embodiment includes a torso support beam 240 and a pair of torso support members 242. The torso support beam 240 is pivotably coupled to base beam 16. The torso support members 242, alternately described as contoured supports, are slidably coupled to the torso support beam 240. By sliding the torso support members 242 along the torso support beam 240, a caregiver can arrange the torso support members 242 so that the patient is supported at the chest and the hips such that the patient's abdomen is free to hang down during a surgery when the patient is supported in the prone position. Torso support members 242 illustratively includes a coupler 243 configured to couple to the torso support beam 240, an L-shaped contoured pad 245, and a contoured shoulder pad 247.

In the illustrative embodiment, each torso support member 242 includes a mount 243, a frame 245, a proximal brace 247, and a distal brace 249. The mount 243 is configured to couple the torso support member 242 to the torso support beam 240. The frame 245 extends out from the mount 243. The proximal brace 247 is coupled to the frame 245 near the mount 243 and forms an arcuate L-shape to support a patient on the patient support 214 in the lateral, prone, or supine position. The distal brace 249 is coupled to the frame 245 and is spaced apart from the proximal brace 247 to form a relief opening 251 between the proximal brace 247 and the distal brace 249. The distal brace 249 is ramped and is configured to support a patient on the patient support 214 in the prone or supine position. In the illustrative embodiment, the relief opening 215 is augmented by a U-shaped surface 253 formed by the frame 245 between the proximal brace 247 and the distal brace 249.

The proximal and distal braces 247, 249 are shaped to encourage a patient toward the relief opening 251 between the proximal and distal braces 247, 249 when the patient is supported in the prone or supine position. The relief opening 251 is sized to relieve the patient's groin when the patient's hips are supported in the prone position on the torso support member 242. Additionally, the relief opening 251 is sized to allow surgical lines, such as catheters, to run along the length of the torso support members 242. In some embodiments, the torso support members 242 may include straps for securing a patient to the torso support 220. Additionally, a head support, an arm support, and a leg support wrap as described above with regard to the patient support 14 may be used with the patient support 214.

The patient support 214 also includes a drive (not shown) configured to simultaneously move the leg support 218 and the torso support 220 between the horizontal positions and the inclined positions. In other embodiments, the leg support 218 and the torso support 220 may be independently moved by the drive for all or a portion of their movement from the horizontal positions to a maximum inclined position. In some embodiments, the drive may be a manual drive with a hand crank. In other embodiments, the drive may include a motor and a controller.

FIGS. 29-39 illustrate a lateral-prone method of using the surgical support 10 shown in FIGS. 1-20. The lateral-prone method illustratively includes the steps of (i) moving the patient to the lateral position on the patient support 14, (ii) securing the patient to the patient support 14, (iii) reconfiguring the patient support 14 to obtain lateral flexion of the patient, and (iv) rotating the patient support 14 relative to the columns 58 of the foundation frame 12 so that the patient is supported in the prone position.

Figure 29:
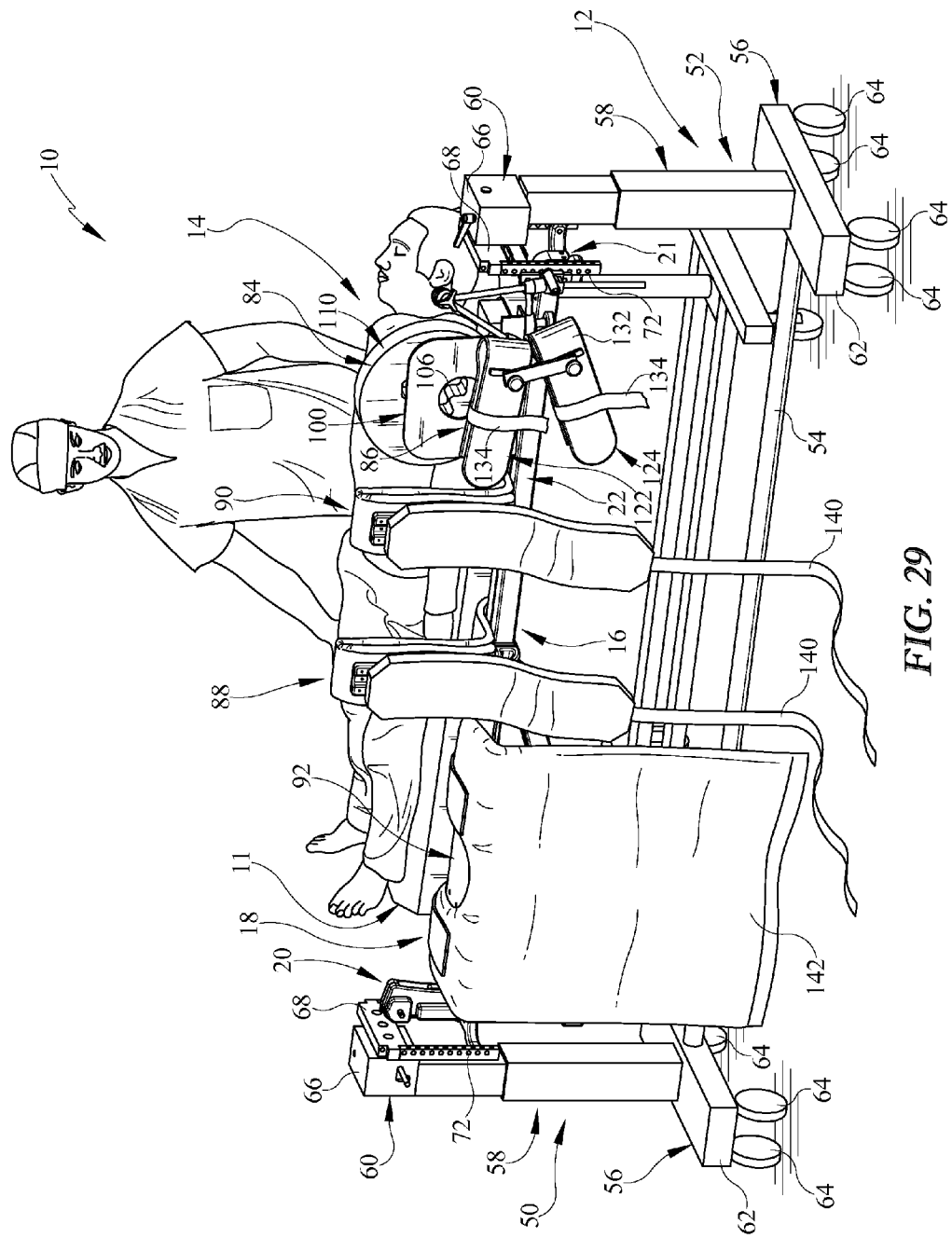
FIGS. 29-39 are a series of views showing an illustrative process for moving a patient onto the surgical support and then adjusting the position of the patient by way of the surgical support.
Figure 30:
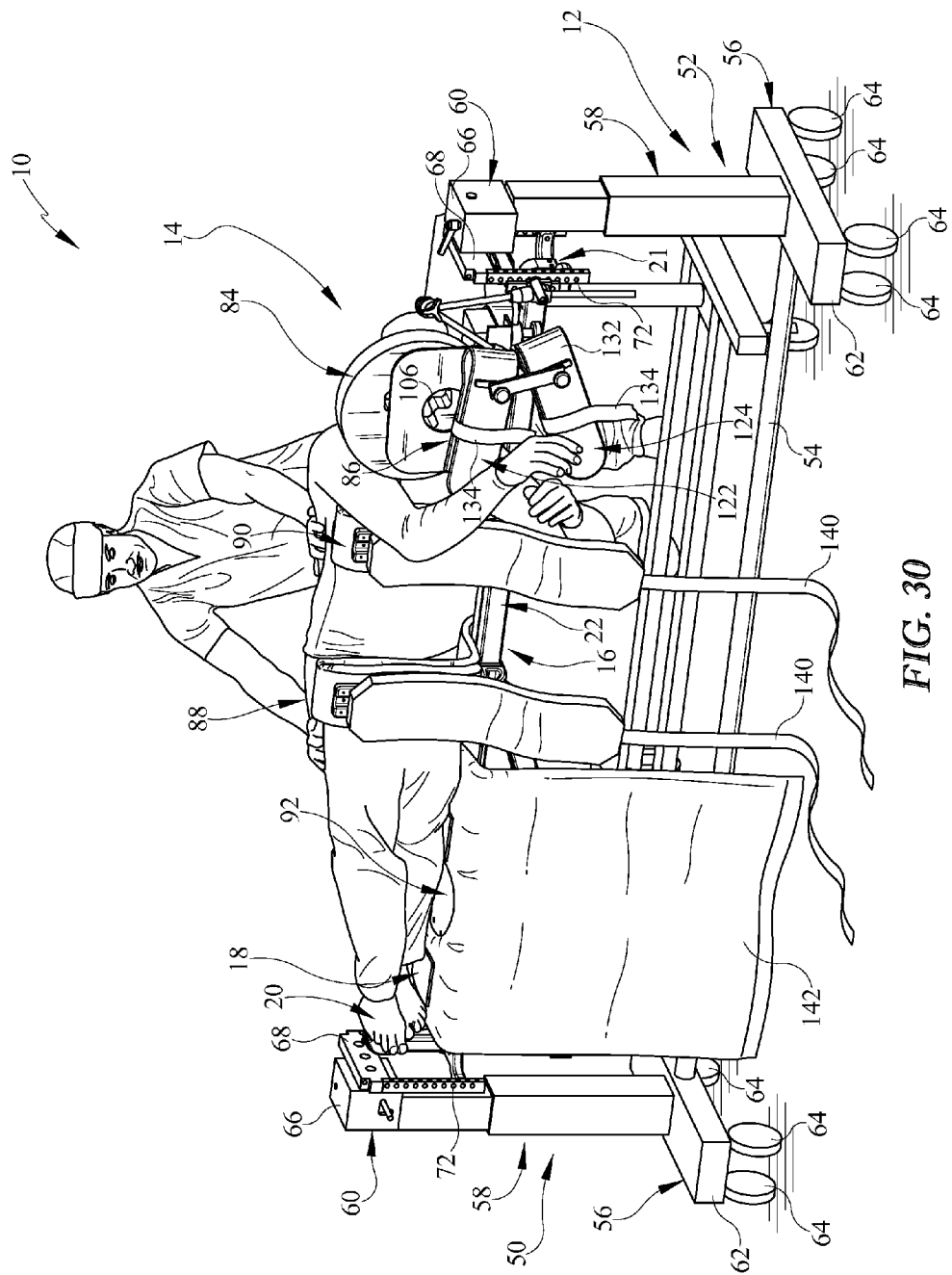

More specifically, as shown in FIG. 29, the first step of the method is moving a patient supported on a rolling preoperative table 11 adjacent the surgical support 10. Next, to move the patient onto the patient support 14, the patient is rolled from the supine position on the preoperative table 11 to the lateral position on the patient support 14 of the surgical table as shown in FIG. 30. In the present embodiment, the patient need not be lifted to transfer the patient from the preoperative table 11 to the surgical support 10. In other embodiments, the patient may be lifted on to the surgical support 10.

Figure 31:
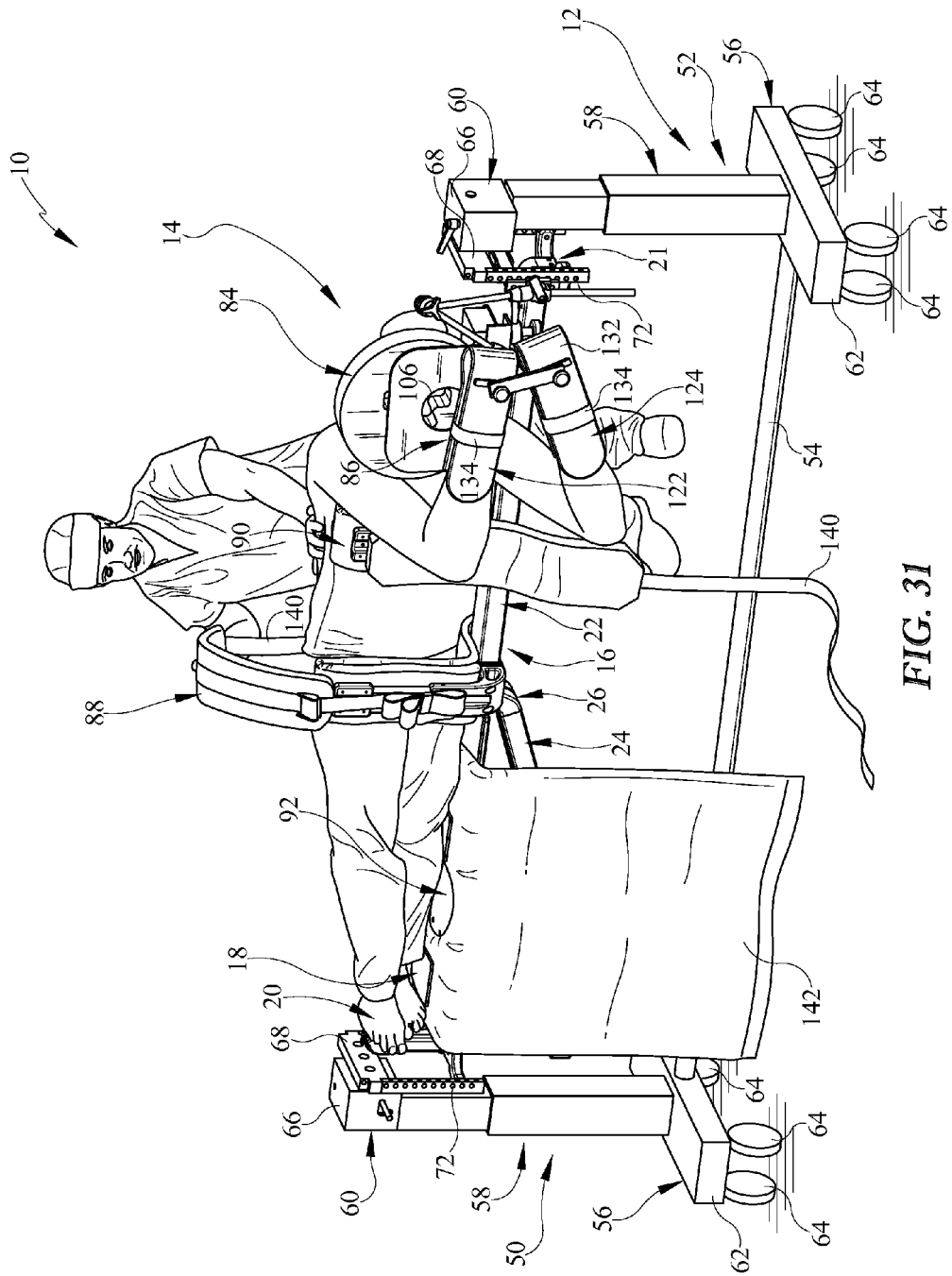
Figure 32:
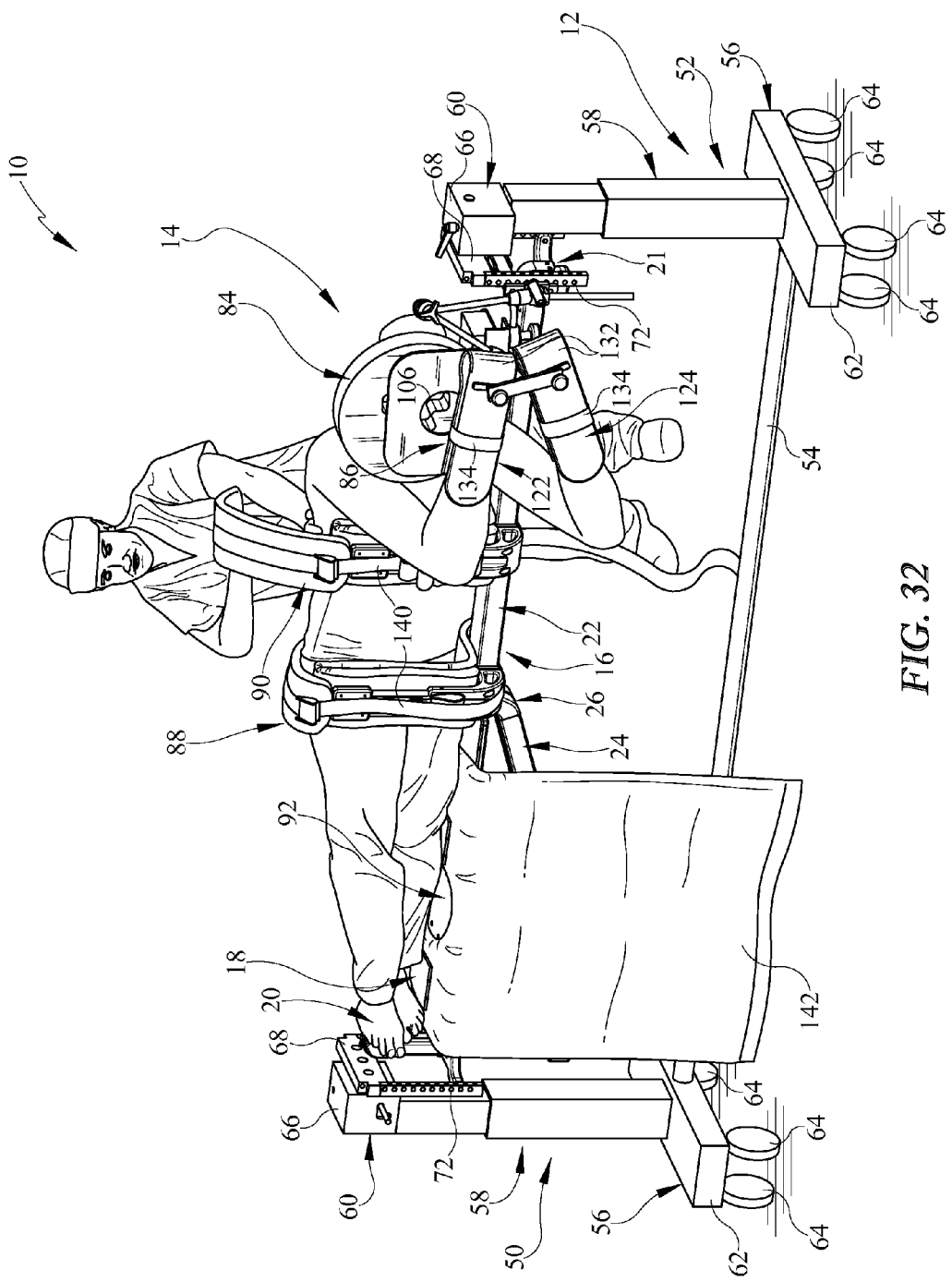
Figure 33:
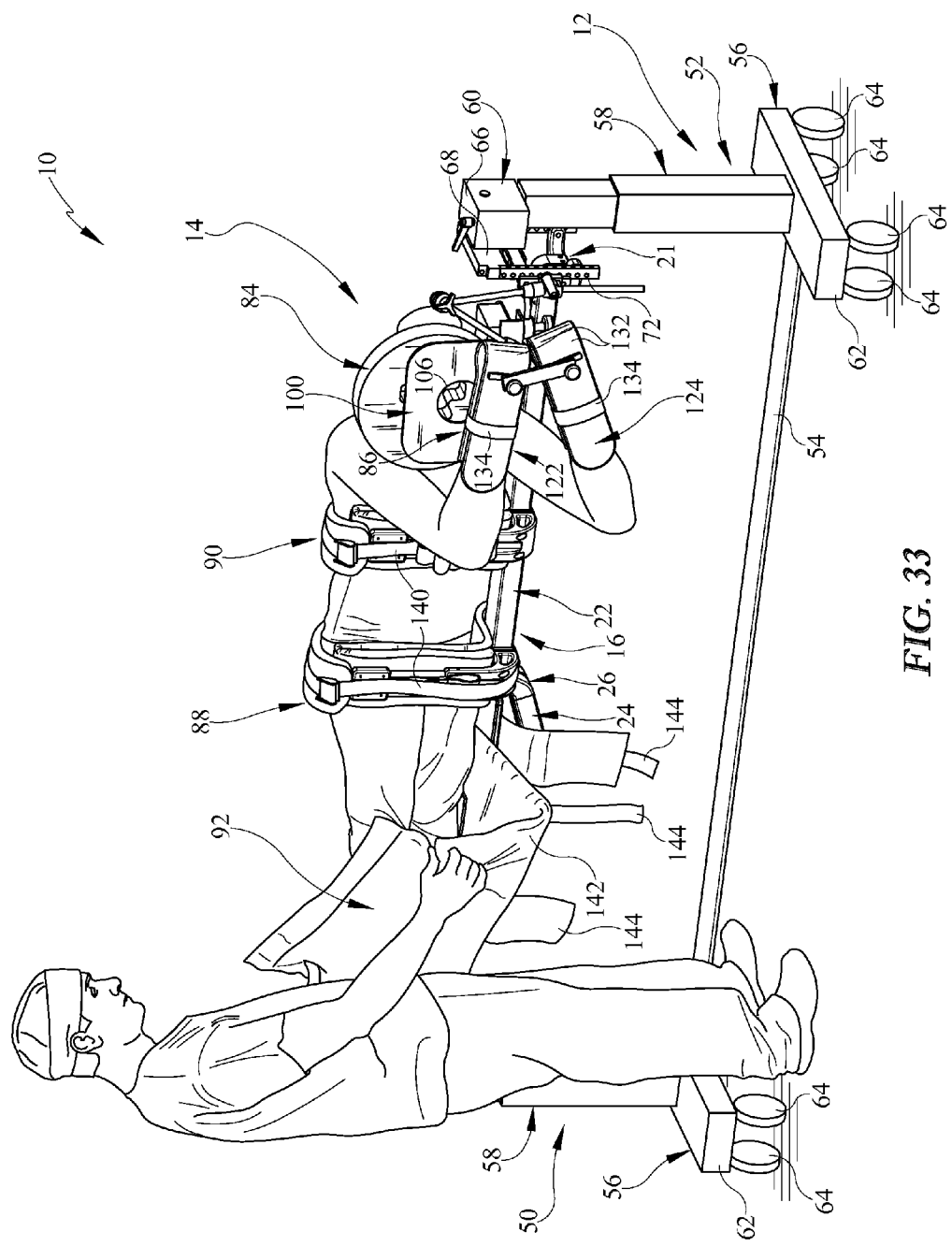
Figure 34:
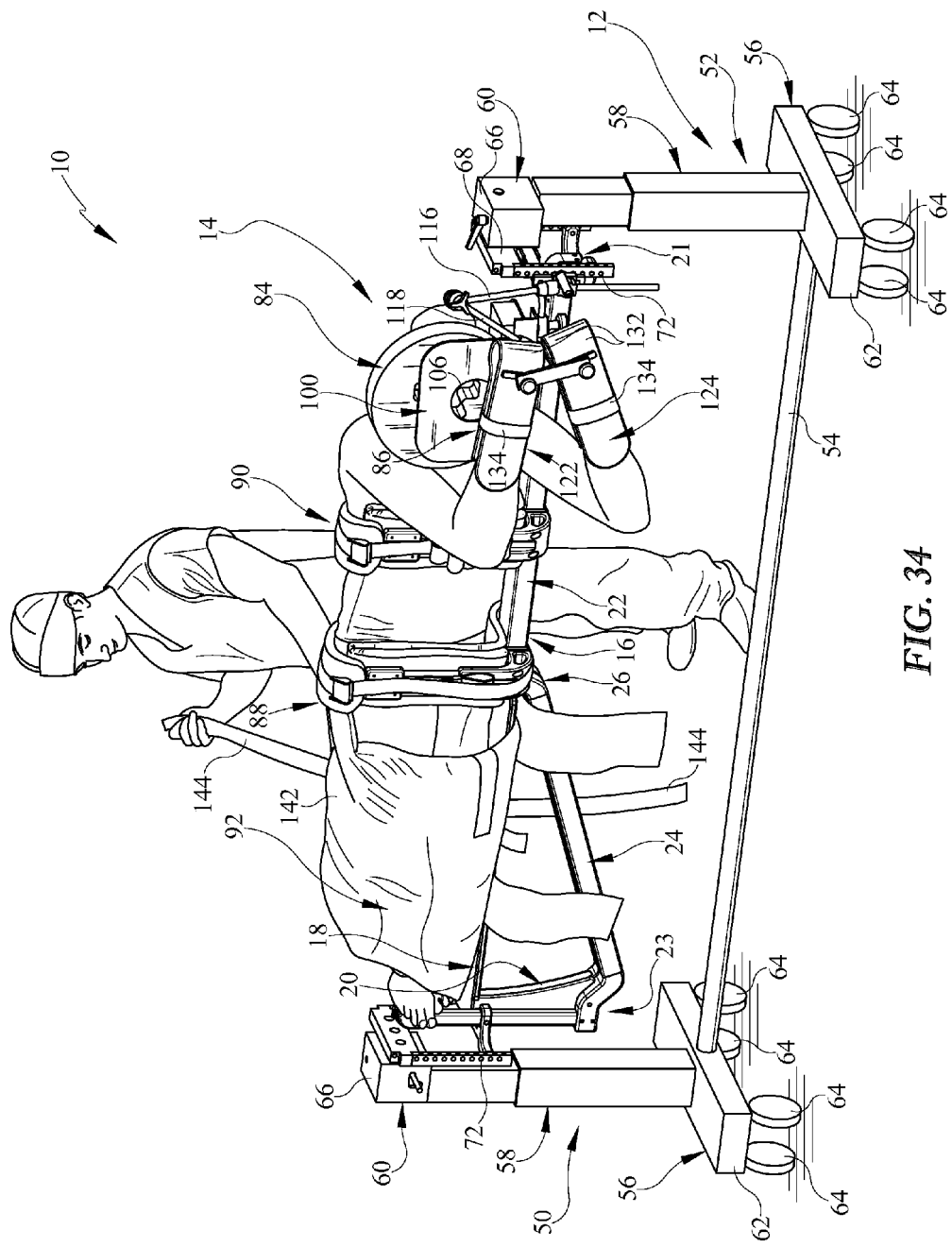
Figure 35:
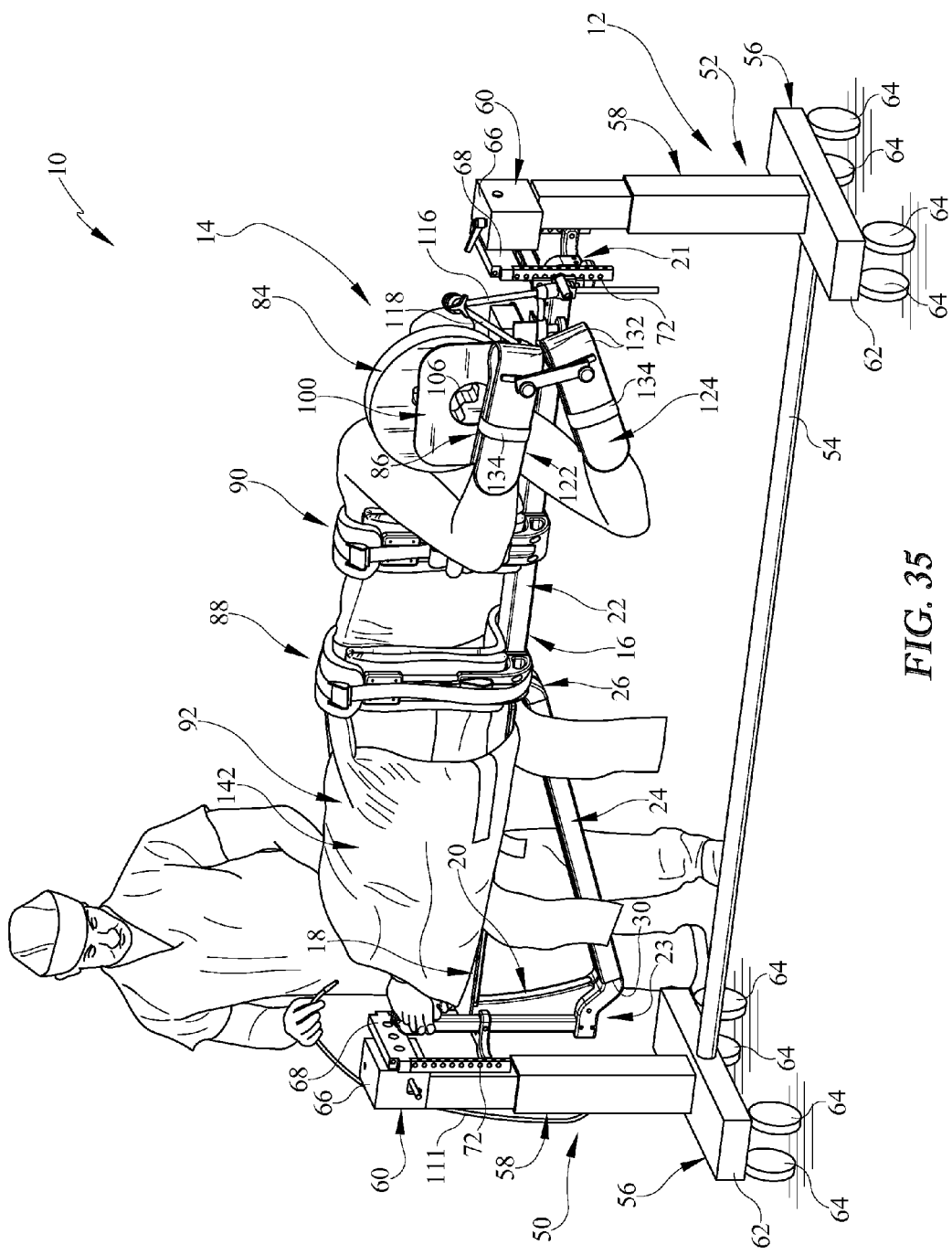

FIGS. 31-35 show the patient being secured to the patient support. Specifically, FIG. 31 shows the patient's forearms inserted into the mitts 122, 124 of the arm support 86 with the straps 134 of the arm support 86 being secured around the patient's arms. FIGS. 31-32 show the straps 140 of the torso supports 88, 90 being wrapped around the patient's torso at the chest and the hips. The straps 140 of the torso supports are then secured. FIG. 33 shows the vacuum bag 142 of the leg wrap support 92 being wrapped around the patient's legs. In some embodiments, a cushion may be inserted between the patient's legs prior to the leg wrap support 92 being wrapped around the patient's legs. FIG. 34 shows the straps 144 of the leg wrap support 92 being wrapped around the patient's legs and securing the patient's legs to the leg support 18. FIG. 35 shows the leg wrap support 92 after an external vacuum source 101 has been applied to the valve 150 so that excess air has been removed from the vacuum bag 142 and the vacuum bag 142 has become inflexible so that the patient's legs are immobilized.

FIGS. 36-37 show the patient support 14 being reconfigured to cause lateral flexion of the patient's torso relative to the patient's legs. FIG. 36 shows the drive 44 of the patient support 14 being operated by turning the removable hand crank 45 so that the leg support 18 is moved from the horizontal position (shown in FIG. 36) to the inclined position (shown in FIG. 37). FIG. 37 shows the patient supported laterally on the patient support 14 and flexed laterally so that the patient's pelvis is moved away from the patient's rib cage along the side of the patient spaced apart from the base beam 16 and the leg support 18 as suggested by the surgeon pointing to the created space.

Figure 38:
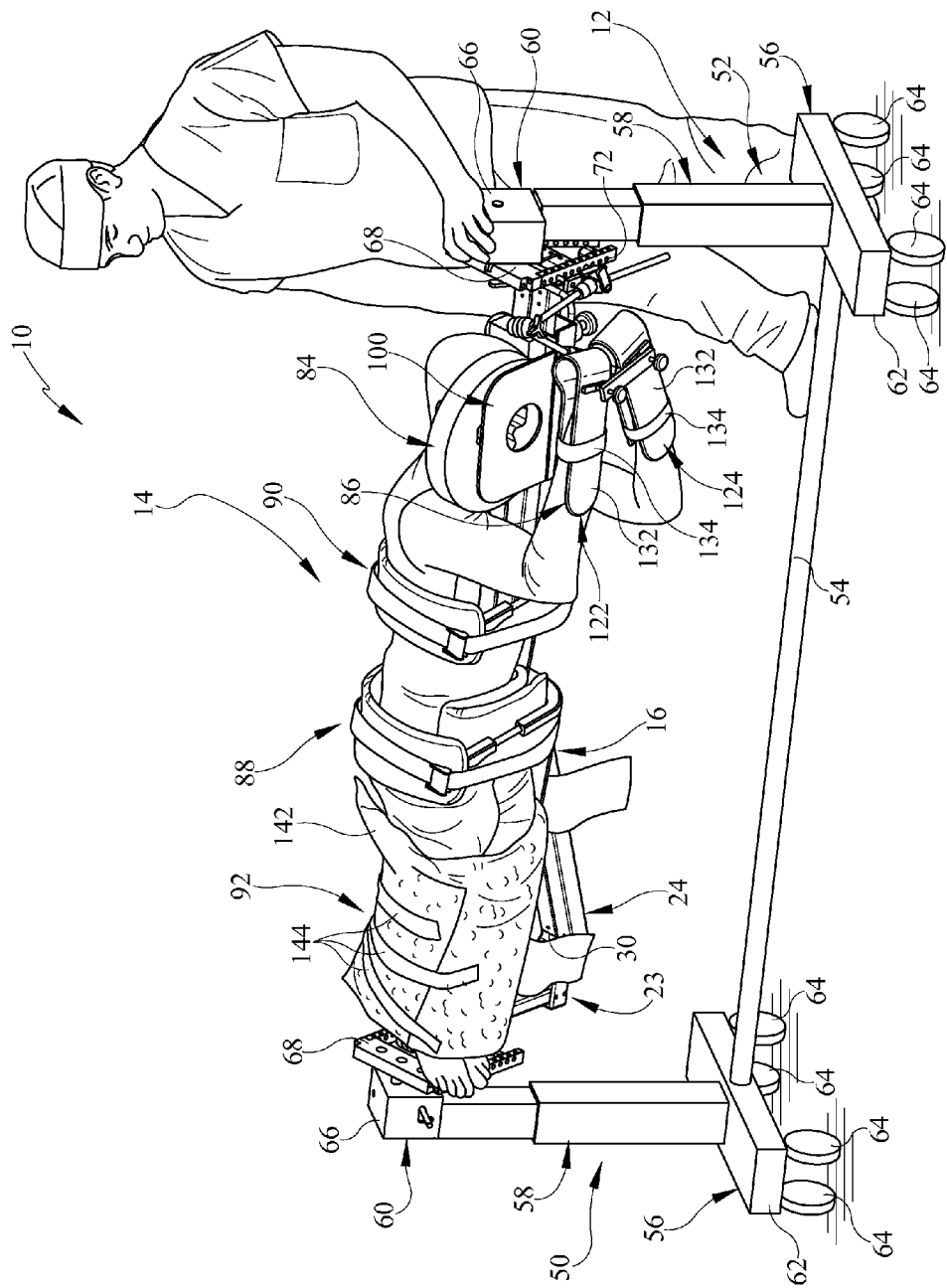

FIGS. 38-39 show the step of rotating the patient support 14 relative to the columns 58 of the foundation frame 12 so that the patient is moved from the lateral position to the prone position. In FIG. 38, the connection frames 68 of the foundation frame 12 are rotated via a manual mechanism so that the patient support 14 is rotated around the axis 14A and the patient is moved with the patient support 14. FIG. 39 shows the patient support 14 rotated around ninety degrees so that the patient is in the prone position and is supported by the torso supports 88, 90 cantilevered out from the base beam 16. In other embodiments, the patient support 14 may include a motor and a control for powered rotation of the patient support 14 relative to the columns 58 of the foundation frame 12. In some embodiments, the patient may be moved back to the lateral position after being placed in the prone position.

In some embodiments of the lateral-prone method, the surgical drape 160 may be used along with the surgical support 10. In such embodiments, the method of using the surgical drape to selectively expose a first surgical site and then second surgical site as described above may be incorporated in the method.

FIGS. 40-53 illustrate a lateral-supine method of using the surgical support 10 shown in FIGS. 1-20. The lateral-prone method illustratively includes the steps of (i) moving the patient to the lateral position on the patient support 14, (ii) securing the patient to the patient support 14, (iii) reconfiguring the patient support 14 to obtain lateral flexion of the patient, and (iv) rotating the patient support 14 relative to the foundation frame 12 so that the patient is supported in the supine position.

Figure 41:
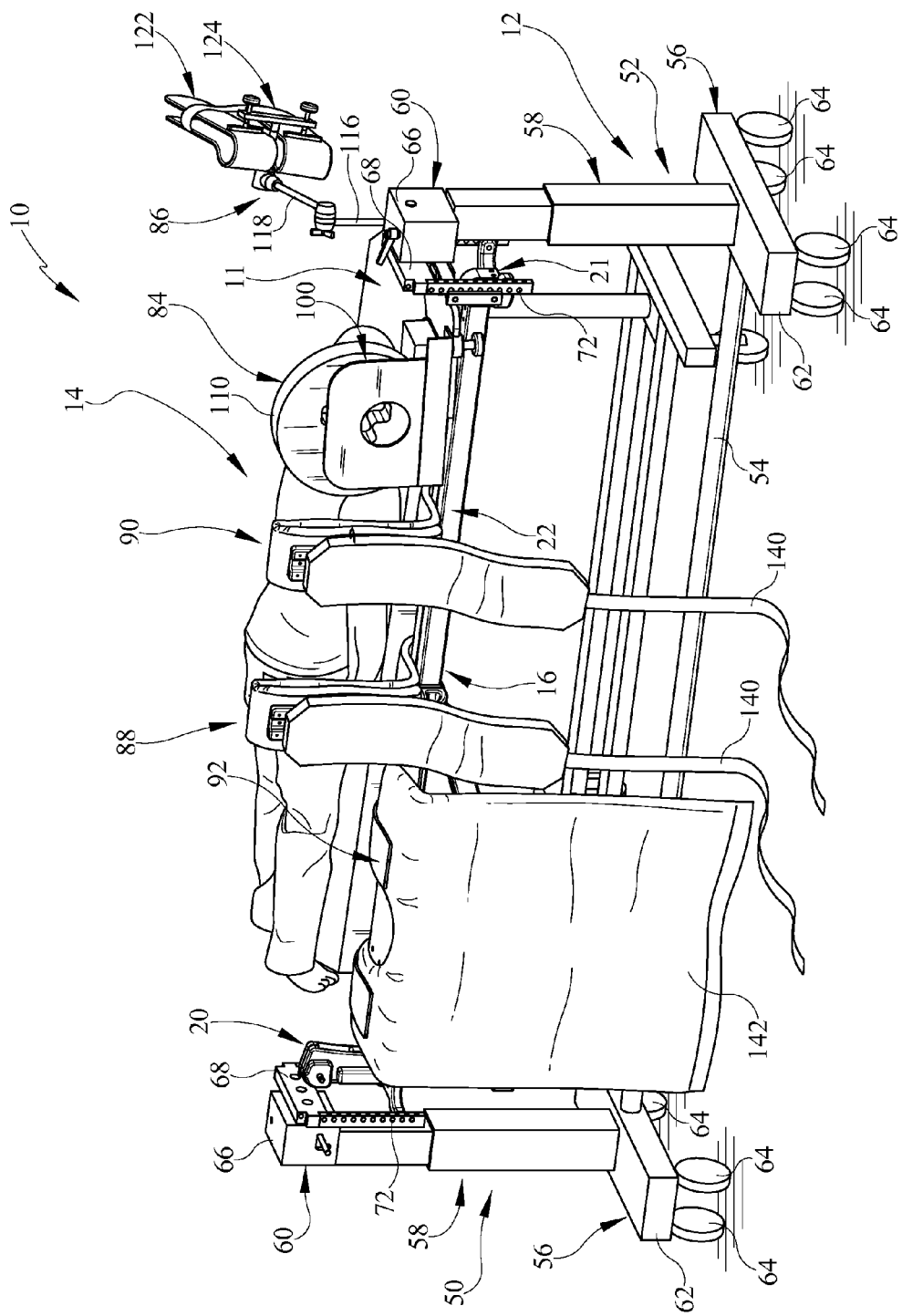
Figure 42:
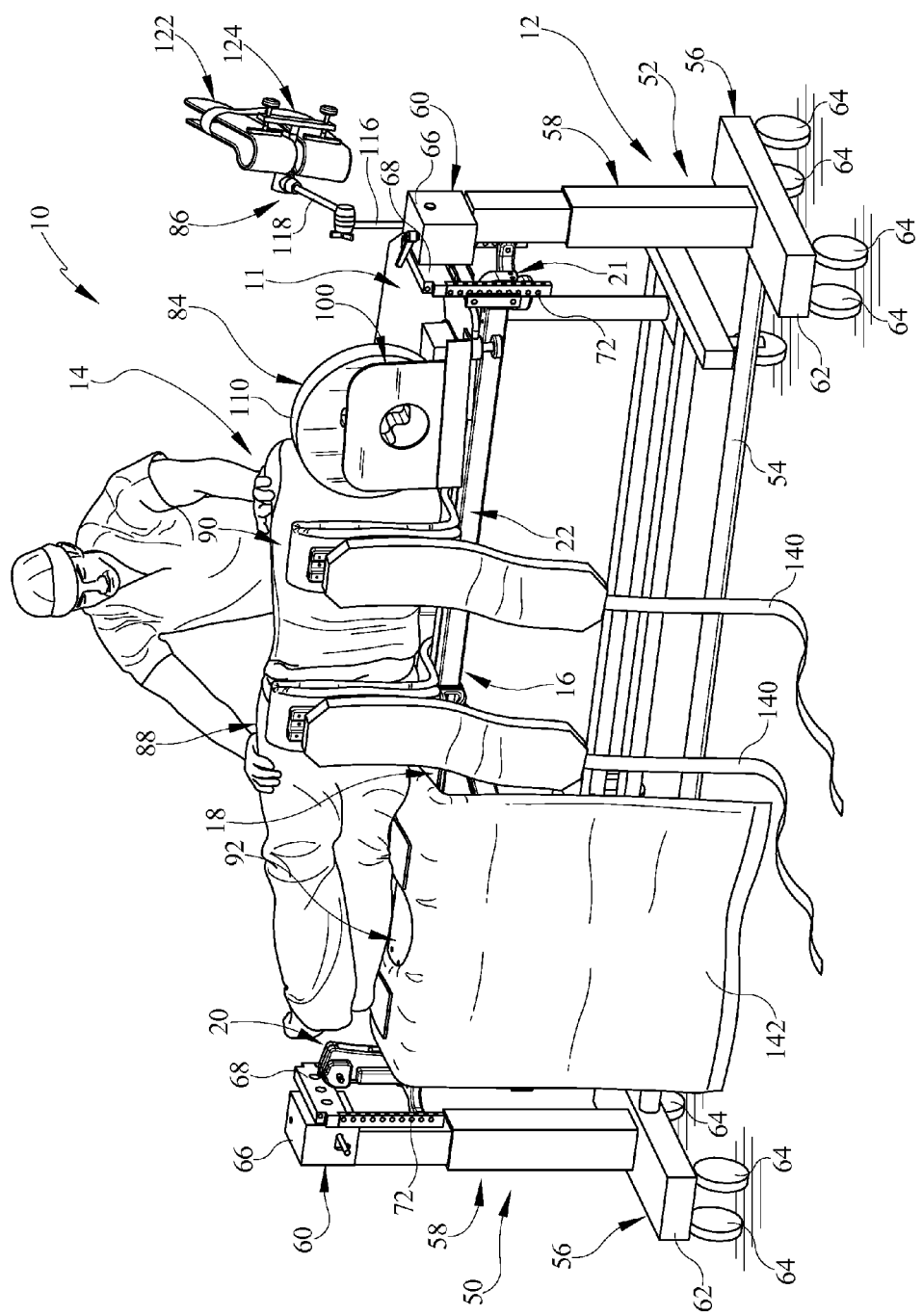

Specifically, as shown in FIG. 41, the first step of the method is moving a patient supported on a rolling preoperative table 11 adjacent the surgical support 10. Next, to move the patient onto the patient support 14, the patient is rolled from the prone position on the preoperative table 11 to the lateral position on the patient support 14 of the surgical table as shown in FIG. 42. In the present embodiment, the patient need not be lifted to transfer the patient from the preoperative table 11 to the surgical support 10. In other embodiments, the patient may be lifted on to the surgical support 10.

Figure 43:
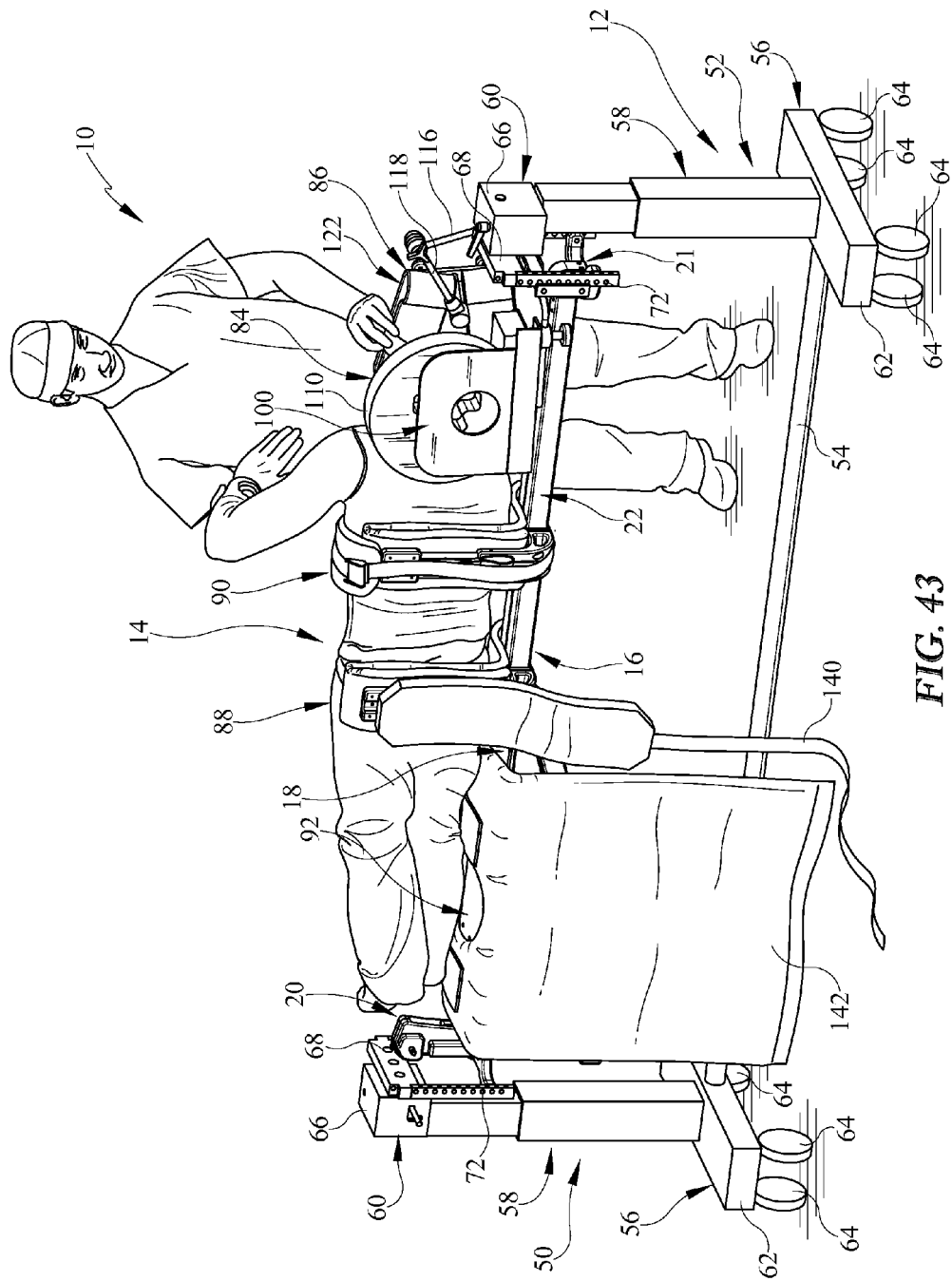
Figure 44:
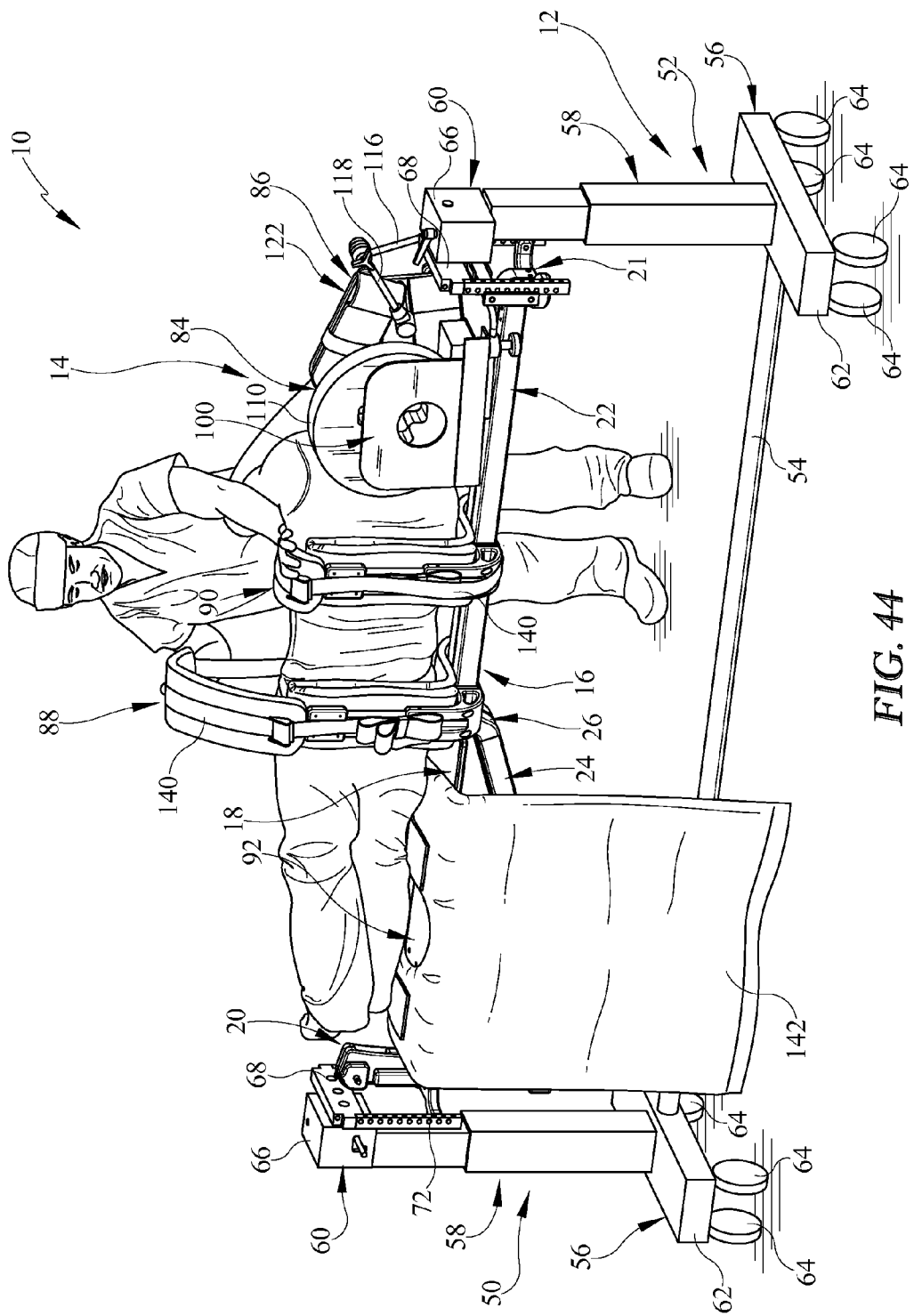
Figure 45:
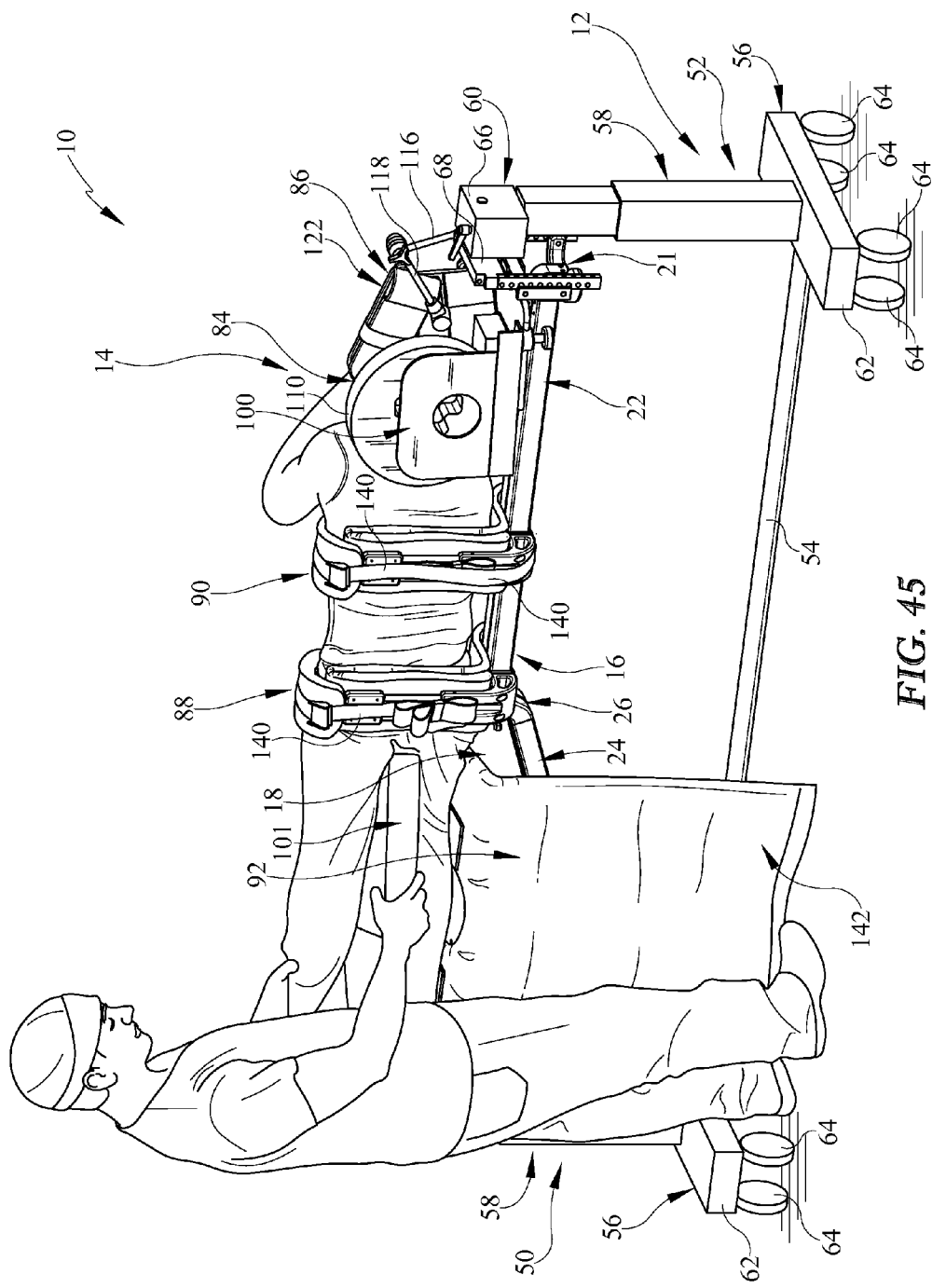
Figure 46:
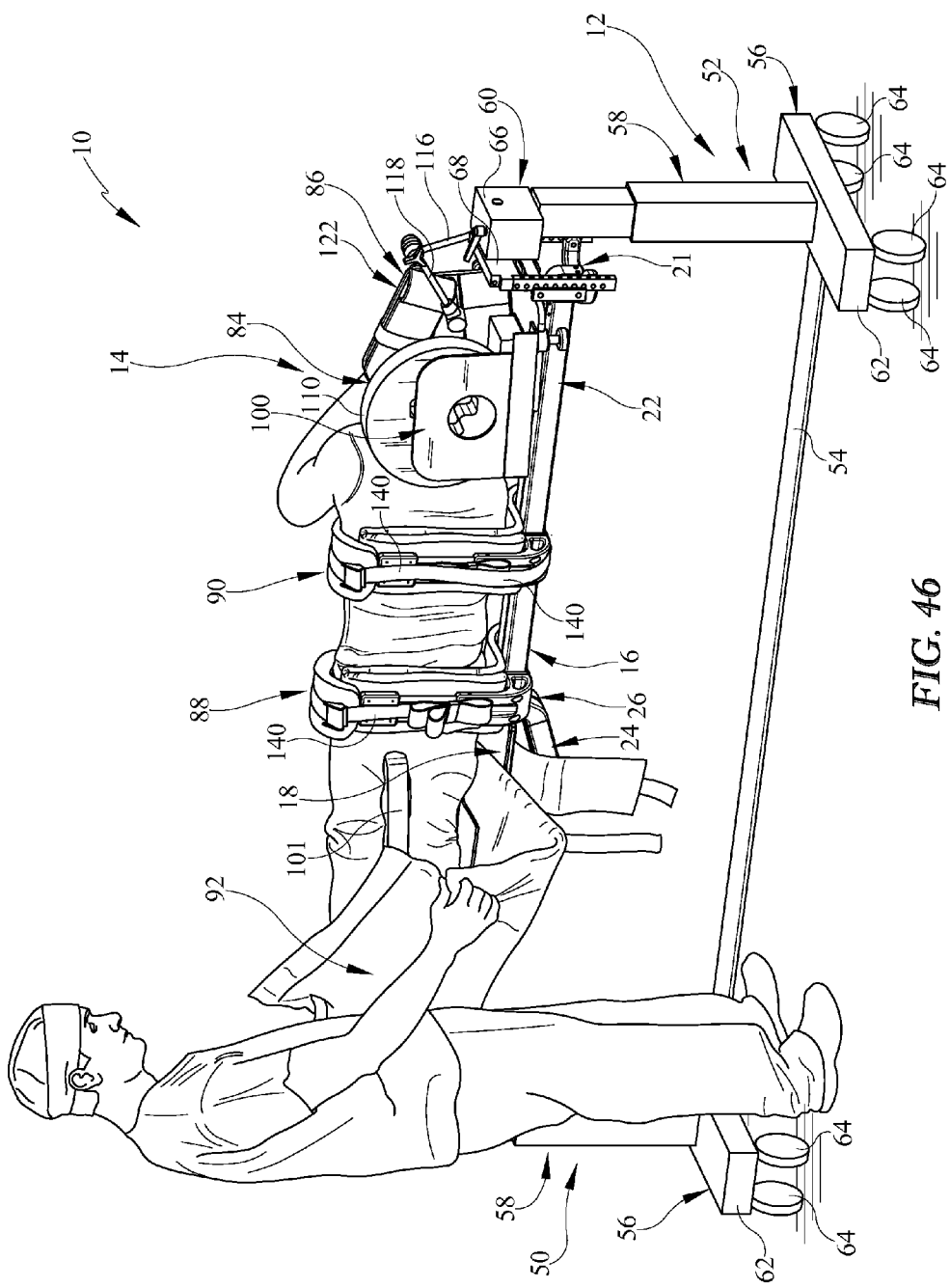
Figure 47:
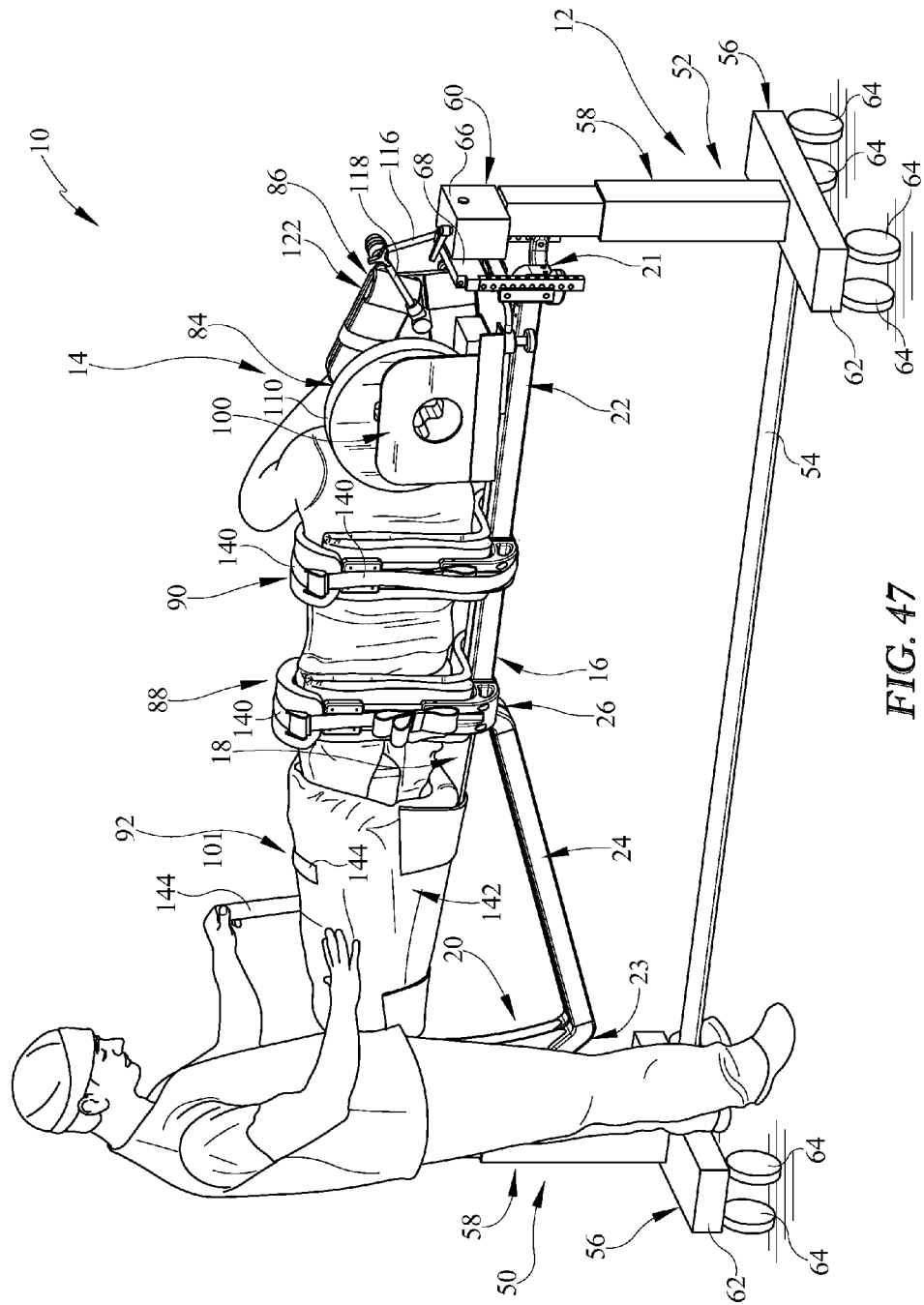

FIGS. 43-47 show the patient being secured to the patient support. Specifically, FIG. 43 shows the patient's forearms being inserted into the mitts 122, 124 of the arm support 86 with the straps 134 of the arm support 86 being secured around the patient's arms. FIG. 44 show the straps 140 of the torso supports 88, 90 being wrapped around the patient's torso at the chest and the hips. The straps 140 of the torso supports are then secured. FIG. 45 shows a cushion 111 being inserted between the patient's legs prior to the leg wrap support 92 being wrapped around the patient's legs. FIG. 46 shows the vacuum bag 142 of the leg wrap support 92 being wrapped around the patient's legs. FIG. 47 shows the straps 144 of the leg wrap support 92 being wrapped around the patient's legs and securing the patient's legs to the leg support 18. FIG. 48 shows the leg wrap support 92 after an external vacuum source 101 has been applied to the valve 150 so that excess air has been removed from the vacuum bag 142 and the vacuum bag 142 has become inflexible so that the patient's legs are immobilized.

FIGS. 49-50 show the patient support 14 being reconfigured to cause lateral flexion of the patient's torso relative to the patient's legs. FIG. 49 shows the drive 44 of the patient support 14 being operated by turning the removable hand crank 45 so that the leg support 18 is moved from the horizontal position (shown in FIG. 49) to the inclined position (shown in FIG. 50). FIG. 50 shows the patient supported laterally on the patient support 14 and flexed laterally so that the patient's pelvis is moved away from the patient's rib cage along the side of the patient spaced apart from the base beam 16 and the leg support 18.

Figure 51:
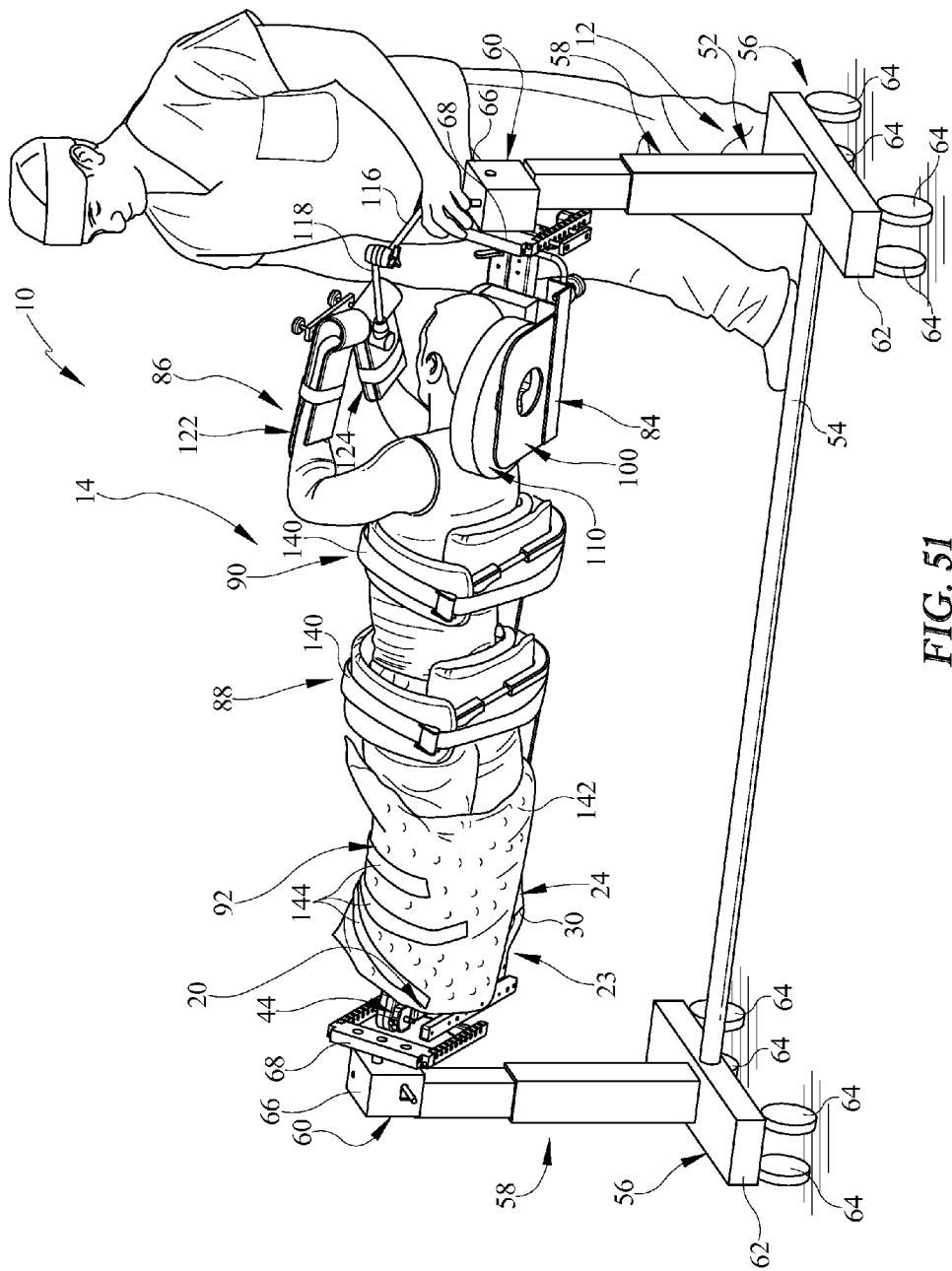
Figure 52:
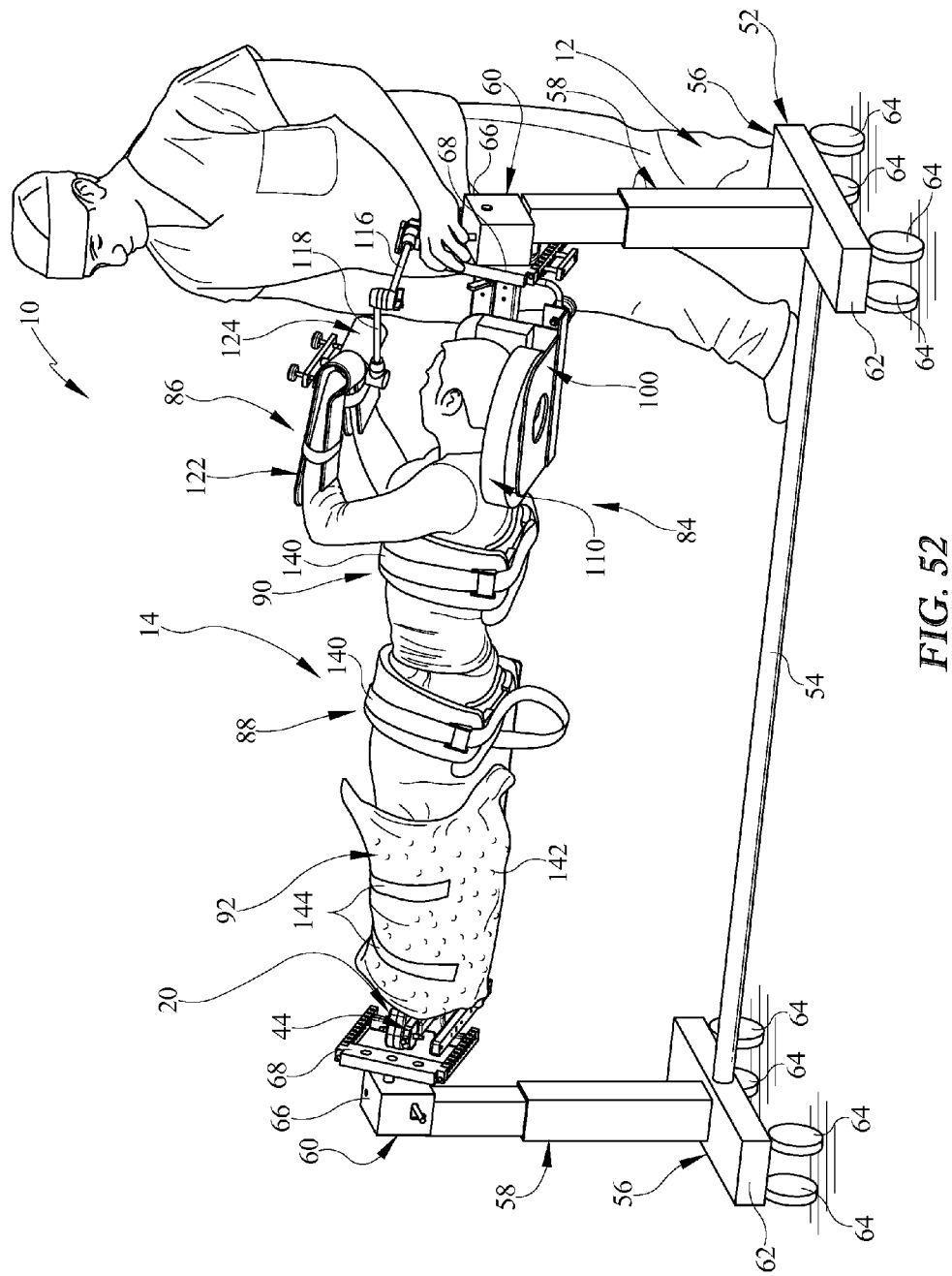

FIGS. 51-53 show the step of rotating the patient support 14 relative to the foundation frame 12 so that the patient is moved from the lateral position to the supine position. In FIGS. 51-52, the connection frames 68 of the foundation frame 12 are rotated via a manual mechanism so that the patient support 14 is rotated around the axis 14A and the patient is moved with the patient support 14. FIG. 53 shows the patient support 14 rotated around ninety degrees so that the patient is in the supine position and is supported by the torso supports 88, 90 cantilevered out from the base beam 16. In other embodiments, the patient support 14 may include a motor and a control for powered rotation of the patient support 14 relative to the columns 58 of the foundation frame 12. In some embodiments, the patient may be moved back to the lateral position after being placed in the supine position.

In some embodiments of the lateral-supine method, the surgical drape 160 may be used along with the surgical support 10. In such embodiments, the method of using the surgical drape to selectively expose a first surgical site and then second surgical site as described above may be incorporated in the method.

Although certain illustrative embodiments have been described in detail above, many embodiments, variations and modifications are possible that are still within the scope and spirit of this disclosure as described herein and as defined in the following claims.

The invention claimed is:

1. A method of performing abdomen surgery, the method comprising
    wrapping a surgical drape around the patient wherein the surgical drape includes a main sheet section, a first pull-away sheet section coupled to the main sheet section, and a second pull-away sheet section coupled to the main sheet section,
    pulling the first pull-away sheet section to expose at least part of an opening in the main sheet section while the first pull-away sheet section remains coupled to the main sheet section,
    performing a first portion of a surgical procedure in the opening exposed by pulling the first pull-away sheet section,
    pulling away the second pull-away sheet section to expose the rest of the opening in the main sheet section while the second pull-away sheet section remains coupled to the main sheet section, and
    performing a second portion of the surgical procedure in the opening exposed by pulling away the second pull-away sheet section.

2. The method of claim 1, wherein the first pull-away sheet section is secured in position relative to the opening before being pulled away to expose at least part of the opening in the main sheet section by strips of adhesive.

3. The method of claim 2, wherein the second pull-away sheet section is secured in position relative to the opening before being pulled away to expose at least part of the opening in the main sheet section by strips of adhesive.

4. The method of claim 3, wherein the strips of adhesive are applied on opposite sides of the opening.

5. The method of claim 4, wherein the second pull-away sheet section is secured in position relative to the opening before being pulled away to expose at least part of the opening in the main sheet section by stitching.

6. The method of claim 5, wherein the stitching is applied on opposite sides of the opening.

7. The method of claim 1, wherein the step of pulling the first pull-away sheet section to expose at least part of the opening in the main sheet section is performed while the patient is supported in a lateral position on a patient support.

8. The method of claim 7, further comprising rotating a patient support upon which the patient is supported relative to a foundation frame so that the patient is moved from being supported in a substantially lateral position to being supported in a substantially supine position.

9. The method of claim 8, wherein the step of pulling away the second pull-away sheet section to expose at least part of the opening in the main sheet section is performed after rotation of the patient support upon which the patient is supported relative to the foundation frame so that the patient is moved from being supported in the substantially lateral position to being supported in the substantially supine position.

10. The method of claim 7, wherein the step of pulling the first pull-away sheet section to expose at least part of the opening in the main sheet section is performed while the patient is subjected to lateral flexion.

11. The method of claim 1, wherein the first pull-away sheet section extends from a top edge of the main sheet section and is folded over the main sheet section to cover a portion of the opening.

12. The method of claim 11, wherein the second pull-away sheet section extends from a bottom edge of the main sheet section, opposite the top edge, and is folded over the main sheet section to cover a portion of the opening.

13. The method of claim 1, wherein the first pull-away sheet section is secured in position relative to the opening before being pulled away to expose at least part of the opening in the main sheet section by stitching.

14. The method of claim 1, wherein the surgical drape is wrapped around the patient so that a top portion of the opening covered by the first pull-away sheet section is positioned over a patient's side abdomen and a bottom portion of the opening covered by the second pull-away sheet section is positioned over a patient's back.

* * * * *

UNITED STATES PATENT AND TRADEMARK OFFICE
CERTIFICATE OF CORRECTION

PATENT NO. : 9,937,006 B2
APPLICATION NO. : 14/735746
DATED : April 10, 2018
INVENTOR(S) : Thomas K. Skripps et al.

It is certified that error appears in the above-identified patent and that said Letters Patent is hereby corrected as shown below:

On the Title Page

Line 9 of item (57) ABSTRACT, delete "The, guide" and insert in its place, --The guide--.

Signed and Sealed this
Fourth Day of March, 2025

Coke Morgan Stewart
*Acting Director of the United States Patent and Trademark Office*